US008420638B2

(12) United States Patent
Attardo et al.

(10) Patent No.: US 8,420,638 B2
(45) Date of Patent: Apr. 16, 2013

(54) TRIHETEROCYCLIC COMPOUNDS AND COMPOSITIONS THEREOF

(75) Inventors: Giorgio Attardo, Vimont (CA);
Jean-Francois Lavallee, Milles-Iles (CA); Elise Rioux, Montreal (CA);
Sasmita Tripathy, Pierrefonds (CA);
Terrance W. Deyle, Killingworth (CA)

(73) Assignee: Gemin X Pharmaceuticals Canada Inc., Montreal, Quebec (CA)

( * ) Notice: Subject to any disclaimer, the term of this patent is extended or adjusted under 35 U.S.C. 154(b) by 0 days.

(21) Appl. No.: 13/171,891

(22) Filed: Jun. 29, 2011

(65) Prior Publication Data

US 2012/0004224 A1 Jan. 5, 2012

Related U.S. Application Data

(63) Continuation of application No. 12/176,123, filed on Jul. 18, 2008, now abandoned, which is a continuation of application No. 10/857,458, filed on May 28, 2004, now Pat. No. 7,425, 553.

(60) Provisional application No. 60/474,741, filed on May 30, 2003.

(51) Int. Cl.
*A61K 31/535* (2006.01)
*A61K 31/44* (2006.01)
*A61K 31/42* (2006.01)
*A61K 31/40* (2006.01)
*A61K 31/49* (2006.01)
*C07D 209/14* (2006.01)

(52) U.S. Cl.
USPC .............. 514/235.2; 514/254.09; 514/414; 514/339; 514/378; 514/411; 548/466

(58) Field of Classification Search ............... 514/235.2, 514/254.09, 339, 411, 414, 378
See application file for complete search history.

(56) References Cited

U.S. PATENT DOCUMENTS

| | | | |
|---|---|---|---|
| 5,248,782 | A | 9/1993 | Haugland et al. |
| 5,338,854 | A | 8/1994 | Kang et al. |
| 5,573,909 | A | 11/1996 | Singer et al. |
| 5,691,334 | A | 11/1997 | Doria et al. |
| 6,071,947 | A | 6/2000 | D'Alessio et al. |
| 6,956,022 | B2 | 10/2005 | Tamura et al. |
| 7,425,553 | B2 * | 9/2008 | Attardo et al. ............ 514/235.2 |
| 2003/0215444 | A1 | 11/2003 | Elliott |
| 2005/0014802 | A1 | 1/2005 | Attardo et al. |
| 2005/0106148 | A1 | 5/2005 | Kay et al. |
| 2005/0267073 | A1 | 12/2005 | Dairi et al. |
| 2006/0035945 | A1 | 2/2006 | Attardo et al. |
| 2008/0051400 | A1 | 2/2008 | Viallet et al. |
| 2008/0076739 | A1 | 3/2008 | Viallet et al. |

FOREIGN PATENT DOCUMENTS

| | | |
|---|---|---|
| EP | 903 733 | 3/1999 |
| EP | 756 200 | 11/1999 |
| EP | 1644363 | 4/2006 |
| EP | 1853255 | 11/2007 |
| JP | 61034403 | 2/1986 |
| JP | 5-86374 | 12/1993 |
| JP | 08003136 | 1/1996 |
| JP | 10120562 | 5/1998 |
| JP | 10120563 | 5/1998 |
| JP | 2000275435 | 10/2000 |
| JP | 2001223081 | 8/2001 |
| JP | 2001223082 | 8/2001 |
| JP | 2001257077 | 9/2001 |
| JP | 2001297881 | 10/2001 |
| JP | 2001307884 | 11/2001 |
| JP | 2001330729 | 11/2001 |
| JP | 2001330730 | 11/2001 |
| WO | WO 93/09185 | 5/1993 |
| WO | WO 93/23492 | 11/1993 |
| WO | WO 98/40380 | 9/1998 |
| WO | WO 99/30709 | 6/1999 |
| WO | WO 00/24893 | 5/2000 |
| WO | WO 00/33836 | 6/2000 |
| WO | WO 01/55131 | 8/2001 |
| WO | WO 02/051409 | 7/2002 |
| WO | WO 03/008410 | 1/2003 |
| WO | WO 2004/014881 | 2/2004 |
| WO | WO 2004/106328 | 12/2004 |
| WO | WO 2005/117908 | 12/2005 |
| WO | WO 2006/089397 | 8/2006 |

OTHER PUBLICATIONS

Arnett et al., "The American Rheumatism Association 1987 Revised Criteria for the Classification of Rheumatoid Arthritis", Arthritis Rheum 31(3):315-324, 1988.
Baldino et al., "Indoloprodigiosins from the C-10 Bipyrrolic Precursor: New Antiproliferative Prodigiosin Analogs", Bioorg Med Chem Lett 16:701-704, 2006.
Beilstein Records No. 8747436, "2-(5-methoxy-1 H-indol-2-yl)-4-methoxy-5-<(5-undecyl-2H-pyrrol-2-ylidene) methyl>-2,2' -bi-IH-pyrrole hydrochloride", 2001.
Beilstein Records No. 8747419, "2-(5-chloro-1 H-indol-2-yl)-4-methoxy-5-<5-undecyl-2H-pyrrol-2-ylidene)methyl>-2,2' -bi-1H-pyrrole hydrochloride", 2001.
Beilstein Records No. 8746619 "2-(1H-indol-2-yl)-4-methoxy-5-<5-undecyl-2H-pyrrol-2-ylidene) methyl>-2,2'-bi-1 H-pyrrole hydrochloride", 2001.
Beilstein Records No. 8739149, "2-(5-methoxy-1 H-indol-2-yl)-4-methoxy-5-<5-undecyl-2H-pyrrol-2-ylidene)methyl>-2,2' -bi-1H-pyrrole", 2001.

(Continued)

*Primary Examiner* — Rebecca Anderson

(57) ABSTRACT

The present invention relates to novel Triheterocyclic Compounds, compositions comprising a Triheterocyclic Compound, and methods useful for treating or preventing cancer or a neoplastic disorder comprising administering a Triheterocyclic Compound. The compounds, compositions, and methods of the invention are also useful for inhibiting the growth of a cancer cell or neoplastic cell, treating or preventing a viral infection, or inhibiting the replication and/or infectivity of a virus.

3 Claims, 6 Drawing Sheets

OTHER PUBLICATIONS

Beilstein Records No. 8738700, "2-(5-chloro-1H-indol-2-yl)-4-methoxy-5-<5-undecyl-2H-pyrrol-2-ylidene)methyl>-2,2'-bi-1H-pyrrole", 2001.

Beilstein Records No. 8737177, "2-(1H-indol-2-yl)-4-methoxy-5-<5-undecyl-2H-pyrrol-2-ylidene) methyl>-2,2'-bi-1H-pyrrole", 2001.

Berge et al., "Pharmaceutical Salts", J Pharm Sci 66(1):1-19, 1977.

Bizhev et al., "Condensations of a pyrrole aldehyde with 1,2-diamines, to products with pharmacological and analytical interest," XP002297006 from STN Database Accession No. 1983:438416 abstract and the compound with the RN '86406-77-1!: "1H-pyrrole-2, 4-dcarboxylic acid, 5-(IH-benzimidazol-2-yl)-3-methyl-, diethyl ester", Farmatsiya (Sofia, Bulgaria) 33(1): 1-6, 1983.

Boger, "Total Synthesis of Prodigiosin, Prodigiosene, and Desmethoxyprodigiosin: Diels-Alder Reactions of Heterocyclic Azadienes and Development of an Effective Palladium(II)-Promoted 2,2'-Bipyrrole Coupling Procedure", J Org Chem 53:1405-1415, 1988.

Burmester et al., "Mononuclear Phagocytes and Rheumatoid Synovitis", Arthritis Rheum 40(1):5-18, 1997.

Chem, "Syntheses of 1, 2-Bis '5-(2'-Benzoxazolyl)-Pyrrole-2-Y1) Ethenes", XP002297005 from STN Database Accession No. 1995:766242 Abstract and the Compound with the RN 168002-55-9!: "IH-Pyrrole-2-Carboxylic Acid, 5-(2-Benzoxazolvl)-3-Methyl, Ethyl Ester", Dyes and Pigments 28(4):291-295, 1995.

D'Alessio et al., "Synthesis and Immunosuppressive Activity of Novel Prodigiosin Derivatives", J Med Chem 43(3):2557-2565, 2000.

D'Alessio and Rossi, "Short Synthesis of Undecylprodigiosine. A New Route to 2,2'-Bipyrrolyl-Pyrromethene Systems", Synlett 513-514, 1996.

Derwent Chemical Registry Resource Accession No. DCR-214226, 2003.

Developmental Therapeutics Program of the NCIINIH website, Aug. 2000.

Firestein and Zvaifler, "How Important Are T Cells in Chronic Rheumatoid Synovitis?", Arthritis Rheum 33(6):768-773, 1990.

Fürstner, "Chemistry and Biology of Roseophilin and the Prodigiosin Alkaloids: A Survey of the Last 2500 Years", Angew Chem Int Ed 42:3582-3603, 2003.

Goronzy and Weyand, "T Cells in Rheumatoid Arthritis. Paradigms and Facts", Rheum Dis Clin North Am 21(3):655-74, 1995.

Manderville, "Synthesis, Proton-Affinity and Anti-Cancer Properties of the Prodigiosin-Group Natural Products", Curr Med Chem—Anti-Cancer Agents 1:195-218, 2001.

Martinez et al., "Preparation and Lithiation of N-(N,N-Dimethylamino)Pyrrole: A Useful Reagent for the Preparation of 2-Acylpyrroles", J Org Chem 46:3760-3761, 1981.

Minato et al., "Palladium-Phosphine Complex Catalyzed Cross-Coupling Reaction of 1-Methyl-2Pyrrolyl-Magnesium Bromide and -Zinc Chloride with Organic Halides", Tetrahedron Lett 22(52):5319-5322, 1981.

Nicolaou et al., "Phosphate Prodrugs for Amines Utilizing a Fast Intramolecular Hydroxy Amide Lactonization", J Org Chem 61:8636-8641, 1996.

Panayi et al., "The Importance of the T Cell in Initiating and Maintaining the Chronic Synovitis of Rheumatoid Arthritis", Arthritis Rheum 35(7):729-735, 1992.

Rapoport and Holden, "The Synthesis of Prodigiosin", J Am Chem Soc 84:635-642, 1962.

Todd et al., "A Molecular Basis for MHC Class II—Associated Autoimmunity", Science 240:1003-1009, 1988.

Zhu et al., "Phosphate Prodrugs of PDI54075", Bioorganic & Med Chem Lett, Oxford, OB 10(0):1121-1124, 2000.

Office Action mailed May 23, 2007 in connection with U.S. Appl. No. 10/857,458, assigned to Gemin X Pharmaceuticals Canada Inc.

Claims pending on May 23, 2007 in connection with U.S. Appl. No. 10/857,458, assigned to Gemin X Pharmaceuticals Canada Inc.

Office Action mailed Mar. 4, 2008 in connection with U.S. Appl. No. 10/857,458, assigned to Gemin X Pharmaceuticals Canada Inc.

Claims pending on Mar. 4, 2008 in connection with U.S. Appl. No. 10/857,458, assigned to Gemin X Pharmaceuticals Canada Inc.

L. Bonapace, et al., "The BH3 mimetic obatoclax overcomes glucocorticoid-resistance by activating autophagic cell death," *16th European Cell Death Organization (ECDO) Conference on Apoptosis*, Sep. 6-9, 2008, abstract SO-2.

A. Chiappori et al., "Obatoclax (GX15-070), a Small Molecule pan-Bcl-2 Inhibitor, in Combination with Docetaxel in a Phase I/II Trial Enrolling Patients with Relapsed Non-Small Lung Cancer (NSCLC)," *Poster presentation at 20th EROTC-NCI-AACR Symosium on Molecular Targets and Cancer Therapeutics in Geneva*, Oct. 21-24, 2008.

A. Chiappori, et al., "A Phase Ib Trial of Bcl-2 Inhibitor Obatoclax in Combination with Carboplatin and Etoposide for Previously Untreated Patients with Extensive-Stage Small Cell Lung Cancer (ES-SCLC)," *Poster presentation at the 2009 ASCO (American Society of Clinical Oncology) Annual Meeting* in Orlando, FL., USA, May 29-Jun. 2, 2009.

S. M. O'Brien, et al., "Phase I study of obatoclax mesylate (GX15-070), a small molecule pan-Bcl-2 family antagonist, in patients with advanced chronic lymphocytic leukemia," *Blood*, 113: 299-305 (2009).

A.D. Schimmer, et al., "A phase I trial of the small molecule pan-Bcl-2 family inhibitor obatoclax mesylate (GX15-070) administered by continuous infusion for up to four days to patients with hematological malignancies," *ASH Annual Meeting Abstracts*, 110, abstract 892 (2007).

* cited by examiner

TRIHETEROCYCLIC COMPOUNDS AND COMPOSITIONS THEREOF

RELATED APPLICATIONS

This application is a continuation of U.S. patent application Ser. No. 12/176,123, filed Jul. 18, 2008 now abandoned, which is a continuation of U.S. patent application Ser. No. 10/857,458, filed May 28, 2004, now U.S. Pat. No. 7,425,553. which claims the benefit of U.S. Provisional Application No. 60/474,741, filed May 30, 2003, each of which is incorporated by reference herein in its entirety.

1. FIELD OF THE INVENTION

The present invention relates to Triheterocyclic Compounds, compositions comprising a Triheterocyclic Compound, and methods useful for treating or preventing cancer or a neoplastic disorder comprising administering an effective amount of a Triheterocyclic Compound. The compounds, compositions, and methods of the invention are also useful for treating or preventing cancer or neoplastic disease, or inhibiting the growth of a cancer cell or neoplastic cell, treating or preventing a viral infection, or inhibiting the replication or infectivity of a virus.

2. BACKGROUND OF THE INVENTION

2.1 Cancer and Neoplastic Disease

Cancer affects approximately 20 million adults and children worldwide, and this year, more than 9 million new cases will be diagnosed (International Agency for Research on Cancer; www.irac.fr). According to the American Cancer Society, about 563,100 Americans are expected to die of cancer this year, more than 1500 people a day. Since 1990, in the United States alone, nearly five million lives have been lost to cancer, and approximately 12 million new cases have been diagnosed.

Currently, cancer therapy involves surgery, chemotherapy and/or radiation treatment to eradicate neoplastic cells in a patient (see, for example, Stockdale, 1998, "Principles of Cancer Patient Management", in *Scientific American: Medicine*, vol. 3, Rubenstein and Federman, eds., Chapter 12, Section IV). All of these approaches pose significant drawbacks for the patient. Surgery, for example, may be contraindicated due to the health of the patient or may be unacceptable to the patient. Additionally, surgery may not completely remove the neoplastic tissue. Radiation therapy is effective only when the irradiated neoplastic tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, chemotherapy has many drawbacks (see, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, many tumor cells are resistant or develop resistance to chemotherapeutic agents through multidrug resistance.

Tamura et al., JP93086374, discloses metacycloprodigiosin and/or prodigiosin-25C as being useful for treating leukemia, but provides data for only prodigiosin-25C activity against L-5178Y cells in vitro. Hirata et al., JP-10120562, discloses the use of cycloprodigiosin as an inhibitor of the vacuolar ATPase proton pump and states that cycloprodigiosin may have anti-tumor enhancing activity. Hirata et al., JP-10120563 discloses the use of cycloprodigiosin as a therapeutic drug for leukemia, as an immunosuppressant, and as an apoptosis inducer. JP61034403, to Kirin Brewery Co. Ltd, describes prodigiosin for increasing the survival time of mice with leukemia. Boger, 1988, J. Org. Chem. 53:1405-1415 discloses in vitro cytotoxic activity of prodigiosin, prodigiosene, and 2-methyl-3-pentylprodigiosene against mouse P388 leukemia cells. The National Cancer Institute, (see the website of the Developmental Therapeutics Program of the NCI/NIH), discloses data obtained from the results of a human-tumor-cell-line screen, including screening of butyl-cycloheptyl-prodiginine HCl; however, the screen provides no indication that the compounds of the screen are selective for cancer cells (e.g., as compared to normal cells).

Therefore, there is a significant need in the art for novel compounds and compositions, and methods that are useful for treating cancer or neoplastic disease with reduced or without the aforementioned side effects. Further, there is a need for cancer treatments that provide cancer-cell-specific therapies with increased specificity and decreased toxicity.

2.2 Viruses and Disease

In addition to cancer, an enormous number of human and animal diseases result from virulent and opportunistic viral infections (see Belshe (Ed.) 1984 *Textbook of Human Virology*, PSG Publishing, Littleton, Mass.). Viral diseases of a wide array of tissues, including the respiratory tract, CNS, skin, genitourinary tract, eyes, ears, immune system, gastrointestinal tract, and musculoskeletal system, affect a vast number of humans of all ages (see Table 328-2 In: Wyngaarden and Smith, 1988, *Cecil Textbook of Medicine*, 18$^{th}$ Ed., W.B. Saunders Co., Philadelphia, pp. 1750-1753).

Although considerable effort has been invested in the design of effective anti-viral therapies, viral infections continue to threaten the lives of millions of people worldwide. In general, attempts to develop anti-viral drugs have focused on several stages of viral life cycle (See e.g., Mitsuya, H., et al., 1991, FASEB J. 5:2369-2381, discussing HIV). However, a common drawback associated with using of many current anti-viral drugs is their deleterious side effects, such as toxicity to the host or resistance by certain viral strains.

Accordingly, there is a need in the art for anti-viral compounds, compositions, and methods that allow for safe and effective treatment of viral disease without the above-mentioned disadvantages.

Citation or identification of any reference in Section 2 of this application is not an admission that such reference is available as prior art to the present invention.

3. SUMMARY OF THE INVENTION

The present invention encompasses compounds having the Formula (Ia):

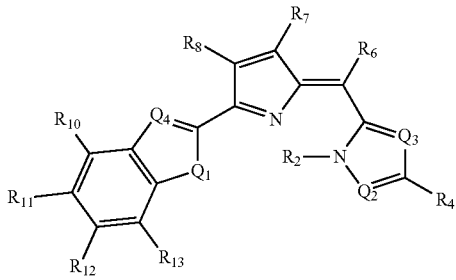

(Ia)

and pharmaceutically acceptable salts thereof, wherein:

$Q_1$ is —O—, —S— or —N($R_1$)—

$Q_2$ is —C($R_3$)— or —N—;

$Q_3$ is —C($R_5$)— or —N—;

$Q_4$ is —C($R_9$)— or —N—;

$R_1$ is —$Y_m$($R_a$), wherein —$R_a$ is —H, —OH, —$C_1$-$C_8$ alkyl, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —O($CH_2$)$_n OR_{14}$, —C(O)$R_{14}$, —O—C(O) $R_{14}$, —C(O)($CH_2$)$_n$—$R_{14}$, —O—C(O)$OR_{14}$, —O—C(O) $NHR_{14}$, —O—C(O)N($R_{14}$)$_2$, —C(O)N($R_{14}$)$_2$, —C(O)$OR_{14}$, —C(O)$NHR_{14}$, —S—$R_{14}$, —$SOR_{14}$, —S(O)$_2 R_{14}$, —NHC(O)$R_{14}$, —$NHSR_{14}$, —$NHSOR_{14}$, —NHS(O)$_2 R_{14}$, —OS(O)$_2$O$^-$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, or —$NR_{14}$C(S)N($R_{14}$)$_2$, $R_2$ is —H, —$C_1$-$C_8$ alkyl or —OH;

$R_3$, $R_4$, and $R_5$ are independently —$Y_m$($R_b$), wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —O($CH_2$)$_n OR_{14}$, —C(O)$R_{14}$, —O—C(O)$R_{14}$, —C(O)($CH_2$), —$R_{14}$, —O—C(O)$OR_{14}$, —O—C(O)$NHR_{14}$, —O—C(O)N($R_{14}$)$_2$, —C(O)N($R_{14}$)$_2$, —C(O)$OR_{14}$, —C(O)$NHR_{14}$, —S—$R_{14}$, —$SOR_{14}$, —S(O)$_2 R_{14}$, —NHC(O)$R_{14}$, —$NHSR_{14}$, —$NHSOR_{14}$, —NHS(O)$_2 R_{14}$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, —$NR_{14}$C(S)N($R_{14}$)$_2$ or $R_3$ and $R_4$, or $R_4$ and $R_5$, together with the carbon atom to which each is attached, join to form a 5- to 9-membered ring, with the proviso that if $Q_3$ is —C($R_5$)— and m=0, then $R_5$ is not H;

$R_6$ is —H, halogen, —OH, —$NH_2$, —$C_1$-$C_8$ alkyl, or —O—($C_1$-$C_8$ alkyl);

$R_7$ is —$Y_m$—($R_c$), wherein —$R_c$ is —$C_1$-$C_8$ alkyl, —O—($C_1$-$C_8$ alkyl), —O-benzyl, —OH, —$NH_2$, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —$NO_2$, —$N_3$, —$C_2$-$C_8$ alkynyl, —$OR_{14}$, —O($CH_2$)$_n R_{14}$, —C(O)$R_{14}$, —O—C(O)$R_{14}$, —C(O)($CH_2$)$_n$—$R_{14}$, —O—C(O)$OR_{14}$, —O—C(O)$NHR_{14}$, —O—C(O)N($R_{14}$)$_2$, —C(O)N($R_{14}$)$_2$, —C(O)$OR_{14}$, —C(O)$NHR_{14}$, —S—$R_{14}$, —$SOR_{14}$, —S(O)$_2 R_{14}$, —NHC(O)$R_{14}$, —$NHSR_{14}$, —$NHSOR_{14}$, —NHS(O)$_2 R_{14}$, —O($CH_2$)$_n$C(O)O($CH_2$)$_n CH_3$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, —$NR_{14}$C(S)N($R_{14}$)$_2$;

$R_8$ is —$Y_m$($R_4$), wherein —$R_d$ is —H, —OH, halogen, amino, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, cycloalkyl, -phenyl, -naphthyl, -3- to 9-membered heterocycle, —$OR_{14}$, —O($CH_2$)$_n OR_{14}$, —C(O)$R_{14}$, —O—C(O) $R_{14}$, —C(O)($CH_2$)$_n$—$R_{14}$, —O—C(O)$OR_{14}$, —O—C(O) $NHR_{14}$, —O—C(O)N($R_{14}$)$_2$, —C(O)N($R_{14}$)$_2$, —C(O)$OR_{14}$, —C(O)$NHR_{14}$, —S—$R_{14}$, —$SOR_{14}$, —S(O)$_2 R_{14}$, —NHC(O)$R_{14}$, —$NHSR_{14}$, —$NHSOR_{14}$, —NHS(O)$_2 R_{14}$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, —$NR_{14}$C(S)N($R_{14}$)$_2$;

$R_9$, $R_{10}$, $R_{11}$, $R_{12}$, and $R_{13}$ are independently —$Y_m$($R_e$), wherein —$R_e$ is —H, halogen, —$NH_2$, $C_1$-$C_8$ alkyl, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —C(O)NH($C_1$-$C_5$ alkyl), —C(O)N($C_1$-$C_5$ alkyl)$_2$, —NHC(O)($C_1$-$C_5$ alkyl), —NHC(=$NH_2^+$)$NH_2$, —CN, —$NO_2$, $N_3$, -3- to 9-membered heterocycle, —$OR_{14}$, —O($CH_2$)$_n OR_{14}$, —C(O)$R_{14}$, —O—C(O)$R_{14}$, —C(O)($CH_2$)$_n$—$R_{14}$, —O—C(O)$OR_{14}$, —O—C(O)$NHR_{14}$, —O—C(O)N($R_{14}$)$_2$, —C(O)N($R_{14}$)$_2$, —C(O)$OR_{14}$, —C(O)$NHR_{14}$, —S—$R_{14}$, —$SOR_{14}$, —S(O)$_2 R_{14}$, —NHC(O)$R_{14}$, —$NHSR_{14}$, —$NHSOR_{14}$, —NHS(O)$_2 R_{14}$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, —$NR_{14}$C(S)N($R_{14}$)$_2$ or $R_{11}$ and $R_{12}$, together with the carbon atom to which each is attached, join to form a 5- to 9-membered heterocycle;

each $R_{14}$ is independently —H, —$C_1$-$C_8$ alkyl, —$C_3$-$C_{12}$ cycloalkyl, -phenyl, -naphthyl, -3- to 9-membered heterocycle, —$C_2$-$C_8$ alkenyl, or —$C_2$-$C_8$ alkynyl;

each Y is independently —$C_1$-$C_8$ alkylene-, —$C_2$-$C_8$ alkenylene- or —$C_2$-$C_8$ alkynylene-;

each m is independently 0 or 1; and each n is independently an integer ranging from 0 to 6.

In certain specific embodiments, —O-benzyl is unsubstituted.

In certain specific embodiments, $R_7$ is 3-methoxy benzyloxy.

In certain specific embodiments, -phenyl is unsubstituted.

In certain specific embodiments, $R_{14}$ is phenyl dimethyl-amine. In even more specific embodiments, $R_1$ is C(O)$NHR_{14}$ and $R_{14}$ is phenyl dimethyl-amine.

In certain specific embodiments $R_7$ is —$OCH_2$C(O)$OC_2H_5$.

In certain specific embodiments, $R_{14}$ is benzyloxy phenyl. In even more specific embodiments, $R_1$ is C(O)$NHR_{14}$ and $R_{14}$ is benzyloxy phenyl.

In certain specific embodiments, $R_{14}$ is para-bromo-phenyl. In even more specific embodiments, $R_1$ is —C(O)$R_{14}$ and $R_{14}$ is para-bromo-phenyl.

In certain specific embodiments, $R_a$ is para-hydroxy-phenyl. In even more specific embodiments, $Y_m$ is —$CH_2$— and $R_{14}$ is para-hydroxy-phenyl.

In certain specific embodiments, $R_7$ is —NH(phenyl)$OCH_3$.

In certain specific embodiments $R_1$ is —($CH_2$)$_2$OS(O)$_2$O$^-$.

In certain specific embodiments, $R_{11}$ and $R_{12}$ are not joined together with the carbon atom to which each is attached.

The invention further provides compositions comprising a pharmaceutically acceptable carrier or vehicle and an effective amount of a compound having the Formula (Ia):

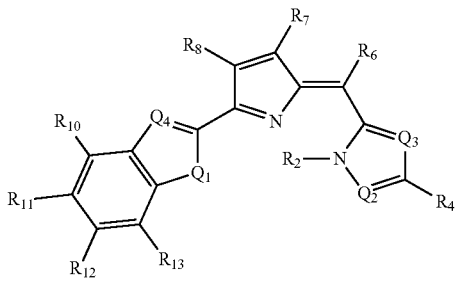

(Ia)

and pharmaceutically acceptable salts thereof, wherein:

$Q_1$ is —O—, —S— or —N($R_1$)—

$Q_2$ is —C($R_3$)— or —N—;

$Q_3$ is —C($R_5$)— or —N—;

$Q_4$ is —C($R_9$)— or —N—;

$R_1$ is —$Y_m$($R_a$), wherein —$R_a$ is —H, —OH, —$C_1$-$C_8$ alkyl, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —O($CH_2$)$_n$$OR_{14}$, —C(O)$R_{14}$, —O—C(O)$R_{14}$, —C(O)($CH_2$)$_n$—$R_{14}$, —O—C(O)$OR_{14}$, —O—C(O)$NHR_{14}$, —O—C(O)N($R_{14}$)$_2$, —C(O)N($R_{14}$)$_2$, —C(O)$OR_{14}$, —C(O)$NHR_{14}$, —S—$R_{14}$, —$SOR_{14}$, —S(O)$_2$$R_{14}$, —NHC(O)$R_{14}$, —$NHSR_{14}$, —$NHSOR_{14}$, —NHS(O)$_2$$R_{14}$, —OS(O)$_2$O$^-$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, or —$NR_{14}$C(S)N($R_{14}$)$_2$;

$R_2$ is —H, —$C_1$-$C_8$ alkyl or —OH;

$R_3$, $R_4$, and $R_5$ are independently —$Y_m$($R_b$), wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —O($CH_2$)$_n$$OR_{14}$, —C(O)$R_{14}$, —O—C(O)$R_{14}$, —C(O)($CH_2$)$_n$—$R_{14}$, —O—C(O)$OR_{14}$, —O—C(O)$NHR_{14}$, —O—C(O)N($R_{14}$)$_2$, —C(O)N($R_{14}$)$_2$, —C(O)$OR_{14}$, —C(O)$NHR_{14}$, —S—$R_{14}$, —$SOR_{14}$, —S(O)$_2$$R_{14}$, —NHC(O)$R_{14}$, —$NHSR_{14}$, —$NHSOR_{14}$, —NHS(O)$_2$$R_{14}$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, —$NR_{14}$C(S)N($R_{14}$)$_2$ or $R_3$ and $R_4$, or $R_4$ and $R_5$, together with the carbon atom to which each is attached, join to form a 5- to 9-membered ring, with the proviso that if $Q_3$ is —C($R_5$)— and m=0, then $R_5$ is not H;

$R_6$ is —H, halogen, —OH, —$NH_2$, —$C_1$-$C_8$ alkyl, or —O—($C_1$-$C_8$ alkyl);

$R_7$ is —$Y_m$($R_c$), wherein —$R_c$ is —$C_1$-$C_8$ alkyl, —O—($C_1$-$C_8$ alkyl), —O-benzyl, —OH, —$NH_2$, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —$NO_2$, —$N_3$, —$C_2$-$C_8$ alkynyl, —$OR_{14}$, —O($CH_2$)$_n$$OR_{14}$, —C(O)$R_{14}$, —O—C(O)$R_{14}$, —C(O)($CH_2$)$_n$—$R_{14}$, —O—C(O)$OR_{14}$, —O—C(O)$NHR_{14}$, —O—C(O)N($R_{14}$)$_2$, —C(O)N($R_{14}$)$_2$, —C(O)$OR_{14}$, —C(O)$NHR_{14}$, —$SOR_{14}$, —S(O)$_2$$R_{14}$, —NHC(O)$R_{14}$, —$NHSR_{14}$, —$NHSOR_{14}$, —NHS(O)$_2$$R_{14}$, —O($CH_2$)$_n$C(O)O($CH_2$)$_n$$CH_3$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, —$NR_{14}$C(S)N($R_{14}$)$_2$;

$R_8$ is —$Y_m$($R_d$), wherein —$R_d$ is —H, —OH, halogen, amino, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —O($CH_2$)$_n$$OR_{14}$, —C(O)$R_{14}$, —O—C(O)$R_{14}$, —C(O)($CH_2$)$_n$—$R_{14}$, —O—C(O)$OR_{14}$, —O—C(O)$NHR_{14}$, —O—C(O)N($R_{14}$)$_2$, —C(O)N($R_{14}$)$_2$, —C(O)$OR_{14}$, —C(O)$NHR_{14}$, —S—$R_{14}$, —$SOR_{14}$, —S(O)$_2$$R_{14}$, —NHC(O)$R_{14}$, —$NHSR_{14}$, —$NHSOR_{14}$, —NHS(O)$_2$$R_{14}$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, —$NR_{14}$C(S)N($R_{14}$)$_2$;

$R_9$, $R_{10}$, $R_{11}$, $R_{12}$, and $R_{13}$ are independently —$Y_m$($R_e$), wherein —$R_e$ is —H, halogen, —$NH_2$, $C_1$-$C_8$ alkyl, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —C(O)NH($C_1$-$C_5$ alkyl), —C(O)N($C_1$-$C_5$ alkyl)$_2$, —NHC(O)($C_1$-$C_5$ alkyl), —NHC(=$NH_2^+$)$NH_2$, —CN, —$NO_2$, $N_3$, -3- to 9-membered heterocycle, —$OR_{14}$, —O($CH_2$)$_n$$OR_{14}$, —C(O)$R_{14}$, —O—C(O)$R_{14}$, —C(O)($CH_2$)$_n$—$R_{14}$, —O—C(O)$OR_{14}$, —O—C(O)$NHR_{14}$, —O—C(O)N($R_{14}$)$_2$, —C(O)N($R_{14}$)$_2$, —C(O)$OR_{14}$, —C(O)$NHR_{14}$, —S(O)$_2$$R_{14}$, —NHC(O)$R_{14}$, —$NHSR_{14}$, —$NHSOR_{14}$, —NHS(O)$_2$$R_{14}$, O—C(S)$R_{14}$, O—C(S)$OR_{14}$, O—C(S)$NHR_{14}$, O—C(S)N($R_{14}$)$_2$, —C(S)$OR_{14}$, —C(S)$NHR_{14}$, —C(S)N($R_{14}$)$_2$, —NHC(S)$R_{14}$, —$NR_{14}$C(S)$R_{14}$, —NHC(S)$NHR_{14}$, —NHC(S)N($R_{14}$)$_2$, —$NR_{14}$C(S)$NHR_{14}$, —$NR_{14}$C(S)N($R_{14}$)$_2$ or $R_{11}$ and $R_{12}$, together with the carbon atom to which each is attached, join to form a 5- to 9-membered heterocycle;

each $R_{14}$ is independently —H, —$C_1$-$C_8$ alkyl, —$C_3$-$C_{12}$ cycloalkyl, -phenyl, -naphthyl, -3- to 9-membered heterocycle, —$C_2$-$C_8$ alkenyl, or —$C_2$-$C_8$ alkynyl;

each Y is independently —$C_1$-$C_8$ alkylene-, —$C_2$-$C_8$ alkenylene- or —$C_2$-$C_8$ alkynylene-;

each m is independently 0 or 1; and each n is independently an integer ranging from 0 to 6.

In certain specific embodiments, —O-benzyl is unsubstituted.

In certain specific embodiments, $R_7$ is 3-methoxy benzyloxy.

In certain specific embodiments, -phenyl is unsubstituted.

In certain specific embodiments, $R_{14}$ is phenyl dimethyl-amine. In even more specific embodiments, $R_1$ is C(O)$NHR_{14}$ and $R_{14}$ is phenyl dimethyl-amine.

In certain specific embodiments $R_7$ is —$OCH_2$C(O)$OC_2H_5$.

In certain specific embodiments, $R_{14}$ is benzyloxy phenyl. In even more specific embodiments, $R_1$ is C(O)$NHR_{14}$ and $R_{14}$ is benzyloxy phenyl.

In certain specific embodiments, $R_{14}$ is para-bromo-phenyl. In even more specific embodiments, $R_1$ is —C(O)$R_{14}$ and $R_{14}$ is para-bromo-phenyl.

In certain specific embodiments, $R_a$ is para-hydroxy-phenyl. In even more specific embodiments, $Y_m$ is —$CH_2$— and $R_{14}$ is para-hydroxy-phenyl.

In certain specific embodiments, $R_7$ is —NH(phenyl)$OCH_3$.

In certain specific embodiments $R_1$ is —($CH_2$)$_2$OS(O)$_2$O$^-$.

In certain specific embodiments, $R_{11}$ and $R_{12}$ are not joined together with the carbon atom to which each is attached.

In another aspect, the invention provides methods for treating cancer in a patient, comprising administering to a patient in need thereof an effective amount of a compound or a pharmaceutically acceptable salt of the compound having the Formula (Ia), depicted above, wherein $Q_1$-$Q_4$, $R_2$, $R_4$, $R_6$-$R_8$ and $R_{10}$-$R_{13}$ are defined above for the compounds of formula (Ia).

In still another aspect, the invention provides methods for treating a virus or a viral infection in a patient, comprising administering to a patient in need thereof an effective amount of a compound or a pharmaceutically acceptable salt of the compound having the Formula (Ia), depicted above, wherein $Q_1$-$Q_4$, $R_2$, $R_4$, $R_6$-$R_8$ and $R_{10}$-$R_{13}$ are defined above for the compounds of formula (Ia).

In a further aspect, the present invention relates to methods useful for making the Triheterocyclic Compounds having the Formula (Ia).

In one embodiment, the invention provides a method for making a compound having the Formula (Ia):

(Ia)

comprising contacting a compound of Formula (II)

(II)

with a compound of Formula (iv)

(iv)

in the presence of an organic solvent and a protic acid, for a time and at a temperature sufficient to make the compound of Formula (Ia),
wherein
  $Q_1$ is —O—, —S— or —N($R_1$)—
  $Q_2$ is —C($R_3$)— or —N—;
  $Q_3$ is —C($R_5$)— or —N—;
  $Q_4$ is —C($R_9$)— or —N—;
  $R_1$ is —$Y_m$($R_a$), wherein —$R_a$ is —H, —OH, —$C_1$-$C_8$ alkyl, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —O($CH_2$)$_n OR_{14}$, —C(O)$R_{14}$, —O—C(O)$R_{14}$, —C(O)($CH_2$)$_n$—$R_{14}$, —O—C(O)$OR_{14}$, —O—C(O)NH$R_{14}$, —O—C(O)N($R_{14}$)$_2$, —C(O)N($R_{14}$)$_2$, —C(O)$OR_{14}$, —C(O)NH$R_{14}$, —S—$R_{14}$, —SO$R_{14}$, —S(O)$_2 R_{14}$, —NHC(O)$R_{14}$, —NHS$R_{14}$, —NHSO$R_{14}$, —NHS(O)$_2 R_{14}$, —OS(O)$_2$O$^-$, O—C(S)$OR_{14}$, O—C(S)$OR_{14}$, O—C(S)NH$R_{14}$, O—C(S)N($R_{14}$)$_2$, —C(S)$OR_{14}$, —C(S)NH$R_{14}$, —C(S)N($R_{14}$)$_2$, —NHC(S)$R_{14}$, —NR$_{14}$C(S)$R_{14}$, —NHC(S)NH$R_{14}$, —NHC(S)N($R_{14}$)$_2$, —NR$_{14}$C(S)NH$R_{14}$, or —NR$_{14}$C(S)N($R_{14}$)$_2$;

$R_2$ is —H, —$C_1$-$C_8$ alkyl or —OH;

$R_3$, $R_4$, and $R_5$ are independently —$Y_m$($R_b$), wherein $R_b$ is —H, halogen, —NH$_2$, —CN, —NO$_2$, —SH, —N$_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —O($CH_2$)$_n OR_{14}$, —C(O)$R_{14}$, —O—C(O)$R_{14}$, —C(O)($CH_2$)$_n$—$R_{14}$, —O—C(O)$OR_{14}$, —O—C(O)NH$R_{14}$, —O—C(O)N($R_{14}$)$_2$, —C(O)N($R_{14}$)$_2$, —C(O)$OR_{14}$, —C(O)NH$R_{14}$, —S—$R_{14}$, —SO$R_{14}$, —S(O)$_2 R_{14}$, —NHC(O)$R_{14}$, —NHS$R_{14}$, —NHSO$R_{14}$, —NHS(O)$_2 R_{14}$, O—C(S)$R_{14}$, O—C(S)$OR_{14}$, O—C(S)NH$R_{14}$, O—C(S)N($R_{14}$)$_2$, —C(S)$OR_{14}$, —C(S)NH$R_{14}$, —C(S)N($R_{14}$)$_2$, —NHC(S)$R_{14}$, —NR$_{14}$C(S)$R_{14}$, —NHC(S)NH$R_{14}$, —NHC(S)N($R_{14}$)$_2$, —NR$_{14}$C(S)NH$R_{14}$, —NR$_{14}$C(S)N($R_{14}$)$_2$ or $R_3$ and $R_4$, or $R_4$ and $R_5$, together with the carbon atom to which each is attached, join to form a 5- to 9-membered ring, with the proviso that if $Q_3$ is —C($R_5$)— and m=0, then $R_5$ is not H;

$R_6$ is —H, halogen, —OH, —NH$_2$, —$C_1$-$C_8$ alkyl, or —O—($C_1$-$C_8$ alkyl);

$R_7$ is —$Y_m$—($R_c$), wherein —$R_c$ is —$C_1$-$C_8$ alkyl, —O—($C_1$-$C_8$ alkyl), —O-benzyl, —OH, —NH$_2$, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —NO$_2$, —N$_3$, —$C_2$-$C_8$ alkynyl, —$OR_{14}$, —O($CH_2$)$_n OR_{14}$, —C(O)$R_{14}$, —O—C(O)$R_{14}$, —C(O)($CH_2$)$_n$—$R_{14}$, —O—C(O)$OR_{14}$, —O—C(O)NH$R_{14}$, —O—C(O)N($R_{14}$)$_2$, —C(O)N($R_{14}$)$_2$, —C(O)$OR_{14}$, —C(O)NH$R_{14}$, —S—$R_{14}$, —SO$R_{14}$, —S(O)$_2 R_{14}$, —NHC(O)$R_{14}$, —NHS$R_{14}$, —NHSO$R_{14}$, —NHS(O)$_2 R_{14}$, —O($CH_2$)$_n$C(O)O($CH_2$)$_n CH_3$, O—C(S)$R_{14}$, O—C(S)$OR_{14}$, O—C(S)NH$R_{14}$, O—C(S)N($R_{14}$)$_2$, —C(S)$OR_{14}$, —C(S)NH$R_{14}$, —C(S)N($R_{14}$)$_2$, —NHC(S)$R_{14}$, —NR$_{14}$C(S)$R_{14}$, —NHC(S)NH$R_{14}$, —NHC(S)N($R_{14}$)$_2$, —NR$_{14}$C(S)NH$R_{14}$, —NR$_{14}$C(S)N($R_{14}$)$_2$;

$R_8$ is —$Y_m$($R_d$), wherein —$R_d$ is —H, —OH, halogen, amino, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —NO$_2$, —N$_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —O($CH_2$)$_n OR_{14}$, —C(O)$R_{14}$, —O—C(O)$R_{14}$, —C(O)($CH_2$)$_n$—$R_{14}$, —O—C(O)$OR_{14}$, —O—C(O)NH$R_{14}$, —O—C(O)N($R_{14}$)$_2$, —C(O)N($R_{14}$)$_2$, —C(O)$OR_{14}$, —C(O)NH$R_{14}$, —S—$R_{14}$, —SO$R_{14}$, —S(O)$_2 R_{14}$, —NHC(O)$R_{14}$, —NHS$R_{14}$, —NHSO$R_{14}$, —NHS(O)$_2 R_{14}$, O—C(S)$R_{14}$, O—C(S)$OR_{14}$, O—C(S)NH$R_{14}$, O—C(S)N($R_{14}$)$_2$, —C(S)$OR_{14}$, —C(S)NH$R_{14}$, —C(S)N($R_{14}$)$_2$, —NHC(S)$R_{14}$, —NR$_{14}$C(S)$R_{14}$, —NHC(S)NH$R_{14}$, —NHC(S)N($R_{14}$)$_2$, —NR$_{14}$C(S)NH$R_{14}$, —NR$_{14}$C(S)N($R_{14}$)$_2$;

$R_9$, $R_{10}$, $R_{11}$, $R_{12}$, and $R_{13}$ are independently —$Y_m$($R_e$), wherein —$R_e$ is —H, halogen, —NH$_2$, $C_1$-$C_8$ alkyl, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —C(O)NH($C_1$-$C_5$ alkyl), —C(O)N($C_1$-$C_5$ alkyl)$_2$, —NHC(O)($C_1$-$C_5$ alkyl), —NHC(=NH$_2^+$)NH$_2$, —CN, —NO$_2$, N$_3$, -3- to 9-membered heterocycle, —OR$_{14}$, —O(CH$_2$)$_n$OR$_{14}$, —C(O)R$_{14}$, —O—C(O)R$_{14}$, —C(O)(CH$_2$)$_n$—R$_{14}$, —O—C(O)OR$_{14}$, —O—C(O)NHR$_{14}$, —O—C(O)N(R$_{14}$)$_2$, —C(O)N(R$_{14}$)$_2$, —C(O)OR$_{14}$, —C(O)NHR$_{14}$, —S—R$_{14}$, —SOR$_{14}$, —S(O)$_2$R$_{14}$, —NHC(O)R$_{14}$, —NHSR$_{14}$, —NHSOR$_{14}$, —NHS(O)$_2$R$_{14}$, O—C(S)R$_{14}$, O—C(S)OR$_{14}$, O—C(S)NHR$_{14}$, O—C(S)N(R$_{14}$)$_2$, —C(S)OR$_{14}$, —C(S)NHR$_{14}$, —C(S)N(R$_{14}$)$_2$, —NHC(S)R$_{14}$, —NR$_{14}$C(S)R$_{14}$, —NHC(S)NHR$_{14}$, —NHC(S)N(R$_{14}$)$_2$, —NR$_{14}$C(S)NHR$_{14}$, —NR$_{14}$C(S)N(R$_{14}$)$_2$ or R$_{11}$ and R$_{12}$, together with the carbon atom to which each is attached, join to form a 5- to 9-membered heterocycle;

each R$_{14}$ is independently —H, —C$_1$-C$_8$ alkyl, —C$_3$-C$_{12}$ cycloalkyl, -phenyl, -naphthyl, -3- to 9-membered heterocycle, —C$_2$-C$_8$ alkenyl, or —C$_2$-C$_8$ alkynyl;

each Y is independently —C$_1$-C$_8$ alkylene-, —C$_2$-C$_8$ alkenylene- or —C$_2$-C$_8$ alkynylene-;

each m is independently 0 or 1; and each n is independently an integer ranging from 0 to 6.

In certain specific embodiments, —O-benzyl is unsubstituted.

In certain specific embodiments, R$_7$ is 3-methoxy benzyloxy.

In certain specific embodiments, -phenyl is unsubstituted.

In certain specific embodiments, R$_{14}$ is phenyl dimethyl-amine. In even more specific embodiments, R$_1$ is C(O)NHR$_{14}$ and R$_{14}$ is phenyl dimethyl-amine.

In certain specific embodiments R$_7$ is —OCH$_2$C(O)OC$_2$H$_5$.

In certain specific embodiments, R$_{14}$ is benzyloxy phenyl. In even more specific embodiments, R$_1$ is C(O)NHR$_{14}$ and R$_{14}$ is benzyloxy phenyl.

In certain specific embodiments, R$_{14}$ is para-bromo-phenyl. In even more specific embodiments, R$_1$ is —C(O)R$_{14}$ and R$_{14}$ is para-bromo-phenyl.

In certain specific embodiments, R$_a$ is para-hydroxy-phenyl. In even more specific embodiments, Y$_m$ is —CH$_2$— and R$_{14}$ is para-hydroxy-phenyl.

In certain specific embodiments, R$_7$ is —NH(phenyl)OCH$_3$.

In certain specific embodiments R$_1$ is —(CH$_2$)$_2$OS(O)$_2$O$^-$.

In certain specific embodiments, R$_{11}$ and R$_{12}$ are not joined together with the carbon atom to which each is attached.

In another embodiment, the invention provides a method for making a compound having the Formula (Ia):

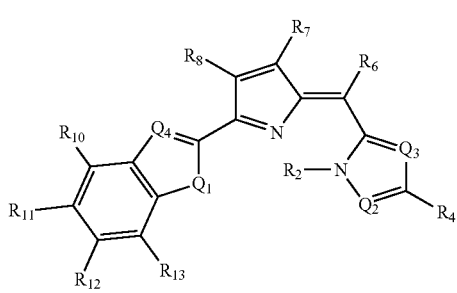

the method comprising the steps of
(a) contacting a compound of Formula (II)

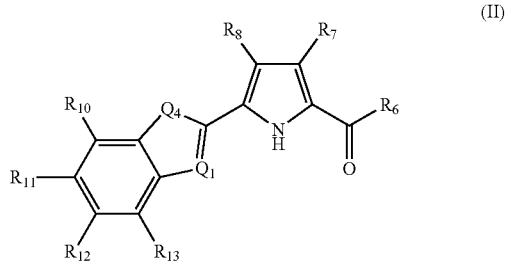

with a compound of Formula (v)

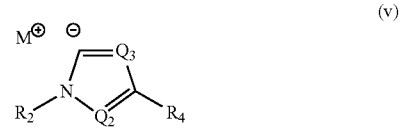

wherein M is Li, Na, K, Rb or Cs,
in the presence of a substantially anhydrous, aprotic organic solvent, for a time and at a temperature sufficient to make a compound of Formula (vi)

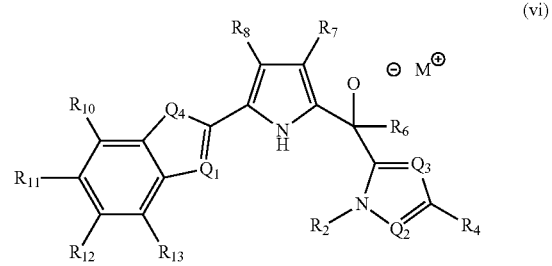

wherein M is defined as above; and
(b) protonating the compound of Formula (vi) with an H$^+$ donor for a time and at a temperature sufficient to make a compound of Formula (Ia)
wherein
Q$_1$ is —O—, —S— or —N(R$_1$)—
Q$_2$ is —C(R$_3$)— or —N—;
Q$_3$ is —C(R$_5$)— or —N—;
Q$_4$ is —C(R$_9$)— or —N—;
R$_1$ is —Y$_m$(R$_a$), wherein —R$_a$ is —H, —OH, —C$_1$-C$_8$ alkyl, —C$_2$-C$_8$ alkenyl, —C$_2$-C$_8$ alkynyl, —C$_3$-C$_{12}$ cycloalkyl, -phenyl, -naphthyl, -3- to 9-membered heterocycle, —OR$_{14}$, —O(CH$_2$)$_n$OR$_{14}$, —C(O)R$_{14}$, —O—C(O)R$_{14}$, —C(O)(CH$_2$)$_n$—R$_{14}$, —O—C(O)OR$_{14}$, —O—C(O)NHR$_{14}$, —O—C(O)N(R$_{14}$)$_2$, —C(O)N(R$_{14}$)$_2$, —C(O)OR$_{14}$, —C(O)NHR$_{14}$, —S—R$_{14}$, —SOR$_{14}$, —S(O)$_2$R$_{14}$, —NHC(O)R$_{14}$, —NHSR$_{14}$, —NHSOR$_{14}$, —NHS(O)$_2$R$_{14}$, —OS(O)$_2$O$^-$, O—C(S)R$_{14}$, O—C(S)OR$_{14}$, O—C(S)NHR$_{14}$, O—C(S)N(R$_{14}$)$_2$, —C(S)OR$_{14}$, —C(S)NHR$_{14}$, —C(S)N(R$_{14}$)$_2$, —NHC(S)R$_{14}$, —NR$_{14}$C(S)R$_{14}$, —NHC(S)NHR$_{14}$, —NHC(S)N(R$_{14}$)$_2$, —NR$_{14}$C(S)NHR$_{14}$, or —NR$_{14}$C(S)N(R$_{14}$)$_2$;
R$_2$ is —H, —C$_1$-C$_8$ alkyl or —OH;

$R_3$, $R_4$, and $R_5$ are independently —$Y_m(R_b)$, wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —$O(CH_2)_nOR_{14}$, —$C(O)R_{14}$, —O—$C(O)R_{14}$, —$C(O)(CH_2)_n$—$R_{14}$, —O—$C(O)OR_{14}$, —O—$C(O)NHR_{14}$, —O—$C(O)N(R_{14})_2$, —$C(O)N(R_{14})_2$, —$C(O)OR_{14}$, —$C(O)NHR_{14}$, —S—$R_{14}$, —$SOR_{14}$, —$S(O)_2R_{14}$, —$NHC(O)R_{14}$, —$NHSR_{14}$, —$NHSOR_{14}$, —$NHS(O)_2R_{14}$, O—$C(S)OR_{14}$, O—$C(S)OR_{14}$, O—$C(S)NHR_{14}$, O—$C(S)N(R_{14})_2$, —$C(S)OR_{14}$, —$C(S)NHR_{14}$, —$C(S)N(R_{14})_2$, —$NHC(S)R_{14}$, —$NR_{14}C(S)R_{14}$, —$NHC(S)NHR_{14}$, —$NHC(S)N(R_{14})_2$, —$NR_{14}C(S)NHR_{14}$, —$NR_{14}C(S)N(R_{14})_2$; or $R_3$ and $R_4$, or $R_4$ and $R_5$, together with the carbon atom to which each is attached, join to form a 5- to 9-membered ring, with the proviso that if $Q_3$ is —$C(R_5)$— and m=0, then $R_5$ is not H;

$R_6$ is —H, halogen, —OH, —$NH_2$, —$C_1$-$C_8$ alkyl, or —O—($C_1$-$C_8$ alkyl);

$R_7$ is —$Y_m(R_c)$, wherein —$R_c$ is —$C_1$-$C_8$ alkyl, —O—($C_1$-$C_8$ alkyl), —O-benzyl, —OH, —$NH_2$, —$NH(C_1$-$C_5$ alkyl), —$N(C_1$-$C_5$ alkyl$)_2$, —$NH(phenyl)$, —$N(phenyl)_2$, —$NH(naphthyl)$, —$N(naphthyl)_2$, —CN, —$NO_2$, —$N_3$, —$C_2$-$C_8$ alkynyl, —$OR_{14}$, —$O(CH_2)_nOR_{14}$, —$C(O)R_{14}$, —O—$C(O)R_{14}$, —$C(O)(CH_2)_n$—$R_{14}$, —O—$C(O)OR_{14}$, —O—$C(O)NHR_{14}$, —O—$C(O)N(R_{14})_2$, —$C(O)N(R_{14})_2$, —$C(O)OR_{14}$, —$C(O)NHR_{14}$, —S—$R_{14}$, —$SOR_{14}$, —$S(O)_2R_{14}$, —$NHC(O)R_{14}$, —$NHSR_{14}$, —$NHSOR_{14}$, —$NHS(O)_2R_{14}$, —$O(CH_2)_nC(O)O(CH_2)_nCH_3$, O—$C(S)R_{14}$, O—$C(S)OR_{14}$, O—$C(S)NHR_{14}$, O—$C(S)N(R_{14})_2$, —$C(S)OR_{14}$, —$C(S)NHR_{14}$, —$C(S)N(R_{14})_2$, —$NHC(S)R_{14}$, —$NR_{14}C(S)R_{14}$, —$NHC(S)NHR_{14}$, —$NHC(S)N(R_{14})_2$, —$NR_{14}C(S)NHR_{14}$, —$NR_{14}C(S)N(R_{14})_2$;

$R_8$ is —$Y_m(R_d)$, wherein —$R_d$ is —H, —OH, halogen, amino, —$NH(C_1$-$C_5$ alkyl), —$N(C_1$-$C_5$ alkyl$)_2$, —$NH(phenyl)$, —$N(phenyl)_2$, —$NH(naphthyl)$, —$N(naphthyl)_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —$O(CH_2)_nOR_{14}$, —$C(O)R_{14}$, —O—$C(O)R_{14}$, —$C(O)(CH_2)_n$—$R_{14}$, —O—$C(O)OR_{14}$, —O—$C(O)NHR_{14}$, —O—$C(O)N(R_{14})_2$, —$C(O)N(R_{14})_2$, —$C(O)OR_{14}$, —$C(O)NHR_{14}$, —S—$R_{14}$, —$SOR_{14}$, —$S(O)_2R_{14}$, —$NHC(O)R_{14}$, —$NHSR_{14}$, —$NHSOR_{14}$, —$NHS(O)_2R_{14}$, O—$C(S)R_{14}$, O—$C(S)OR_{14}$, O—$C(S)NHR_{14}$, O—$C(S)N(R_{14})_2$, —$C(S)OR_{14}$, —$C(S)NHR_{14}$, —$C(S)N(R_{14})_2$, —$NHC(S)R_{14}$, —$NR_{14}C(S)R_{14}$, —$NHC(S)NHR_{14}$, —$NHC(S)N(R_{14})_2$, —$NR_{14}C(S)NHR_{14}$, —$NR_{14}C(S)N(R_{14})_2$;

$R_9$, $R_{10}$, $R_{11}$, $R_{12}$, and $R_{13}$ are independently —$Y_m(R_e)$, wherein —$R_e$ is —H, halogen, —$NH_2$, $C_1$-$C_8$ alkyl, —$NH(C_1$-$C_5$ alkyl), —$N(C_1$-$C_5$ alkyl$)_2$, —$NH(phenyl)$, —$N(phenyl)_2$, —$NH(naphthyl)$, —$N(naphthyl)_2$, —$C(O)NH(C_1$-$C_5$ alkyl), —$C(O)N(C_1$-$C_5$ alkyl$)_2$, —$NHC(O)(C_1$-$C_5$ alkyl), —$NHC(=NH_2^+)NH_2$, —CN, —$NO_2$, $N_3$, -3- to 9-membered heterocycle, —$OR_{14}$, —$O(CH_2)_nOR_{14}$, —$C(O)R_{14}$, —O—$C(O)R_{14}$, —$C(O)(CH_2)_n$—$R_{14}$, —O—$C(O)OR_{14}$, —O—$C(O)NHR_{14}$, —O—$C(O)N(R_{14})_2$, —$C(O)N(R_{14})_2$, —$C(O)OR_{14}$, —$C(O)NHR_{14}$, —S—$R_{14}$, —$SOR_{14}$, —$S(O)_2R_{14}$, —$NHC(O)R_{14}$, —$NHSR_{14}$, —$NHSOR_{14}$, —$NHS(O)_2R_{14}$, O—$C(S)R_{14}$, O—$C(S)OR_{14}$, O—$C(S)NHR_{14}$, O—$C(S)N(R_{14})_2$, —$C(S)OR_{14}$, —$C(S)NHR_{14}$, —$C(S)N(R_{14})_2$, —$NHC(S)R_{14}$, —$NR_{14}C(S)R_{14}$, —$NHC(S)NHR_{14}$, —$NHC(S)N(R_{14})_2$, —$NR_{14}C(S)NHR_{14}$, —$NR_{14}C(S)N(R_{14})_2$ or $R_{11}$ and $R_{12}$, together with the carbon atom to which each is attached, join to form a 5- to 9-membered heterocycle;

each $R_{14}$ is independently —H, —$C_1$-$C_8$ alkyl, —$C_3$-$C_{12}$ cycloalkyl, -phenyl, -naphthyl, -3- to 9-membered heterocycle, —$C_2$-$C_8$ alkenyl, or —$C_2$-$C_8$ alkynyl;

each Y is independently —$C_1$-$C_8$ alkylene-, —$C_2$-$C_8$ alkenylene- or —$C_2$-$C_8$ alkynylene-;

each m is independently 0 or 1; and each n is independently an integer ranging from 0 to 6.

In certain specific embodiments, —O-benzyl is unsubstituted.

In certain specific embodiments, $R_7$ is 3-methoxy benzyloxy.

In certain specific embodiments, -phenyl is unsubstituted.

In certain specific embodiments, $R_{14}$ is phenyl dimethylamine. In even more specific embodiments, $R_1$ is $C(O)NHR_{14}$ and $R_{14}$ is phenyl dimethyl-amine.

In certain specific embodiments $R_7$ is —$OCH_2C(O)OC_2H_5$.

In certain specific embodiments, $R_{14}$ is benzyloxy phenyl. In even more specific embodiments, $R_1$ is $C(O)NHR_{14}$ and $R_{14}$ is benzyloxy phenyl.

In certain specific embodiments, $R_{14}$ is para-bromo-phenyl. In even more specific embodiments, $R_1$ is —$C(O)R_{14}$ and $R_{14}$ is para-bromo-phenyl.

In certain specific embodiments, $R_a$ is para-hydroxy-phenyl. In even more specific embodiments, $Y_m$ is —$CH_2$— and $R_{14}$ is para-hydroxy-phenyl.

In certain specific embodiments, $R_7$ is —NH(phenyl)$OCH_3$.

In certain specific embodiments $R_1$ is —$(CH_2)_2OS(O)_2O^-$.

In certain specific embodiments, $R_{11}$ and $R_{12}$ are not joined together with the carbon atom to which each is attached.

The invention further provides compositions comprising a pharmaceutically acceptable carrier or vehicle and an effective amount of a compound having the Formula (Ib):

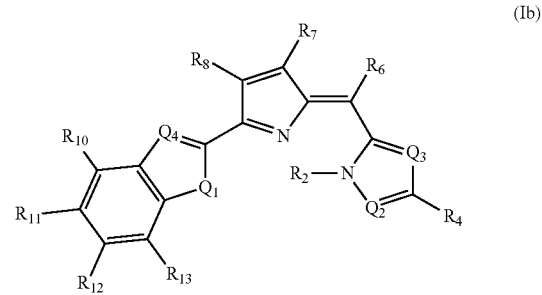

(Ib)

or a pharmaceutically acceptable salt thereof wherein $Q_1$ is —O—, —S— or —N($R_1$)—

$Q_2$ is —C($R_3$)— or —N—;

$Q_3$ is —C($R_5$)— or —N—;

$Q_4$ is —C($R_9$)— or —N—;

$R_1$ is —$Y_m(R_a)$, wherein —$R_a$ is —H, —OH, —$C_1$-$C_8$ alkyl, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —$O(CH_2)_nOR_{14}$, —$C(O)R_{14}$, —O—$C(O)R_{14}$, —$C(O)(CH_2)_n$—$R_{14}$, —O—$C(O)OR_{14}$, —O—$C(O)NHR_{14}$, —O—$C(O)N(R_{14})_2$, —$C(O)N(R_{14})_2$, —$C(O)OR_{14}$, —$C(O)NHR_{14}$, —S—$R_{14}$, —$SOR_{14}$, —$S(O)_2R_{14}$, —$NHC(O)R_{14}$, —$NHSR_{14}$, —$NHSOR_{14}$, —$NHS(O)_2R_{14}$, —$OS(O)_2O^-$, O—$C(S)R_{14}$, O—$C(S)OR_{14}$, O—$C(S)NHR_{14}$, O—$C(S)N(R_{14})_2$, —$C(S)OR_{14}$, —$C(S)NHR_{14}$, —$C(S)N(R_{14})_2$, —$NHC(S)R_{14}$, —$NR_{14}C(S)R_{14}$, —$NHC(S)NHR_{14}$, —$NHC(S)N(R_{14})_2$, —$NR_{14}C(S)NHR_{14}$, or —$NR_{14}C(S)N(R_{14})_2$;

$R_2$ is —H, —$C_1$-$C_8$ alkyl or —OH;

$R_3$, $R_4$, and $R_5$ are independently —$Y_m(R_b)$, wherein $R_b$ is —H, halogen, —$NH_2$, —CN, —$NO_2$, —SH, —$N_3$, $C_1$-$C_8$ alkyl, —O—($C_1$-$C_8$ alkyl), —$C_2$-$C_8$ alkenyl, —$C_2$-$C_8$ alkynyl, $C_3$-$C_{12}$ cycloalkyl, -phenyl, -naphthyl, -3- to 9-membered heterocycle, —$OR_{14}$, —$O(CH_2)_nOR_{14}$, —$C(O)R_{14}$, —O—$C(O)R_{14}$, —$C(O)(CH_2)_n$—$R_{14}$, —O—$C(O)OR_{14}$, —O—$C(O)NHR_{14}$, —O—$C(O)N(R_{14})_2$, —$C(O)N(R_{14})_2$, —$C(O)OR_{14}$, —$C(O)NHR_{14}$, —S—$R_{14}$, —$SOR_{14}$, —$S(O)_2R_{14}$, —$NHC(O)R_{14}$, —$NHSR_{14}$, —$NHSOR_{14}$, —$NHS(O)_2R_{14}$, O—$C(S)R_{14}$, O—$C(S)OR_{14}$, O—$C(S)NHR_{14}$, O—$C(S)N(R_{14})_2$, —$C(S)OR_{14}$, —$C(S)NHR_{14}$, —$C(S)N(R_{14})_2$, —$NHC(S)R_{14}$, —$NR_{14}C(S)R_{14}$, —$NHC(S)NHR_{14}$, —$NHC(S)N(R_{14})_2$, —$NR_{14}C(S)NHR_{14}$, —$NR_{14}C(S)N(R_{14})_2$ or $R_3$ and $R_4$, or $R_4$ and $R_5$, together with the carbon atom to which each is attached, join to form a 5- to 9-membered ring, with the proviso that if $Q_3$ is —$C(R_5)$— and m=0, then $R_5$ is not H;

$R_6$ is —H, halogen, —OH, —$NH_2$, —$C_1$-$C_8$ alkyl, or —O—($C_1$-$C_8$ alkyl);

$R_7$ and $R_8$ are independently —$Y_m(R_d)$ wherein $R_d$ is —H, —OH, halogen, amino, —NH($C_1$-$C_8$ alkyl), —N($C_1$-$C_5$ alkyl)$_2$, —NH(phenyl), —N(phenyl)$_2$, —NH(naphthyl), —N(naphthyl)$_2$, —CN, —$NO_2$, —$N_3$, —$C_1$-$C_8$ alkyl, —O—($C_1$-$C_8$ alkyl), —($C_1$-$C_8$ alkyl)-OH, —O-benzyl, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —$CH_2O$—$(CH_2)_nOR_{14}$, —O—$C(O)R_{14}$, —$C(O)(CH_2)_n$—$R_{14}$, —$C(O)R_{14}$, —O—$C(O)OR_{14}$, —O—$C(O)NHR_{14}$, —O—$C(O)N(R_{14})_2$, —$C(O)N(R_{14})_2$, —$C(O)OR_{14}$, —$C(O)NHR_{14}$, —S—$R_{14}$, —$SOR_{14}$, —$S(O)_2R_{14}$, —$NHC(O)R_{14}$, —$NHSR_{14}$, —$NHSOR_{14}$, —$NHS(O)_2R_{14}$, O—$C(S)R_{14}$, O—$C(S)OR_{14}$, O—$C(S)NHR_{14}$, O—$C(S)N(R_{14})_2$, —$C(S)OR_{14}$, —$C(S)NHR_{14}$, —$C(S)N(R_{14})_2$, —$NHC(S)R_{14}$, —$NR_{14}C(S)R_{14}$, —$NHC(S)NHR_{14}$, —$NHC(S)N(R_{14})_2$, —$NR_{14}C(S)NHR_{14}$, —$NR_{14}C(S)N(R_{14})_2$;

$R_9$, $R_{10}$, $R_{11}$, $R_{12}$, and $R_{13}$ are independently —$Y_m(R_e)$ wherein $R_e$ is —H, halogen, —$NH_2$, $C_1$-$C_8$ alkyl, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —$C(O)NH(C_1$-$C_5$ alkyl), —$C(O)N(C_1$-$C_5$ alkyl)$_2$, —$NHC(O)(C_1$-$C_8$ alkyl), —NHC(=$NH_2^+$)$NH_2$, —CN, —$NO_2$, $N_3$, -3- to 9-membered heterocycle, —$OR_{14}$, —$CH_2O$—$(CH_2)_nOR_{14}$, —O—$C(O)R_{14}$, —$C(O)(CH_2)_n$—$R_{14}$, —$C(O)R_{14}$, —O—$C(O)OR_{14}$, —O—$C(O)NHR_{14}$, —O—$C(O)N(R_{14})_2$, —$C(O)N(R_{14})_2$, —$C(O)OR_{14}$, —$C(O)NHR_{14}$, —S—$R_{14}$, —$SOR_{14}$, —$S(O)_2R_{14}$, —$NHC(O)R_{14}$, —$NHSR_{14}$, —$NHSOR_{14}$, —$NHS(O)_2R_{14}$, O—$C(S)R_{14}$, O—$C(S)OR_{14}$, O—$C(S)NHR_{14}$, O—$C(S)N(R_{14})_2$, —$C(S)OR_{14}$, —$C(S)NHR_{14}$, —$C(S)N(R_{14})_2$, —$NHC(S)R_{14}$, —$NR_{14}C(S)R_{14}$, —$NHC(S)NHR_{14}$, —$NHC(S)N(R_{14})_2$, —$NR_{14}C(S)NHR_{14}$, —$NR_{14}C(S)N(R_{14})_2$ or $R_{11}$ and $R_{12}$, together with the carbon atom to which each is attached, join to form a 5- to 9-membered heterocycle;

each $R_{14}$ is independently —H, —$C_1$-$C_8$ alkyl, —$C_3$-$C_{12}$ cycloalkyl, -phenyl, -naphthyl, -3- to 9-membered heterocycle, —$C_2$-$C_8$ alkenyl, or —$C_2$-$C_8$ alkynyl;

each Y is independently —$C_1$-$C_8$ alkylene-, —$C_2$-$C_8$ alkenylene- or —$C_2$-$C_8$ alkynylene-;

each m is independently 0 or 1; and each n is independently an integer ranging from 0 to 6.

In certain specific embodiments, —O-benzyl is unsubstituted.

In certain specific embodiments, $R_7$ is 3-methoxy benzyloxy.

In certain specific embodiments, -phenyl is unsubstituted.

In certain specific embodiments, $R_{14}$ is phenyl dimethylamine. In even more specific embodiments, $R_1$ is C(O)$NHR_{14}$ and $R_{14}$ is phenyl dimethyl-amine.

In certain specific embodiments $R_7$ is —$OCH_2C(O)OC_2H_5$.

In certain specific embodiments, $R_{14}$ is benzyloxy phenyl. In even more specific embodiments, $R_1$ is C(O)$NHR_{14}$ and $R_{14}$ is benzyloxy phenyl.

In certain specific embodiments, $R_{14}$ is para-bromo-phenyl. In even more specific embodiments, $R_1$ is —$C(O)R_{14}$ and $R_{14}$ is para-bromo-phenyl.

In certain specific embodiments, $R_a$ is para-hydroxy-phenyl. In even more specific embodiments, $Y_m$ is —$CH_2$— and $R_{14}$ is para-hydroxy-phenyl.

In certain specific embodiments, $R_7$ is —NH(phenyl)$OCH_3$.

In certain specific embodiments $R_1$ is —$(CH_2)_2OS(O)_2O^-$.

In certain specific embodiments, $R_{11}$ and $R_{12}$ are not joined together with the carbon atom to which each is attached.

In another aspect, the invention provides methods for treating cancer in a patient, comprising administering to a patient in need thereof an effective amount of a compound or a pharmaceutically acceptable salt of the compound having the Formula (Ib), depicted above, wherein $Q_1$-$Q_4$, $R_2$, $R_4$, $R_6$-$R_8$ and $R_{10}$-$R_{13}$ are defined above for the compounds of formula (Ib).

In still another aspect, the invention provides methods for treating a virus or a viral infection in a patient, comprising administering to a patient in need thereof an effective amount of a compound or a pharmaceutically acceptable salt of the compound having the Formula (Ib), depicted above, wherein $Q_1$-$Q_4$, $R_2$, $R_4$, $R_6$-$R_8$ and $R_{10}$-$R_{13}$ are defined above for the compounds of formula (Ib).

The present invention also encompasses compounds having the Formula (II):

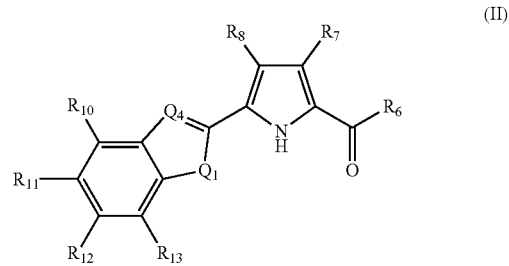

(II)

and pharmaceutically acceptable salts thereof, wherein:

$Q_1$ is —O—, —S— or —N($R_1$)—

$Q_4$ is —C($R_9$)— or —N—;

$R_1$ is —$Y_m(R_a)$, wherein —$R_a$ is —H, —OH, —$C_1$-$C_8$ alkyl, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —$O(CH_2)_nOR_{14}$, —$C(O)R_{14}$, —O—$C(O)R_{14}$, —$C(O)(CH_2)_n$—$R_{14}$, —O—$C(O)OR_{14}$, —O—$C(O)NHR_{14}$, —O—$C(O)N(R_{14})_2$, —$C(O)N(R_{14})_2$, —$C(O)OR_{14}$, —$C(O)NHR_{14}$, —$SOR_{14}$, —$S(O)_2R_{14}$, —$NHC(O)R_{14}$, —$NHSR_{14}$, —$NHSOR_{14}$, —$NHS(O)_2R_{14}$, —$OS(O)_2O^-$, O—$C(S)R_{14}$, O—$C(S)OR_{14}$, O—$C(S)NHR_{14}$, O—$C(S)N(R_{14})_2$, —$C(S)OR_{14}$, —$C(S)NHR_{14}$, —$C(S)N(R_{14})_2$, —$NHC(S)R_{14}$, —$NR_{14}C(S)R_{14}$, —$NHC(S)NHR_{14}$, —$NHC(S)N(R_{14})_2$, —$NR_{14}C(S)NHR_{14}$, or —$NR_{14}C(S)N(R_{14})_2$;

$R_6$ is —H, halogen, —OH, —$NH_2$, —$C_1$-$C_8$ alkyl, or —O—($C_1$-$C_8$ alkyl);

$R_7$ and $R_8$ are independently —$Y_m(R_d)$ wherein $R_d$ is —H, —OH, halogen, amino, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —$NO_2$, —$N_3$, —$C_1$-$C_8$ alkyl, —O—

(C₁-C₈ alkyl), —(C₁-C₈ alkyl)-OH, —O-benzyl, —C₂-C₈ alkenyl, —C₂-C₈ alkynyl, —C₃-C₁₂ cycloalkyl, -phenyl, -naphthyl, —C₇-C₁₂ (phenyl)alkyl, —C₇-C₁₂ (naphthyl)alkyl, —C₇-C₁₂ (phenyl)alkenyl, —C₇-C₁₂ (naphthyl)alkenyl, —C₇-C₁₂ (phenyl)alkynyl, —C₇-C₁₂ (naphthyl)alkynyl, -3- to 9-membered heterocycle, —OR₁₄, —O(CH₂)ₙOR₁₄, —C(O)R₁₄, —O—C(O)R₁₄, —C(O)(CH₂)ₙ—R₁₄, —O—C(O)OR₁₄, —O—C(O)NHR₁₄, —O—C(O)N(R₁₄)₂, —C(O)N(R₁₄)₂, —C(O)OR₁₄, —C(O)NHR₁₄, —S—R₁₄, —SOR₁₄, —S(O)₂R₁₄, —NHC(O)R₁₄, —NHSR₁₄, —NHSOR₁₄, —NHS(O)₂R₁₄, O—C(S)R₁₄, O—C(S)OR₁₄, O—C(S)NHR₁₄, O—C(S)N(R₁₄)₂, —C(S)OR₁₄, —C(S)NHR₁₄, —C(S)N(R₁₄)₂, —NHC(S)R₁₄, —NR₁₄C(S)R₁₄, —NHC(S)NHR₁₄, —NHC(S)N(R₁₄)₂, —NR₁₄C(S)NHR₁₄, —NR₁₄C(S)N(R₁₄)₂;

R₉, R₁₀, R₁₁, R₁₂, and R₁₃ are independently —Yₘ(Rₑ) wherein Rₑ is —H, halogen, —NH₂, C₁-C₈ alkyl, —NH(C₁-C₅ alkyl), —N(C₁-C₅ alkyl)₂, —NH(phenyl), —N(phenyl)₂, —NH(naphthyl), —N(naphthyl)₂, —C(O)NH(C₁-C₅ alkyl), —C(O)N(C₁-C₅ alkyl)₂, —NHC(O)(C₁-C₅ alkyl), —NHC(=NH₂⁺)NH₂, —CN, —NO₂, N₃, -3- to 9-membered heterocycle, —OR₁₄, —O(CH₂)ₙOR₁₄, —C(O)R₁₄, —O—C(O)R₁₄, —C(O)(CH₂)ₙ—R₁₄, —O—C(O)OR₁₄, —O—C(O)NHR₁₄, —O—C(O)N(R₁₄)₂, —C(O)N(R₁₄)₂, —C(O)OR₁₄, —C(O)NHR₁₄, —S—R₁₄, —SOR₁₄, —S(O)₂R₁₄, —NHC(O)R₁₄, —NHSR₁₄, —NHSOR₁₄, —NHS(O)₂R₁₄, O—C(S)R₁₄, O—C(S)OR₁₄, O—C(S)NHR₁₄, O—C(S)N(R₁₄)₂, —C(S)OR₁₄, —C(S)NHR₁₄, —C(S)N(R₁₄)₂, —NHC(S)R₁₄, —NR₁₄C(S)R₁₄, —NHC(S)NHR₁₄, —NHC(S)N(R₁₄)₂, —NR₁₄C(S)NHR₁₄, —NR₁₄C(S)N(R₁₄)₂ or R₁₁ and R₁₂, together with the carbon atom to which each is attached, join to form a 5- to 9-membered heterocycle;

each R₁₄ is independently —H, —C₁-C₈ alkyl, —C₃-C₁₂ cycloalkyl, -phenyl, -naphthyl, -3- to 9-membered heterocycle, —C₂-C₈ alkenyl, or —C₂-C₈ alkynyl;

each Y is independently —C₁-C₈ alkylene-, —C₂-C₈ alkenylene- or —C₂-C₈ alkynylene-;

each m is independently 0 or 1; and each n is independently an integer ranging from 0 to 6.

A compound of Formula (Ia), (Ib) or (II) or a pharmaceutically acceptable salt thereof (a "Triheterocyclic Compound") is useful for treating or preventing cancer or neoplastic disease in a patient in need of such treatment or prevention, inhibiting the growth of a cancer cell or neoplastic cell, treating or preventing a viral infection in a patient in need of such treatment or prevention or inhibiting the replication or infectivity of a virus.

The invention further provides methods for treating or preventing cancer or neoplastic disease, comprising administering to a patient in need of such treatment or prevention, an effective amount of a Triheterocyclic Compound.

The invention further provides methods for inhibiting the growth of a cancer or neoplastic cells, comprising contacting the cancer or neoplastic cell with an effective amount of a Triheterocyclic Compound.

The invention further provides methods for treating or preventing a viral infection, comprising administering to a patient in need of such treatment or prevention an effective amount of a Triheterocyclic Compound.

The invention further provides methods for inhibiting the replication or infectivity of a virus, comprising contacting a virus or a virus-infected cell with an effective amount of a Triheterocyclic Compound.

In a further aspect, the present invention relates to methods useful for making the Triheterocyclic Compounds having the Formula (Ib).

In one embodiment, the invention provides a method for making a compound having the Formula (Ib):

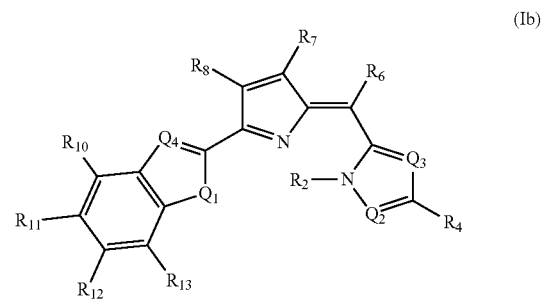

(Ib)

comprising contacting a compound of Formula (II)

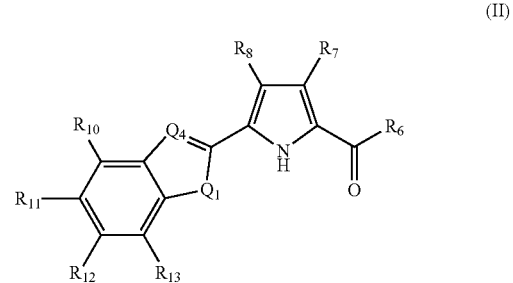

(II)

with a compound of Formula (iv)

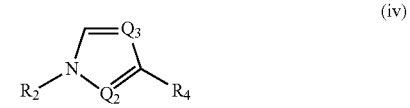

(iv)

in the presence of an organic solvent and a protic acid, for a time and at a temperature sufficient to make the compound of Formula (Ib), wherein Q₁-Q₄, R₂, R₄, R₆-R₈ and R₁₀-R₁₃ are defined above for the Triheterocyclic Compounds of Formula (Ib).

In another embodiment, the invention provides methods for making a compound having the Formula (Ib):

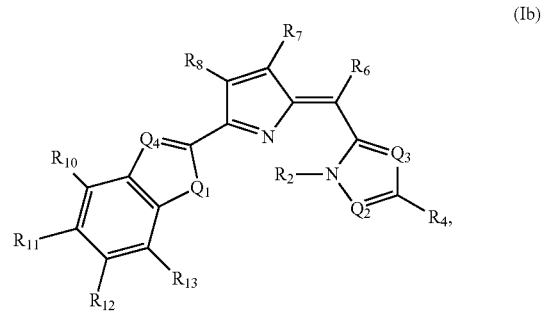

(Ib)

comprising the steps of:

(a) contacting a compound of Formula (II)

(II)

with a compound of Formula (v)

(v)

wherein M is Li, Na, K, Rb or Cs, in the presence of a substantially anhydrous, aprotic organic solvent, for a time and at a temperature sufficient to make a compound of Formula (vi)

(vi)

wherein M is defined as above; and (b) protonating the compound of Formula (vi) with an H+ donor for a time and at a temperature sufficient to make a compound of Formula (Ib), wherein $Q_1$-$Q_4$, $R_2$, $R_4$, $R_6$-$R_8$ and $R_{10}$-$R_{13}$ are defined above for the compounds of Formula (Ib).

In a further aspect, the invention provides methods for making a compound having the Formula (II):

(II)

comprising contacting a compound of Formula (iii)

(iii)

with a compound of Formula (ii) or a compound of Formula (iia)

(ii)

(iia)

in the presence of an organic solvent, a base, and a Ni or Pd catalyst, for a time and at a temperature sufficient to form a compound of Formula (II), wherein $Q_1$, $Q_4$, $R_6$-$R_8$ and $R_{10}$-$R_{13}$ are defined above for the Triheterocyclic Compounds of Formula (II), and wherein $R_{15}$ is independently $C_1$ to $C_8$ alkyl, cycloalkyl or phenyl.

In a specific embodiment, the Triheterocyclic Compound is Compound 1:

Compound 1 or a pharmaceutically acceptable salt thereof.

In another embodiment, the Triheterocyclic Compound is Compound 1 tartrate salt.

In even another embodiment, the Triheterocyclic Compound is Compound 1 mesylate salt.

In yet other embodiments, the Triheterocyclic Compound is a prodrug of Compound 1. In more specific embodiments, the prodrug of Compound 1 is Compound 66 or Compound 67 or pharmaceutically acceptable salts thereof.

Compound 66

Phosphoric acid mono-[2-(3-{2-[5-(3,5-dimethyl-1H-pyrrol-2-ylmethylene)-4-methoxy-5H-pyrrol-2-yl]-indol-1-yl}-1, 1-dimethyl-3-oxo-propyl)-3-methyl-phenyl] ester Compound 67

Phosphoric acid mono-(2-{2-[5-(3,5-dimethyl-1H-pyrrol-2-ylmethylene)-4-methoxy-5H-pyrrol-2-yl]-indole-1-carbonyl}-benzyl) ester The present invention encompasses compounds having the Formula (Ic):

(Ic)

and pharmaceutically acceptable salts thereof, wherein:

$Q_1$ is —O—, —S— or —N($R_1$)—
$Q_2$ is —C($R_3$)— or —N—;
$Q_3$ is —C($R_5$)— or —N—;
$Q_4$ is —C($R_9$)— or —N—;
$R_1$ is —$Y_m$($R_a$), wherein —$R_a$ is —H, —OH, —$C_1$-$C_8$ alkyl, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —$O(CH_2)_nOR_{14}$, —$C(O)R_{14}$, —O—C(O)$R_{14}$, —C(O)($CH_2$)$_n$—$R_{14}$, —O—C(O)$OR_{14}$, —O—C(O)NH$R_{14}$, —O—C(O)N($R_{14}$)$_2$, —C(O)N($R_{14}$)$_2$, —C(O)$OR_{14}$, —C(O)NH$R_{14}$, —S—$R_{14}$, —$SOR_{14}$, —S(O)$_2R_{14}$, —NHC(O)$R_{14}$, —NHS$R_{14}$, —NHSO$R_{14}$, —NHS(O)$_2R_{14}$, —OS(O)$_2$O$^-$, O—C(S)$R_{14}$, O—C(S)O$R_{14}$, O—C(S)NH$R_{14}$, O—C(S)N($R_{14}$)$_2$, —C(S)O$R_{14}$, —C(S)NH$R_{14}$, —C(S)N($R_{14}$)$_2$, —NHC(S)$R_{14}$, —$NR_{14}$C(S)$R_{14}$, —NHC(S)NH$R_{14}$, —NHC(S)N($R_{14}$)$_2$, —$NR_{14}$C(S)NH$R_{14}$, or —$NR_{14}$C(S)N($R_{14}$)$_2$;

$R_2$ is —H, —$C_1$-$C_8$ alkyl or —OH;

$R_3$, $R_4$, and $R_5$ are independently —$Y_m$($R_b$), wherein $R_b$ is —H, halogen, —$NH_2$, —CN, —$NO_2$, —SH, —$N_3$, —$C_1$-$C_8$ alkyl, —O—($C_1$-$C_8$ alkyl), —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —$O(CH_2)_nOR_{14}$, —$C(O)R_{14}$, —O—C(O)$R_{14}$, —C(O)($CH_2$)$_n$—$R_{14}$, —O—C(O)$OR_{14}$, —O—C(O)NH$R_{14}$, —O—C(O)N($R_{14}$)$_2$, —C(O)N($R_{14}$)$_2$, —C(O)$OR_{14}$, —C(O)NH$R_{14}$, —S—$R_{14}$, —$SOR_{14}$, —S(O)$_2R_{14}$, —NHC(O)$R_{14}$, —NHS$R_{14}$, —NHSO$R_{14}$, —NHS(O)$_2R_{14}$, O—C(S)$R_{14}$, O—C(S)O$R_{14}$, O—C(S)NH$R_{14}$, O—C(S)N($R_{14}$)$_2$, —C(S)O$R_{14}$, —C(S)NH$R_{14}$, —C(S)N($R_{14}$)$_2$, —NHC(S)$R_{14}$, —$NR_{14}$C(S)$R_{14}$, —NHC(S)NH$R_{14}$, —NHC(S)N($R_{14}$)$_2$, —$NR_{14}$C(S)NH$R_{14}$, —$NR_{14}$C(S)N($R_{14}$)$_2$ or $R_3$ and $R_4$, or $R_4$ and $R_5$, together with the carbon atom to which each is attached, join to form a 5- to 9-membered ring;

$R_6$ is —H, halogen, —OH, —$NH_2$, —$C_1$-$C_8$ alkyl, or —O—($C_1$-$C_8$ alkyl);

$R_7$ is —$Y_m$—($R_c$), wherein —$R_c$ is —$C_1$-$C_8$ alkyl, —O—($C_1$-$C_8$ alkyl), —O-benzyl, —OH, —$NH_2$, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —$NO_2$, —$N_3$, —$C_2$-$C_8$ alkynyl, —$OR_{14}$, —$O(CH_2)_nOR_{14}$, —$C(O)R_{14}$, —O—C(O)$R_{14}$, —C(O)($CH_2$)$_n$—$R_{14}$, —O—C(O)$OR_{14}$, —O—C(O)NH$R_{14}$, —O—C(O)N($R_{14}$)$_2$, —C(O)N($R_{14}$)$_2$, —C(O)$OR_{14}$, —C(O)NH$R_{14}$, —S—$R_{14}$, —$SOR_{14}$, —S(O)$_2R_{14}$, —NHC(O)$R_{14}$, —NHS$R_{14}$, —NHSO$R_{14}$, —NHS(O)$_2R_{14}$, —$O(CH_2)_nC(O)O(CH_2)_nCH_3$, O—C(S)$R_{14}$, O—C(S)O$R_{14}$, O—C(S)NH$R_{14}$, O—C(S)N($R_{14}$)$_2$, —C(S)O$R_{14}$, —C(S)NH$R_{14}$, —C(S)N($R_{14}$)$_2$, —NHC(S)$R_{14}$, —$NR_{14}$C(S)$R_{14}$, —NHC(S)NH$R_{14}$, —NHC(S)N($R_{14}$)$_2$, —$NR_{14}$C(S)NH$R_{14}$, —$NR_{14}$C(S)N($R_{14}$)$_2$;

$R_8$ is —$Y_m$($R_d$), wherein —$R_d$ is —H, —OH, halogen, amino, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —$NO_2$, —$N_3$, —$C_1$-$C_8$ alkyl, —O—($C_1$-$C_8$ alkyl), —($C_1$-$C_8$ alkyl)-OH, —$C_2$-$C_8$ alkenyl, —$C_2$-$C_8$ alkynyl, —$C_3$-$C_{12}$ cycloalkyl, -phenyl, -naphthyl, -3- to 9-membered heterocycle, —$OR_{14}$, —$O(CH_2)_nOR_{14}$, —$C(O)R_{14}$, —O—C(O)$R_{14}$, —C(O)($CH_2$)$_n$—$R_{14}$, —O—C(O)$OR_{14}$, —O—C(O)NH$R_{14}$, —O—C(O)N($R_{14}$)$_2$, —C(O)N($R_{14}$)$_2$, —C(O)$OR_{14}$, —C(O)NH$R_{14}$, —S—$R_{14}$, —$SOR_{14}$, —S(O)$_2R_{14}$, —NHC(O)$R_{14}$, —NHS$R_{14}$, —NHSO$R_{14}$, —NHS(O)$_2R_{14}$, O—C(S)$R_{14}$, O—C(S)O$R_{14}$, O—C(S)NH$R_{14}$, O—C(S)N($R_{14}$)$_2$, —C(S)O$R_{14}$, —C(S)NH$R_{14}$, —C(S)N($R_{14}$)$_2$, —NHC(S)$R_{14}$, —$NR_{14}$C(S)$R_{14}$, —NHC(S)NH$R_{14}$, —NHC(S)N($R_{14}$)$_2$, —$NR_{14}$C(S)NH$R_{14}$, —$NR_{14}$C(S)N($R_{14}$)$_2$;

$R_9$, $R_{10}$, $R_{11}$, $R_{12}$, and $R_{13}$ are independently —$Y_m$($R_e$), wherein —$R_e$ is —H, halogen, —$NH_2$, $C_1$-$C_8$ alkyl, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —C(O)NH($C_1$-$C_5$ alkyl), —C(O)N($C_1$-$C_5$ alkyl)$_2$, —NHC(O)($C_1$-$C_5$ alkyl), —NHC(=$NH_2^+$)$NH_2$, —CN, —$NO_2$, $N_3$, -3- to 9-membered heterocycle, —$OR_{14}$, —$O(CH_2)_nOR_{14}$, —$C(O)R_{14}$, —O—C(O)$R_{14}$, —C(O)($CH_2$)$_n$—$R_{14}$, —O—C(O)$OR_{14}$, —O—C(O)NH$R_{14}$, —O—C(O)N($R_{14}$)$_2$, —C(O)N($R_{14}$)$_2$, —C(O)$OR_{14}$, —C(O)NH$R_{14}$, —S—$R_{14}$, —S(O)$_2R_{14}$, —NHC(O)$R_{14}$, —NHS$R_{14}$, —NHSO$R_{14}$, —NHS(O)$_2R_{14}$, O—C(S)$R_{14}$, O—C(S)O$R_{14}$, O—C(S)NH$R_{14}$, O—C(S)N($R_{14}$)$_2$, —C(S)O$R_{14}$, —C(S)NH$R_{14}$, —C(S)N($R_{14}$)$_2$, —NHC(S)$R_{14}$, —$NR_{14}$C(S)$R_{14}$, —NHC(S)NH$R_{14}$, —NHC(S)N($R_{14}$)$_2$, —$NR_{14}$C(S)NH$R_{14}$, —$NR_{14}$C(S)N($R_{14}$)$_2$; or $R_{11}$ and $R_{12}$, together with the carbon atom to which each is attached, join to form a 5- to 9-membered heterocycle;

each $R_{14}$ is independently —H, —$C_1$-$C_8$ alkyl, —$C_3$-$C_{12}$ cycloalkyl, -phenyl, -naphthyl, -3- to 9-membered heterocycle, —$C_2$-$C_8$ alkenyl, or —$C_2$-$C_8$ alkynyl;

each Y is independently —$C_1$-$C_8$ alkylene-, —$C_2$-$C_8$ alkenylene- or —$C_2$-$C_8$ alkynylene-;

each m is independently 0 or 1; and each n is independently an integer ranging from 0 to 6.

In certain specific embodiments, —O-benzyl is unsubstituted.

In certain specific embodiments, $R_7$ is 3-methoxy benzyloxy.

In certain specific embodiments, -phenyl is unsubstituted.

In certain specific embodiments, $R_{14}$ is phenyl dimethyl-amine. In even more specific embodiments, $R_1$ is C(O)NH$R_{14}$ and $R_{14}$ is phenyl dimethyl-amine.

In certain specific embodiments $R_7$ is —OCH$_2$C(O)OC$_2$H$_5$.

In certain specific embodiments, $R_{14}$ is benzyloxy phenyl. In even more specific embodiments, $R_1$ is C(O)NH$R_{14}$ and $R_{14}$ is benzyloxy phenyl.

In certain specific embodiments, $R_{14}$ is para-bromo-phenyl. In even more specific embodiments, $R_1$ is —C(O)$R_{14}$ and $R_{14}$ is para-bromo-phenyl.

In certain specific embodiments, $R_a$ is para-hydroxy-phenyl. In even more specific embodiments, $Y_m$ is —CH$_2$— and $R_{14}$ is para-hydroxy-phenyl.

In certain specific embodiments, $R_7$ is —NH(phenyl)OCH$_3$.

In certain specific embodiments R1 is —(CH$_2$)$_2$OS(O)$_2$O$^-$.

In certain specific embodiments, $R_{11}$ and $R_{12}$ are not joined together with the carbon atom to which each is attached.

In another aspect, the invention provides pharmaceutical compositions comprising a compound of Formula (Ic), depicted above, wherein $Q_2$ and $Q_3$, $R_1$-$R_8$ and $R_{10}$-$R_{13}$ are defined above for the compounds of formula (Ic).

In another aspect, the invention provides methods for treating cancer in a patient, comprising administering to a patient in need thereof an effective amount of a compound or a pharmaceutically acceptable salt of the compound having the Formula (Ic), depicted above, wherein $Q_2$ and $Q_3$, $R_1$-$R_8$ and $R_{10}$-$R_{13}$ are defined above for the compounds of formula (Ic).

In still another aspect, the invention provides methods for treating a virus or a viral infection in a patient, comprising administering to a patient in need thereof an effective amount of a compound or a pharmaceutically acceptable salt of the compound having the Formula (Ic), depicted above, wherein $Q_2$-$Q_3$, $R_1$-$R_8$ and $R_{10}$-$R_{13}$ are defined above for the compounds of formula (Ic).

3.1 Definitions and Abbreviations

As used herein, "halogen" refers to —F, —Cl, —Br or —I.

As used herein, "$C_1$-$C_8$ alkyl" refers to a straight or branched chain saturated hydrocarbon group containing 1-8 carbon atoms which can be unsubstituted or optionally substituted with one or more -halogen, —NH$_2$, —OH, —O—($C_1$-$C_8$ alkyl), phenyl or naphthyl groups. Examples of $C_1$-$C_8$ straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, 1-heptyl and 1-octyl.

As used herein, "$C_1$-$C_5$ alkyl" refers to a straight or branched chain saturated hydrocarbon group containing 1-5 carbon atoms. Examples of $C_1$-$C_5$ straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl and 1-pentyl.

As used herein, "$C_2$-$C_8$ alkenyl" refers to an unsaturated, straight or branched chain hydrocarbon group containing 2-8 carbon atoms and at least one double bond which can be unsubstituted or optionally substituted with a phenyl or naphthyl group.

As used herein, "$C_2$-$C_8$ alkynyl" refers to an unsaturated, straight or branched chain hydrocarbon group containing 2-8 carbon atoms and at least one triple bond which can be unsubstituted or optionally substituted with a phenyl or naphthyl group.

As used herein, "$C_1$-$C_8$ alkylene" refers to a $C_1$-$C_8$ alkyl group in which one of the $C_1$-$C_8$ alkyl group's hydrogen atoms has been replaced with a bond.

As used herein, "$C_2$-$C_8$ alkenylene" refers to a $C_2$-$C_8$ alkenyl group in which one of the $C_2$-$C_8$ alkenyl group's hydrogen atoms has been replaced with a bond.

As used herein, "$C_2$-$C_8$ alkynylene" refers to a $C_2$-$C_8$ alkynyl group in which one of the $C_2$-$C_8$ alkynyl group's hydrogen atoms has been replaced with a bond.

As used herein, "$C_3$-$C_{12}$ cycloalkyl" refers to a non-aromatic, saturated monocyclic, bicyclic or tricyclic hydrocarbon ring system containing 3-12 carbon atoms. Examples of $C_3$-$C_{12}$ cycloalkyl groups include but are not limited to cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, a "-3- to 9-membered heterocycle" is a 3- to 9-membered aromatic or nonaromatic monocyclic or bicyclic ring of carbon atoms and from 1 to 4 heteroatoms selected from oxygen, nitrogen and sulfur. Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

A "5- to 9-membered ring" is a 5- to 9-membered aromatic or nonaromatic monocyclic or bicyclic ring of carbon atoms only, or of carbon atoms and from 1 to 4 heteroatoms selected from oxygen, nitrogen and sulfur. Examples of 5- to 9-membered rings include, but are not limited to, cyclopentyl, cyclohexyl or cycloheptyl, which may be saturated or unsaturated, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

As used herein, an —O-benzyl group can be substituted or unsubstituted.

As used herein, a -phenyl group can be substituted or unsubstituted.

When the groups described herein are said to be "substituted or unsubstituted," when substituted, they may be substituted with any desired substituent or substituents that do not adversely affect the desired activity of the compound. Examples of preferred substituents are those found in the exemplary compounds and embodiments disclosed herein, as well as halogen (chloro, iodo, bromo, or fluoro); $C_{1-6}$ alkyl; $C_{2-6}$ alkenyl; $C_{2-6}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); benzyloxy; amino (primary, secondary, or tertiary); —N(CH$_3$)$_2$; O-lower alkyl; O-aryl; aryl; aryl-lower alkyl; CO$_2$CH$_3$; —OCH$_2$CH$_3$; methoxy; CONH$_2$; OCH$_2$CONH$_2$; NH$_2$; SO$_2$NH$_2$; OCHF$_2$; CF$_3$; OCF$_3$; and such moieties may also be optionally substituted by a fused-ring structure or bridge, for example —OCH$_2$O—.

These substituents may optionally be further substituted with a substituent selected from such groups.

An "effective amount" is an amount of a Triheterocyclic Compound that is effective for: treating or preventing cancer or neoplastic disease; inhibiting the growth of a cancer cell or neoplastic cell; treating or preventing a viral infection; or inhibiting the replication or infectivity of a virus.

The phrase "substantially anhydrous," as used herein in connection with a reaction mixture or an organic solvent, means that the reaction mixture or organic solvent comprises less than about 1 percent of water by weight; in one embodiment, less than about 0.5 percent of water by weight; and in another embodiment, less than about 0.25 percent of water by weight of the reaction mixture or organic solvent.

In one embodiment, when administered to a patient, e.g., a mammal for veterinary use or a human for clinical use, the Triheterocyclic Compounds are administered in isolated form. As used herein, "isolated" means that the Triheterocyclic Compounds are separated from other components of either (a) a natural source, such as a plant or cell, preferably bacterial culture, or (b) a synthetic organic chemical reaction mixture. In another embodiment, via conventional techniques, the Triheterocyclic Compounds are purified. As used herein, "purified" means that when isolated, the isolate contains at least 95%, preferably at least 98%, of a single Triheterocyclic Compound by weight of the isolate.

As used herein, the term "T/C value" refers to the value obtained when: (a) the change from baseline in average tumor volume of treated mice is divided by the change from baseline in the average tumor volume of negative control mice; and (b) the numerical value obtained in step (a) is multiplied by 100.

It is recognized that Triheterocyclic Compounds of the invention can have one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding enantiomers and stereoisomers, that is, both the stereomerically pure form (e.g., geometrically pure, enantiomerically pure, or diastereomerically pure) and enantiomeric and stereoisomeric mixtures, e.g., racemates.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diasteroemers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

Enantiomeric and stereoisomeric mixtures of compounds of the invention can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

The following abbreviations and their definitions, unless defined otherwise, are used in this specification:

| Abbreviation | Definition |
| --- | --- |
| BOC | —C(O)OC(CH$_3$)$_3$ |
| DEF | N,N-diethylformamide |
| dppf | 1,1-bis(diphenylphosphino)ferrocene |
| DMF | N,N-dimethylformamide |
| DMSO | dimethylsulfoxide |
| THF | tetrahydrofuran |
| EtOAc | ethyl acetate |
| EtOH | ethanol |
| MeOH | methanol |
| Tf | —SO$_2$CF$_3$ |
| dba | dibenzylideneacetone |
| Ph | Phenyl |
| TBDMSCl | tert-Butyldimethylsilyl chloride |
| DBU | 1,8-diazabicyclo[5.4.0]undec-7-ene |
| LC/MS | Liquid Chromatography/Mass Spectrometry |

4. BRIEF DESCRIPTION OF THE DRAWINGS

FIG. 1 compares the effect of Compound 1 tartrate on the viability of the cancer cell lines H1299 and C33A and the normal cell lines HMEC and MRCS, as measured 72 hours post-treatment with 0.5 μM of Compound 1 tartrate.

Figure 4:
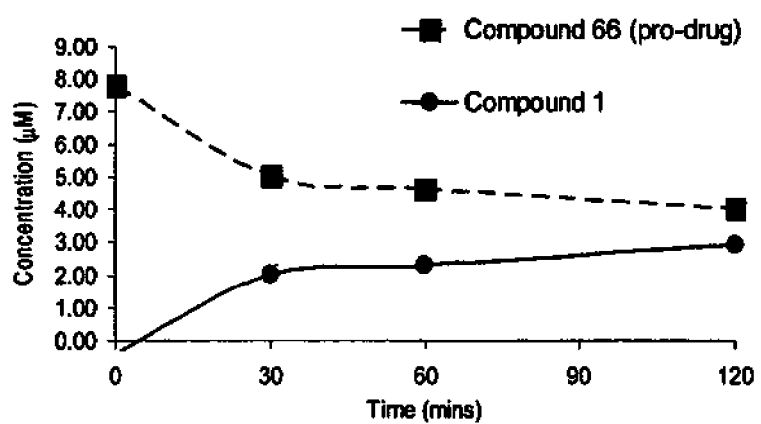

FIG. 4: Conversion of Compound 66 (Pro-Drug) into Compound 1 (Drug) over time in presence of purified human placental alkaline phosphatase.

Figure 5:
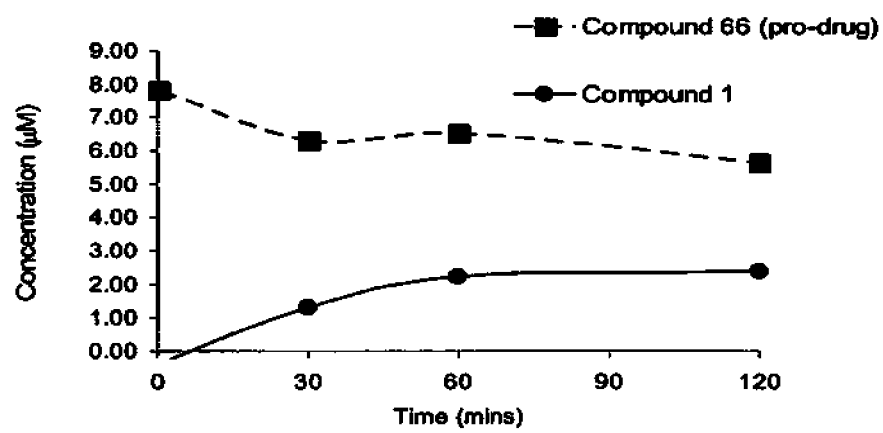

FIG. 5: Conversion of Compound 66 (Pro-Drug) into Compound 1 (Drug) over time in presence of purified calf intestinal phosphatase.

Figure 6:
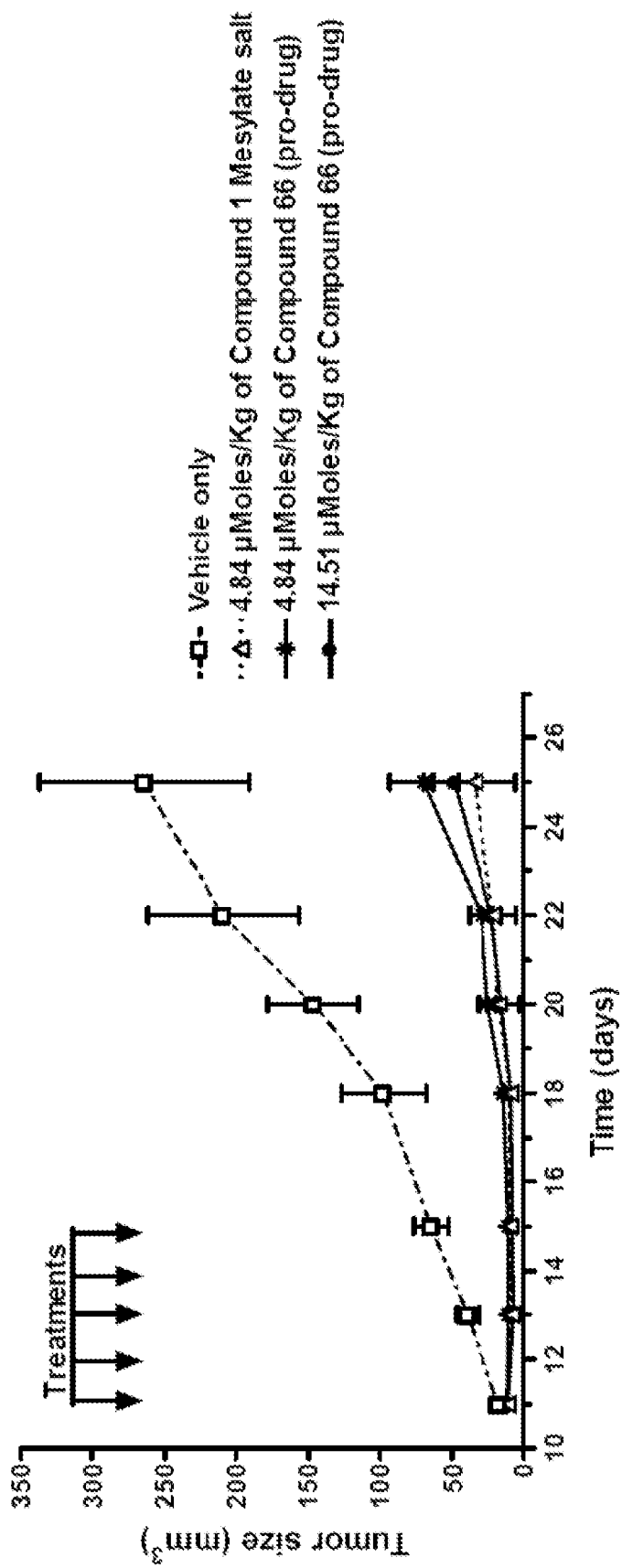

FIG. 6: The effect of Compound 1 Mesylate Salt and Compound 66 (pro-drug) on the growth of prostatic tumors in mice.

5. DETAILED DESCRIPTION OF THE INVENTION

5.1 The Triheterocyclic Compounds of Formula (Ia)

As stated above, the present invention encompasses compounds having the Formula (Ia)

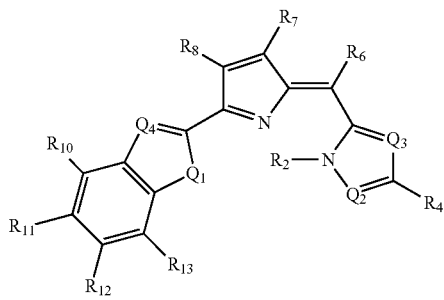

(Ia)

and pharmaceutically acceptable salts thereof, wherein:
$Q_1$-$Q_4$, $R_2$, $R_4$, $R_6$-$R_8$ and $R_{10}$-$R_{13}$ are defined above for the compounds of formula (Ia).

A first subclass of the Triheterocyclic Compounds of Formula (Ia) is that wherein:
$Q_1$ is —NH—;
$Q_2$ is —C($R_3$)—;
$Q_3$ is —C($R_5$)—; and
$Q_4$ is —C($R_9$)—.

A second subclass of the Triheterocyclic Compounds of Formula (Ia) is that wherein:
$Q_1$ is —O—;
$Q_2$ is —C($R_3$)—;
$Q_3$ is —C($R_5$)—; and
$Q_4$ is —C($R_9$)—.

A third subclass of the Triheterocyclic Compounds of Formula (Ia) is that wherein:
$Q_1$ is —S—;
$Q_2$ is —C($R_3$)—;
$Q_3$ is —C($R_5$)—; and
$Q_4$ is —C($R_9$)—.

A fourth subclass of the Triheterocyclic Compounds of Formula (Ia) is that wherein:
$Q_1$ is —NH—;
$Q_2$ is —N—;
$Q_3$ is —C($R_5$)—; and
$Q_4$ is —C($R_9$)—.

A fifth subclass of the Triheterocyclic Compounds of Formula (Ia) is that wherein:
$Q_1$ is —NH—;
$Q_2$ is —C($R_3$)—;
$Q_3$ is —N—; and
$Q_4$ is —C($R_9$)—.

A sixth subclass of the Triheterocyclic Compounds of Formula (Ia) is that wherein:
$Q_1$ is —NH—;
$Q_2$ is —C($R_3$)—;
$Q_3$ is —C($R_5$)—;
$Q_4$ is —CH—; and
$R_2$ and $R_6$ are —H.

A seventh subclass of the Triheterocyclic Compounds of Formula (Ia) is that wherein:
$Q_1$ is —NH—;
$Q_2$ is —C($R_3$)—;
$Q_3$ is —C($R_5$)—;
$Q_4$ is —CH—; and
$R_2$, $R_4$, $R_6$, $R_8$ and $R_{10}$-$R_{13}$ are —H.

An eighth subclass of the Triheterocyclic Compounds of Formula (Ia) is that wherein:
$Q_1$ is —NH—;
$Q_2$ is —C($C_1$-$C_8$ alkyl)-;
$Q_3$ is —C($C_1$-$C_8$ alkyl)-;
$Q_4$ is —CH—;
$R_2$, $R_4$, $R_6$, $R_8$ and $R_{10}$-$R_{13}$ are —H; and
$R_7$ is —O—($C_1$-$C_8$ alkyl).

An illustrative Triheterocyclic Compound of Formula (Ia) is:

Compound 1

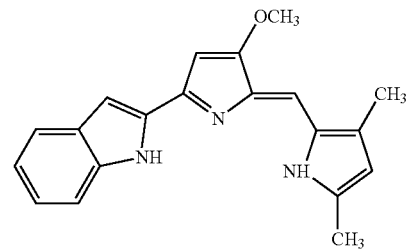

or a pharmaceutically acceptable salt thereof.

In one embodiment, Compound 1's pharmaceutically acceptable salt is a tartrate salt. In another embodiment, Compound 1's pharmaceutically acceptable salt is a mesylate salt.

Other illustrative Triheterocyclic Compound of Formula (Ia) are shown below:

Compound 1

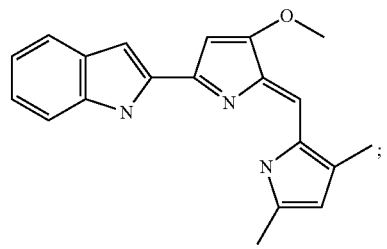

2-[5-(3,5-Dimethyl-1H-pyrrol-2-ylmethylene)-4-methoxy-5H-pyrrol-2-yl]-1H-indole

Compound 2

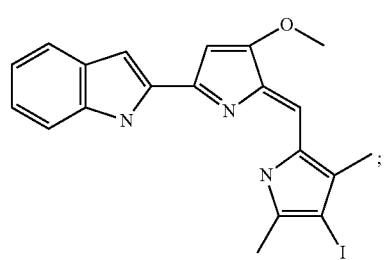

2-[5-(4-Iodo-3,5-dimethyl-1H-pyrrol-2-ylmethylene)-4-methoxy-5H-pyrrol-2-yl]-1H-indole Compound 3

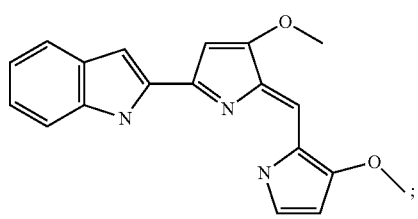

2-[4-Methoxy-5-(3-methoxy-1H-pyrrol-2-ylmethylene)-5H-pyrrol-2-yl]-1H-indole

Compound 4

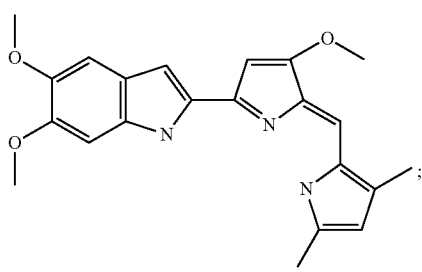

2-[5-(3,5-Dimethyl-1H-pyrrol-2-ylmethylene)-4-methoxy-5H-pyrrol-2-yl]-5,6-dimethoxy-1H-indole Compound 5

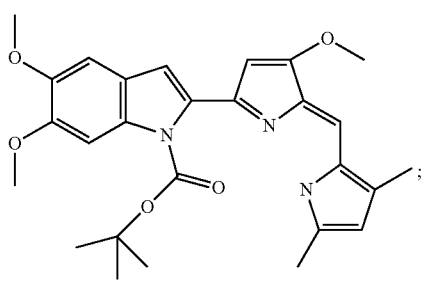

2-[5-(3,5-Dimethyl-1H-pyrrol-2-ylmethylene)-4-methoxy-5H-pyrrol-2-yl]-5,6-dimethoxy-indole-1-carboxylic acid tert-butyl ester Compound 6

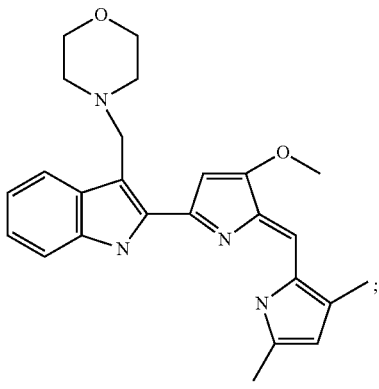

2-[5-(3,5-Dimethyl-1H-pyrrol-2-ylmethylene)-4-methoxy-5H-pyrrol-2-yl]-3-morpholin-4-ylmethyl-1H-indole Compound 7

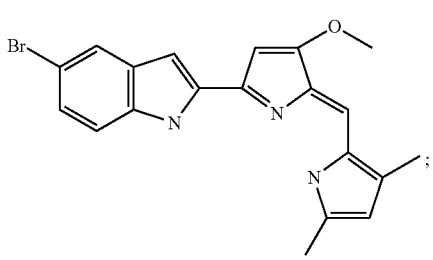

5-Bromo-2-[5-(3,5-dimethyl-1H-pyrrol-2-ylmethylene)-4-methoxy-5H-pyrrol-2-yl]-1H-indole Compound 8

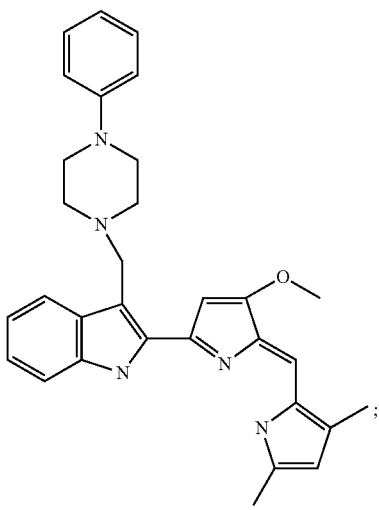

2-[5-(3,5-Dimethyl-1H-pyrrol-2-ylmethylene)-4-methoxy-5H-pyrrol-2-yl]-3-(4-phenyl-piperazin-1-ylmethyl)-1H-indole Compound 9

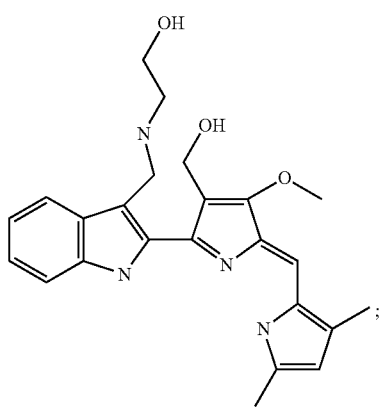

2-({2-[5-(3,5-Dimethyl-1H-pyrrol-2-ylmethylene)-3-hydroxymethyl-4-methoxy-5H-pyrrol-2-yl]-1H-indol-3-ylmethyl}-amino)-ethanol Compound 10

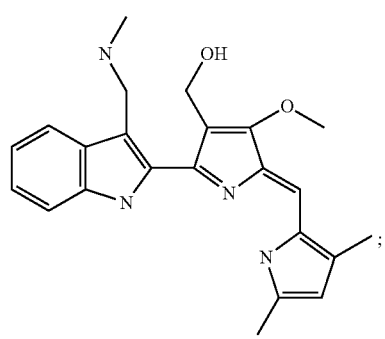

[5-(3,5-Dimethyl-1H-pyrrol-2-ylmethylene)-4-methoxy-2-(3-methylaminomethyl-1H-indol-2-yl)-5H-pyrrol-3-yl]-methanol Compound 11

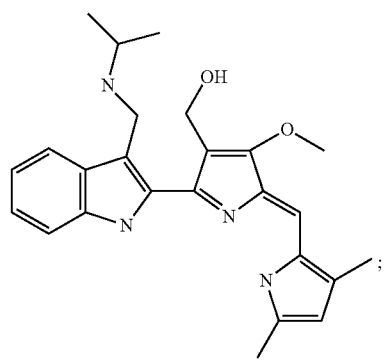

{5-(3,5-Dimethyl-1H-pyrrol-2-ylmethylene)-2-[3-(isopropylamino-methyl)-1H-indol-2-yl]-4-methoxy-5H-pyrrol-3-yl}-methanol Compound 12

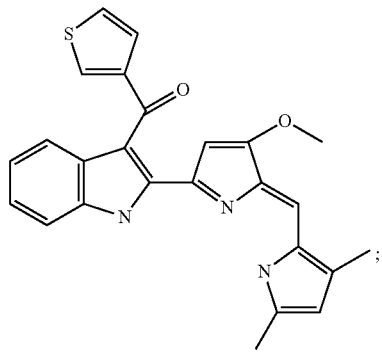

{2-[5-(3,5-Dimethyl-1H-pyrrol-2-ylmethylene)-4-methoxy-5H-pyrrol-2-yl]-1H-indol-3-yl}-thiophen-3-yl-methanone Compound 13

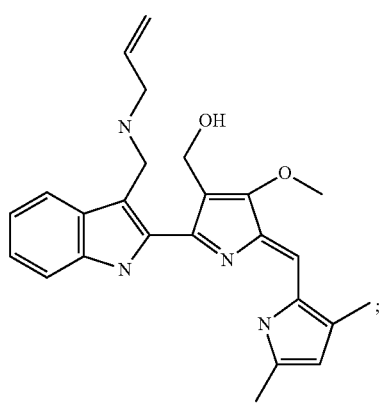

[2-(3-Allylaminomethyl-1H-indol-2-yl)-5-(3,5-dimethyl-1H-pyrrol-2-ylmethylene)-4-methoxy-5H-pyrrol-3-yl]-methanol Compound 14

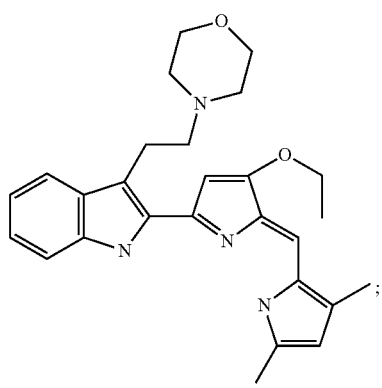

2-[5-(3,5-Dimethyl-1H-pyrrol-2-ylmethylene)-4-ethoxy-5H-pyrrol-2-yl]-3-(2-morpholin-4-yl-ethyl)-1H-indole Compound 15

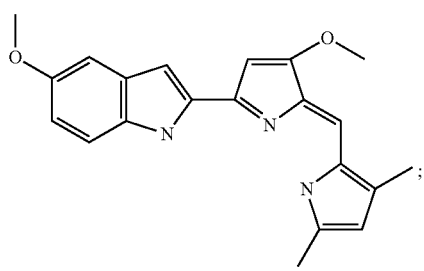

2-[5-(3,5-Dimethyl-1H-pyrrol-2-ylmethylene)-4-methoxy-5H-pyrrol-2-yl]-5-methoxy-1H-indole Compound 16

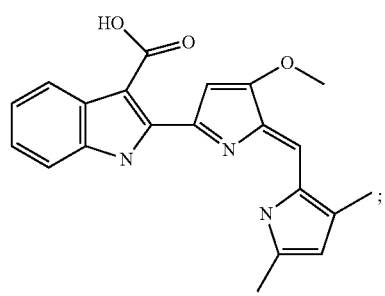

2-[5-(3,5-Dimethyl-1H-pyrrol-2-ylmethylene)-4-methoxy-5H-pyrrol-2-yl]-1H-indole-3-carboxylic acid Compound 17

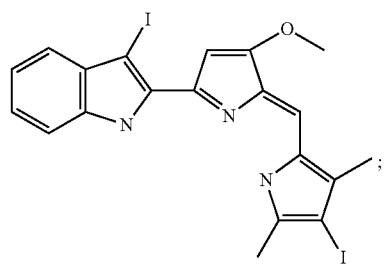

3-Iodo-2-[5-(4-iodo-3,5-dimethyl-1H-pyrrol-2-ylmethylene)-4-methoxy-5H-pyrrol-2-yl]-1H-indole Compound 18

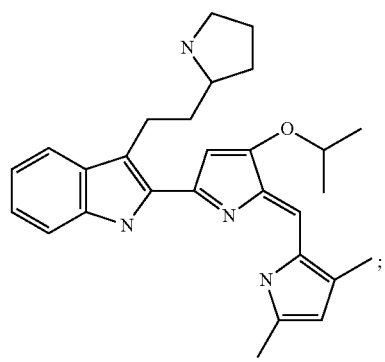

2-[5-(3,5-Dimethyl-1H-pyrrol-2-ylmethylene)-4-isopropoxy-5H-pyrrol-2-yl]-3-(2-pyrrolidin-2-yl-ethyl)-1H-indole Compound 19

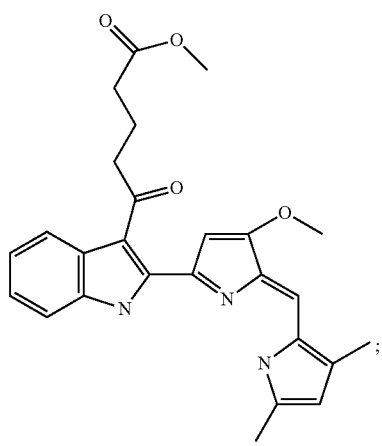

5-{2-5-(3,5-Dimethyl-1H-pyrrol-2-ylmethylene)-4-methoxy-5H-pyrrol-2-yl]-1H-indol-3-yl}-5-oxo-pentanoic acid methyl ester Compound 20

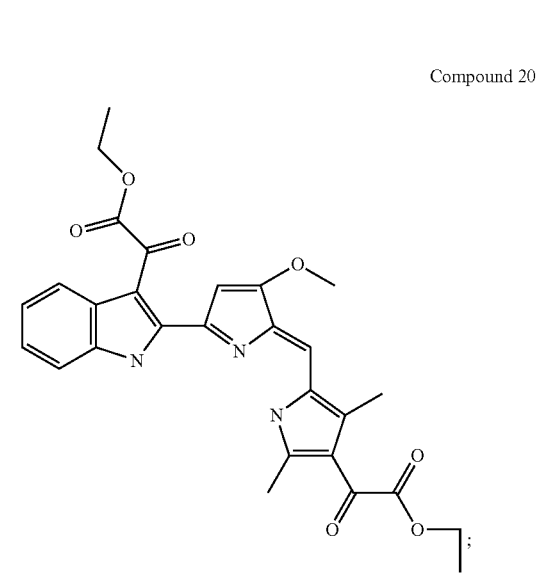

{2-[5-(4-Ethoxyoxalyl-3,5-dimethyl-1H-pyrrol-2-ylmethylene)-4-methoxy-5H-pyrrol-2-yl]-1H-indol-3-yl}-oxo-acetic acid ethyl ester Compound 21

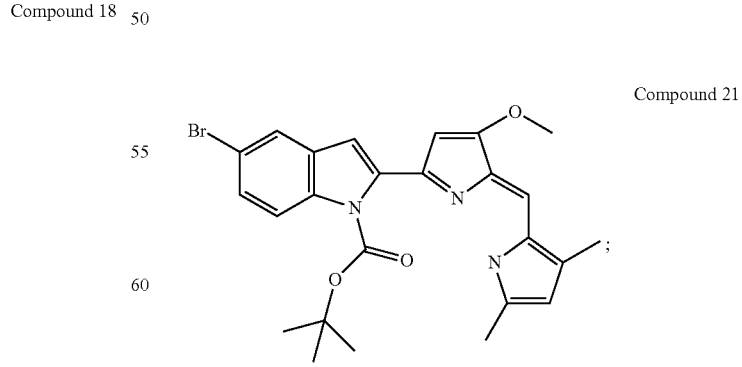

5-Bromo-2-[5-(3,5-dimethyl-1H-pyrrol-2-ylmethylene)-4-methoxy-5H-pyrrol-2-yl]-indole-1-carboxylic acid tert-butyl ester Compound 22

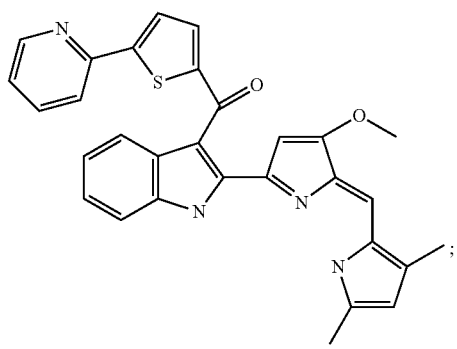

{2-[5-(3,5-Dimethyl-1H-pyrrol-2-
ylmethylene)-4-methoxy-5H-pyrrol-2-yl]-
1H-indol-3-yl}-(5-pyridin-2-yl-thiophen-2-
yl)-methanone Compound 23

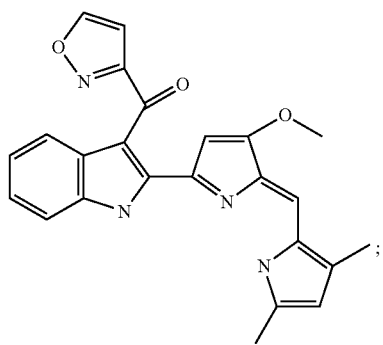

{2-[5-(3,5-Dimethyl-1H-pyrrol-2-
ylmethylene)-4-methoxy-5H-pyrrol-2-yl]-
1H-indol-3-yl}-isoxazol-3-yl-methanone Compound 24

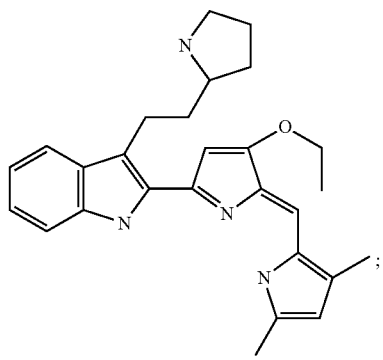

2-[5-(3,5-Dimethyl-1H-pyrrol-2-ylmethylene)-
4-ethoxy-5H-pyrrol-2-yl]-3-(2-pyrrolidin-2-yl-
ethyl)-1H-indole Compound 25

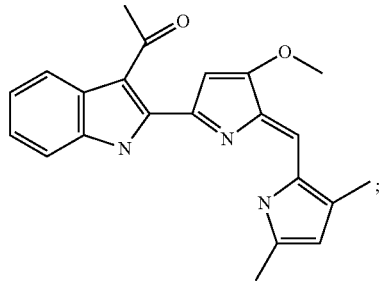

2-{2-[5-(3,5-Dimethyl-1H-pyrrol-2-
ylmethylene)-4-methoxy-5H-pyrrol-2-yl]-1H-
indol-3-yl}-ethanone Compound 26

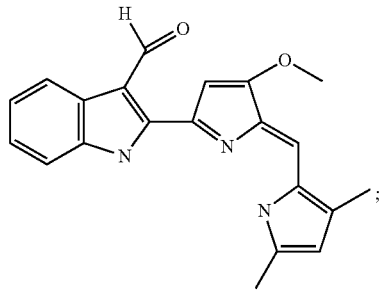

2-[5-(3,5-Dimethyl-1H-pyrrol-2-ylmethylene)-
4-methoxy-5H-pyrrol-2-yl]-1H-indole-3-
carbaldehyde Compound 27

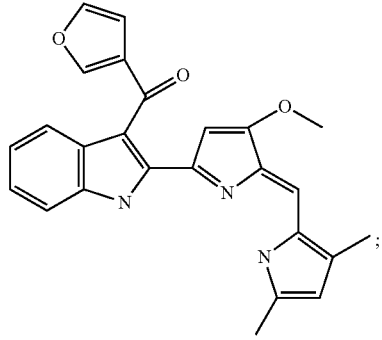

{2-[5-(3,5-Dimethyl-1H-pyrrol-2-
ylmethylene)-4-methoxy-5H-pyrrol-2-yl]-
1H-indol-3-yl}-furan-3-yl-methanone Compound 28

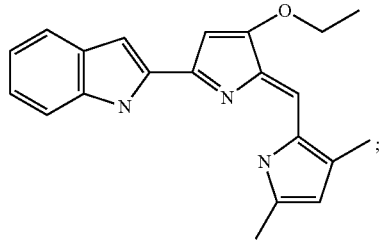

2-[5-(3,5-Dimethyl-1H-pyrrol-2-
ylmethylene)-4-ethoxy-5H-pyrrol-2-yl]-1H-
indole Compound 29

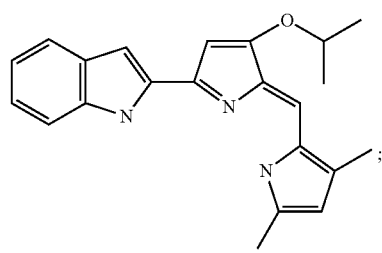

2-[5-(3,5-Dimethyl-1H-pyrrol-2-ylmethylene)-4-isopropoxy-5H-pyrrol-2-yl]-1H-indole Compound 30

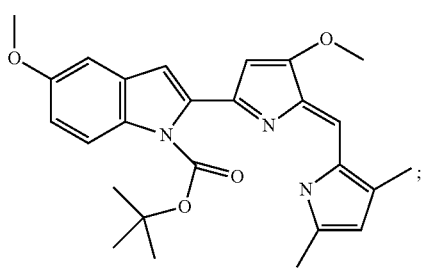

2-[5-(3,5-Dimethyl-1H-pyrrol-2-ylmethylene)-4-methoxy-5H-pyrrol-2-yl]-5-methoxy-indole-1-carboxylic acid tert-butyl ester Compound 31

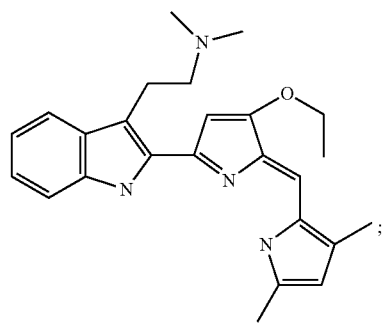

(2-{2-[5-(3,5-Dimethyl-1H-pyrrol-2-ylmethylene)-4-ethoxy-5H-pyrrol-2-yl]-1H-indol-3-yl}-ethyl)dimethyl-amine Compound 32

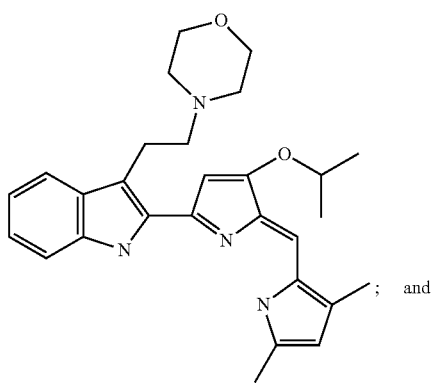

2-[5-(3,5-Dimethyl-1H-pyrrol-2-ylmethylene)-4-isopropoxy-5H-pyrrol-2-yl]-3-(2-morpholin-4-yl-ethyl)-1H-indole ; and Compound 33

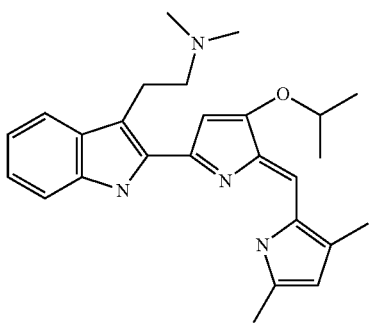

(2-{2-[5-(3,5-Dimethyl-1H-pyrrol-2-ylmethylene)-4-isopropoxy-5H-pyrrol-2-yl]-1H-indol-3-yl}-ethyl)dimethyl-amine Compound 34

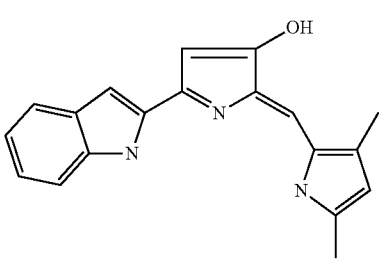

2-(3,5-Dimethyl-1H-pyrrol-2-ylmethylene)-5-(1H-indol-2-yl)-2H-pyrrol-3-ol

Compound 35

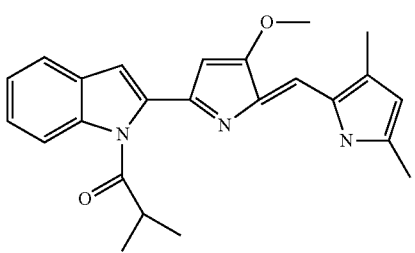

1-{2-[5-(3,5-Dimethyl-1H-pyrrol-2-ylmethylene)-4-methoxy-5H-pyrrol-2-yl]-indol-1-yl}-2-methyl-propan-1-one Compound 36

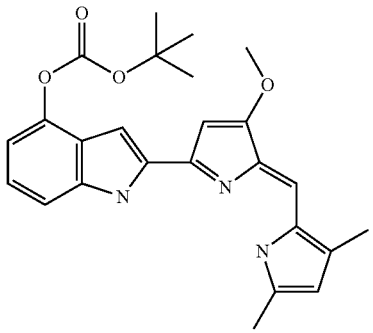

Carbonic acid tert-butyl ester 2-[5-(3,5-dimethyl-1H-pyrrol-2-ylmethylene)-4-methoxy-5H-pyrrol-2-yl]-1H-indol-4-yl ester Compound 37

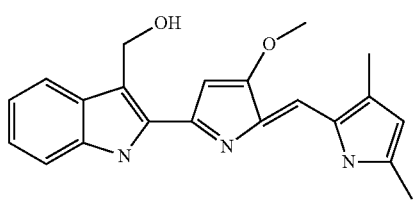

{2-[5-(3,5-Dimethyl-1H-pyrrol-2-ylmethylene)-4-methoxy-5H-pyrrol-2-yl]-1H-indol-3-yl}-methanol Compound 38

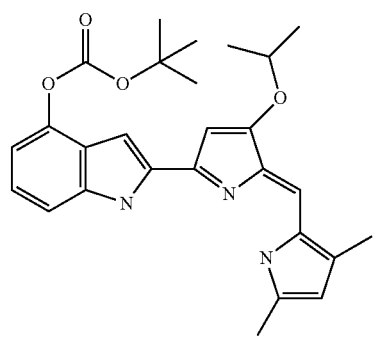

Carbonic acid tert-butyl ester 2-[5-(3,5-dimethyl-1H-pyrrol-2-ylmethylene)-4-isopropoxy-5H-pyrrol-2-yl]-1H-indol-4-yl ester Compound 39

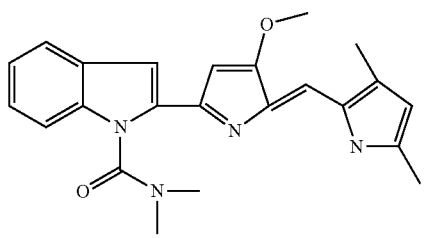

2-[5-(3,5-Dimethyl-1H-pyrrol-2-ylmethylene)-4-methoxy-5H-pyrrol-2-yl]-indole-1-carboxylic acid dimethylamide Compound 40

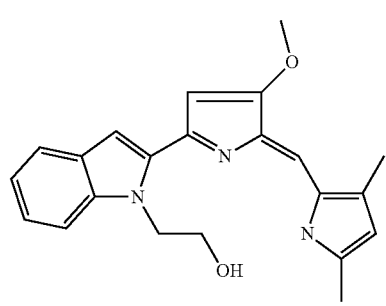

2-{2-[5-(3,5-Dimethyl-1H-pyrrol-2-ylmethylene)-4-methoxy-5H-pyrrol-2-yl]-indol-1-yl}-ethanol Compound 41

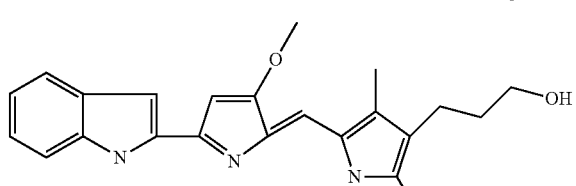

3-{5-[5-(1H-indol-2-yl)-3-methoxy-pyrrol-2-ylidenemethyl]-2,4-dimethyl-1H-pyrrol-3-yl}-propan-1-ol Compound 42

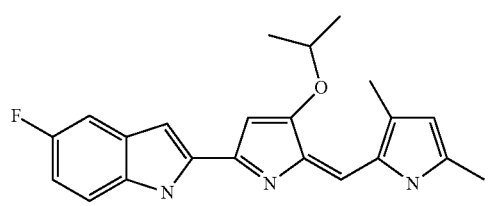

2-[5-(3,5-Dimethyl-1H-pyrrol-2-ylmethylene)-4-isopropoxy-5H-pyrrol-2-yl]-5-fluoro-1H-indole Compound 43

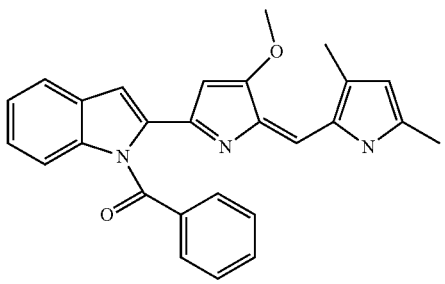

{2-[5-(3,5-Dimethyl-1H-pyrrol-2-ylmethylene)-4-methoxy-5H-pyrrol-2-yl]-indol-1-yl}-phenyl-methanone Compound 44

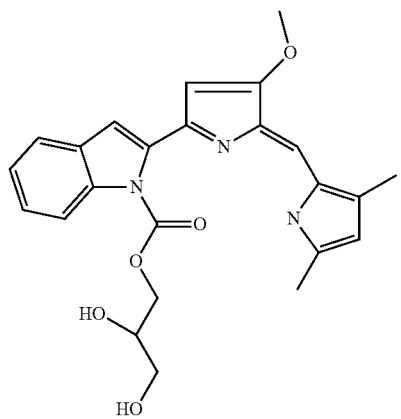

2-[5-(3,5-Dimethyl-1H-pyrrol-2-ylmethylene)-4-methoxy-5H-pyrrol-2-yl]-indole-1-carboxylic acid 2,3-dihydroxy-propyl ester -continued Compound 45

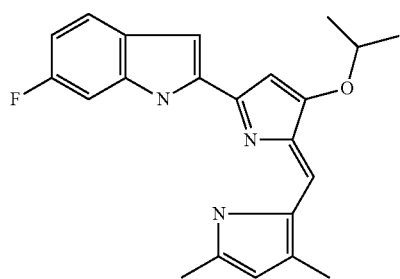

2-[5-(3,5-Dimethyl-1H-pyrrol-2-ylmethylene)-
4-isopropoxy-5H-pyrrol-2-yl]-
6-fluoro-1H-indole Compound 46

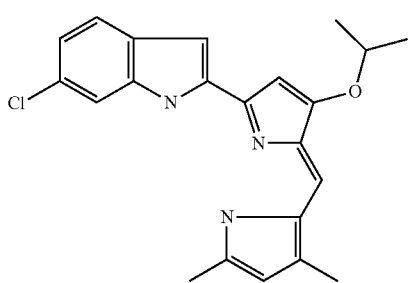

6-Chloro-2-[5-(3,5-dimethyl-1H-pyrrol-
2-ylmethylene)-4-isopropoxy-5H-
pyrrol-2-yl]-1H-indole Compound 47

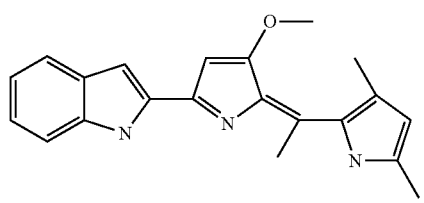

2-{5-[1-(3,5-Dimethyl-1H-pyrrol-2-yl)-
ethylidene]-4-methoxy-5H-pyrrol-
2-yl}-1H-indole Compound 48

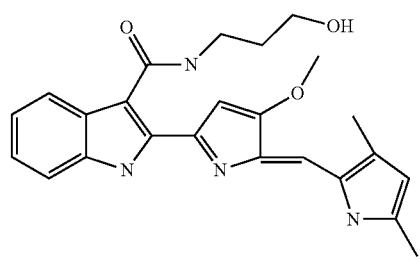

2-[5-(3,5-Dimethyl-1H-pyrrol-2-ylmethylene)-
4-methoxy-5H-pyrrol-2-yl]-
1H-indole-3-carboxylic acid (3-hydroxy-
propyl)-amide -continued Compound 49

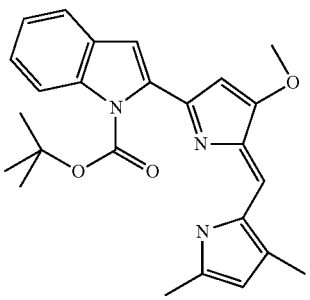

2-[5-(3,5-Dimethyl-1H-pyrrol-2-ylmethylene)-
4-methoxy-5H-pyrrol-2-yl]-
indole-1-carboxylic acid tert-butyl
ester Compound 50

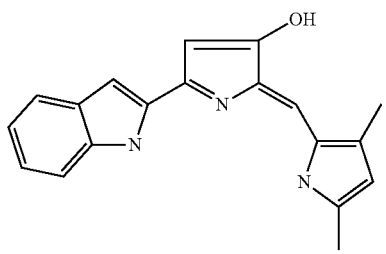

2-(3,5-Dimethyl-1H-pyrrol-2-ylmethylene)-
5-(1H-indol-2-yl)-2H-pyrrol-3-ol

Compound 51

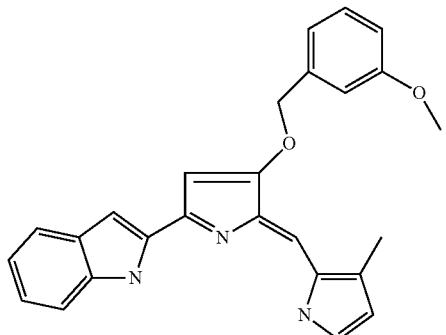

2-[5-(3,5-Dimethyl-1H-pyrrol-2-
ylmethylene)-4-(3-methoxy-benzyloxy)-5H-
pyrrol-2-yl]-1H-indole Compound 52

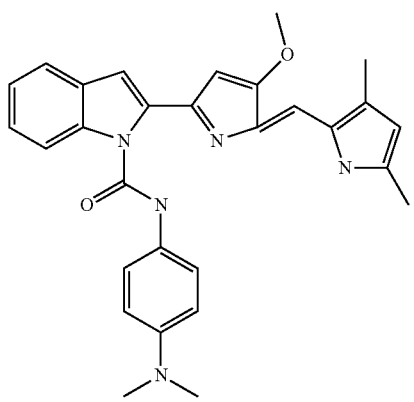

2-[5-(3,5-Dimethyl-1H-pyrrol-2-ylmethylene)-
4-methoxy-5H-pyrrol-2-yl]-
indole-1-carboxylic acid (4-dimethylamino-
phenyl)-amide Compound 53

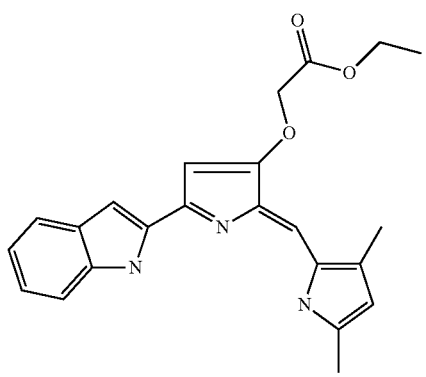

[2-(3,5-Dimethyl-1H-pyrrol-2-ylmethylene)-
5-(1H-indol-2-yl)-2H-pyrrol-
3-yloxy]-acetic acid ethyl ester Compound 54

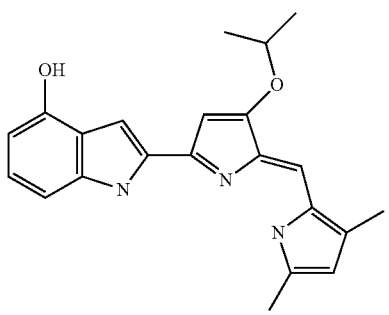

2-[5-(3,5-Dimethyl-1H-pyrrol-2-ylmethylene)-
4-methoxy-5H-pyrrol-2-yl]-
indole-1-carboxylic acid (4-benzyloxy-
phenyl)-amide Compound 55

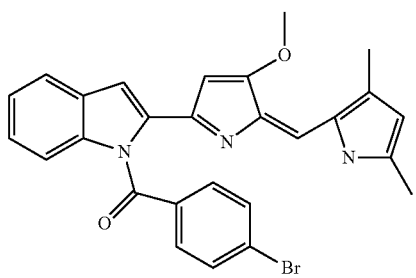

(4-Bromo-phenyl)-{2-[5-(3,5-dimethyl-
1H-pyrrol-2-ylmethylene)-4-methoxy-
5H-pyrrol-2-yl]-indol-1-yl}-methanone Compound 56

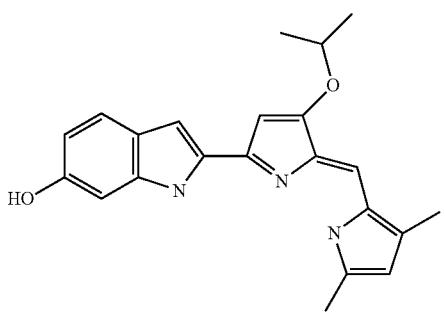

2-[5-(3,5-Dimethyl-1H-pyrrol-2-ylmethylene)-
4-isopropoxy-5H-pyrrol-2-yl]-
1H-indol-6-ol Compound 57

2-[5-(3,5-Dimethyl-1H-pyrrol-2-ylmethylene)-
4-isopropoxy-5H-pyrrol-2-yl]-
1H-indol-4-ol Compound 58

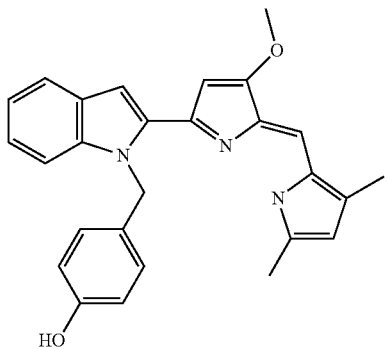

4-{2-[5-(3,5-Dimethyl-1H-pyrrol-2-
ylmethylene)-4-methoxy-5H-pyrrol-2-yl]-
indol-1-ylmethyl}-phenol Compound 59

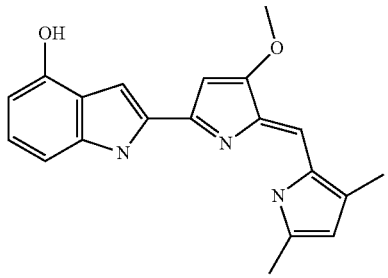

2-[5-(3,5-Dimethyl-1H-pyrrol-2-ylmethylene)-
4-methoxy-5H-pyrrol-2-yl]-
1H-indol-4-ol Compound 60

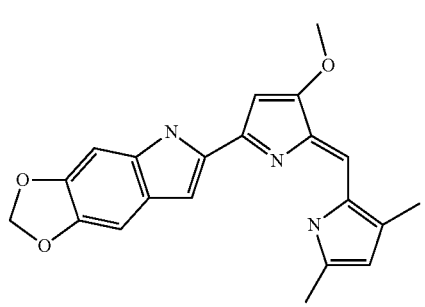

6-[5-(3,5-Dimethyl-1H-pyrrol-2-ylmethylene)-
4-methoxy-5H-pyrrol-2-yl]-
5H-[1,3]dioxolo[4,5-f]indole Compound 61

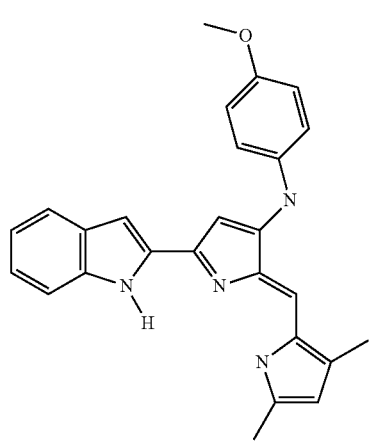

[2-(3,5-Dimethyl-1H-pyrrol-2-ylmethylene)-
5-(1H-indol-2-yl)-2H-pyrrol-
3-yl]-(4-methoxy-phenyl)-amine Compound 62

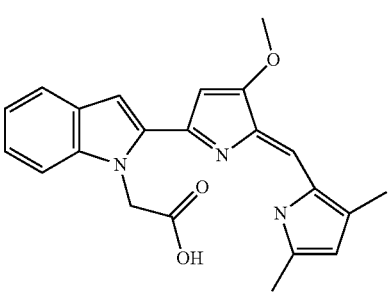

{2-[5-(3,5-Dimethyl-1H-pyrrol-2-ylmethylene)-
4-methoxy-5H-pyrrol-2-yl]-
indol-1-yl}-acetic acid Compound 63

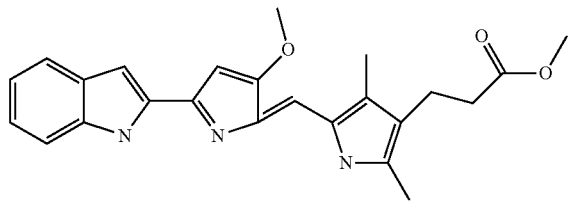

3-{5-[5-(1H-Indol-2-yl)-3-methoxy-
pyrrol-2-ylidenemethyl]-2,4-dimethyl-
1H-pyrrol-3-yl}-propionic acid methyl ester Compound 64

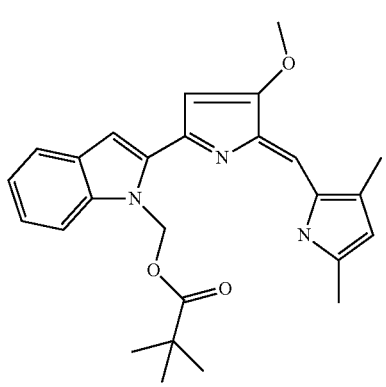

2,2-Dimethyl-propionic acid 2-[5-(3,5-
dimethyl-1H-pyrrol-2-ylmethylene)-
4-methoxy-5H-pyrrol-2-yl]-indol-1-
ylmethyl ester Compound 65

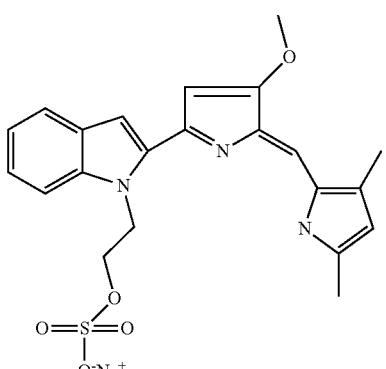

Sodium salt of Sulfuric acid mono-
(2-{2-[5-(3,5-dimethyl-1H-pyrrol-
2-ylmethylene)-4-methoxy-5H-
pyrrol-2-yl]-indol-1-yl}-ethyl) ester and pharmaceutically acceptable salts thereof.

5.2 The Triheterocyclic Compounds of Formula (Ib)

As stated above, the present invention encompasses compounds having the Formula (Ia)

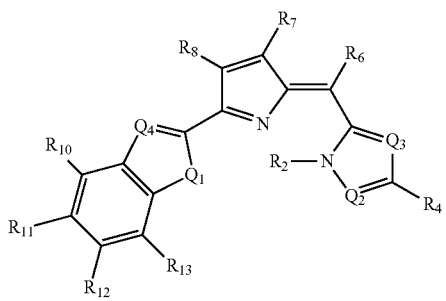

(Ib)

and pharmaceutically acceptable salts thereof, wherein:
$Q_1$-$Q_4$, $R_2$, $R_4$, $R_6$-$R_8$ and $R_{10}$-$R_{13}$ are defined above for the compounds of formula (b).

The present invention also provides compositions comprising a pharmaceutically acceptable carrier and an effective amount of a Triheterocyclic Compound of Formula (Ib) or a pharmaceutically acceptable salt thereof.

The invention further provides methods for treating or preventing cancer or neoplastic disease, comprising administering to a patient in need of such treatment or prevention an effective amount of a Triheterocyclic Compound of Formula (Ia) or (Ib).

The invention further provides methods for inhibiting the growth of a cancer or neoplastic cell, comprising contacting the cancer or neoplastic cell with an effective amount of a Triheterocyclic Compound of Formula (Ia) or (Ib).

The invention further provides methods for treating or preventing a viral infection, comprising administering to a patient in need of such treatment or prevention an effective Amount of a Triheterocyclic Compound of Formula (Ia or Ib).

The invention further provides methods for inhibiting the replication or infectivity of a virus, comprising contacting a virus or a virus-infected cell with an effective amount of a Triheterocyclic Compound of Formula (Ia) or (Ib).

A first subclass of the Triheterocyclic Compounds of Formula (Ib) is that wherein:
$Q_1$ is —NH—;
$Q_2$ is —C($R_3$)—;
$Q_3$ is —C($R_5$)—; and
$Q_4$ is —C($R_9$)—.

A second subclass of the Triheterocyclic Compounds of Formula (Ib) is that wherein:
$Q_1$ is —O—;
$Q_2$ is —C($R_3$)—;
$Q_3$ is —C($R_5$)—; and
$Q_4$ is —C($R_9$)—.

A third subclass of the Triheterocyclic Compounds of Formula (Ib) is that wherein:
$Q_1$ is —S—;
$Q_2$ is —C($R_3$)—;
$Q_3$ is —C($R_5$)—; and
$Q_4$ is —C($R_9$)—.

A fourth subclass of the Triheterocyclic Compounds of Formula (Ib) is that wherein:
$Q_1$ is —NH—;
$Q_2$ is —N—;
$Q_3$ is —C($R_5$)—; and
$Q_4$ is —C($R_9$)—.

A fifth subclass of the Triheterocyclic Compounds of Formula (Ib) is that wherein:
$Q_1$ is —NH—;
$Q_2$ is —C($R_3$)—;
$Q_3$ is —N—; and
$Q_4$ is —C($R_9$)—.

A sixth subclass of the Triheterocyclic Compounds of Formula (Ib) is that wherein:
$Q_1$ is —NH—;
$Q_2$ is —C($R_3$)—;
$Q_3$ is —C($R_5$)—;
$Q_4$ is —CH—; and
$R_2$ and $R_6$ are —H.

A seventh subclass of the Triheterocyclic Compounds of Formula (Ib) is that wherein:
$Q_1$ is —NH—;
$Q_2$ is —C($R_3$)—;
$Q_3$ is —C($R_5$)—;
$Q_4$ is —CH—; and
$R_2$, $R_4$, $R_6$, $R_8$ and $R_{10}$-$R_{13}$ are —H.

An eighth subclass of the Triheterocyclic Compounds of Formula (Ib) is that wherein:
$Q_1$ is —NH—;
$Q_2$ is —C($C_1$-$C_8$ alkyl)-;
$Q_3$ is —C($C_1$-$C_8$ alkyl)-;
$Q_4$ is —CH—;
$R_2$, $R_4$, $R_6$, $R_8$ and $R_{10}$-$R_{13}$ are —H; and
$R_7$ is —O—($C_1$-$C_8$ alkyl).

In one embodiment, the invention provides a composition comprising a pharmaceutically acceptable carrier and Compound 1 or a pharmaceutically acceptable salt thereof. In another embodiment, the pharmaceutically acceptable salt is a tartrate salt. In even another embodiment, the pharmaceutically acceptable salt is a mesylate salt.

In other embodiments, a compound useful in the present methods is Compound 1 or a pharmaceutically acceptable salt thereof. In another embodiment, the pharmaceutically acceptable salt is a tartrate salt. In even another embodiment, the pharmaceutically acceptable salt is a mesylate salt.

5.3 The Triheterocyclic Compounds of Formula II

As stated above, the present invention encompasses novel compounds having the Formula (II)

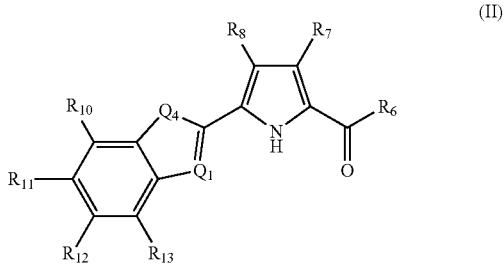

(II)

and pharmaceutically acceptable salts thereof, wherein:
$Q_1$, $Q_4$, $R_6$-$R_8$ and $R_{10}$-$R_{13}$ are defined above for the compounds of Formula (II).

A first subclass of the Triheterocyclic Compounds of Formula (II) is that wherein:
$Q_1$ is —NH—; and
$Q_4$ is —C($R_9$)—.

A second subclass of the Triheterocyclic Compounds of Formula (II) is that wherein:
$Q_1$ is —O—; and
$Q_4$ is —C($R_9$)—.

A third subclass of the Triheterocyclic Compounds of Formula (II) is that wherein:
$Q_1$ is —S—; and
$Q_4$ is —C($R_9$)—.

A fourth subclass of the Triheterocyclic Compounds of Formula (II) is that wherein:
$Q_1$ is —NH—;
$Q_4$ is —CH—; and
$R_6$ is —H.

A fifth subclass of the Triheterocyclic Compounds of Formula (II) is that wherein:
$Q_1$ is —NH—;
$Q_4$ is —CH—;
$R_6$ is —H; and
$R_{10}$-$R_{13}$ are —H.

A sixth subclass of the Triheterocyclic Compounds of Formula (II) is that wherein:
$Q_1$ is —NH—;
$Q_4$ is —CH—;
$R_6$ is —H;
$R_8$ and $R_{10}$-$R_{13}$ are —H; and
$R_7$ is —O—($C_1$-$C_8$ alkyl).

The present invention also provides compositions comprising a pharmaceutically acceptable carrier and an effective amount of a compound of Formula (II) or a pharmaceutically acceptable salt thereof.

The invention further provides methods for treating or preventing cancer or neoplastic disease, comprising administering to a patient in need of such treatment or prevention an effective amount of a Triheterocyclic Compound of Formula (II).

The invention further provides methods for inhibiting the growth of a cancer or neoplastic cell, comprising contacting the cancer or neoplastic cell with an effective amount of a Triheterocyclic Compound of Formula (II).

The invention further provides methods for treating or preventing a viral infection, comprising administering to a patient in need of such treatment or prevention an effective amount of a Triheterocyclic Compound of Formula (II).

The invention further provides methods for inhibiting the replication or infectivity of a virus, comprising contacting a virus or a virus-infected cell with an effective amount of a Triheterocyclic Compound of Formula (II).

5.4 Methods for Making the Triheterocyclic Compounds

The invention further provides methods useful for making Triheterocyclic Compounds.

The compounds of the invention can be obtained via standard, well-known synthetic methodology, see e.g. March, J. *Advanced Organic Chemistry; Reactions Mechanisms, and Structure*, 4th ed., 1992. Illustrative methods are described below. Starting materials useful for preparing the compounds of the invention and intermediates therefore, are commercially available or can be prepared from commercially available materials using known synthetic methods and reagents.

An example of a synthetic pathways useful for making the Triheterocyclic Compounds is set forth below and generalized in Scheme 1.

The Triheterocyclic Compounds can be obtained via conventional organic synthesis, e.g., as described below. Scheme 1 indicates a general method by which the Triheterocyclic Compounds can be obtained, wherein $Q_1$-$Q_4$, $R_2$, $R_4$, $R_6$-$R_8$ and $R_{10}$-$R_{13}$ are defined above for the Triheterocyclic Compounds of Formulas (Ia), (Ib) and (II).

Scheme 1

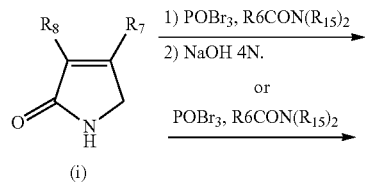

(i)

-continued

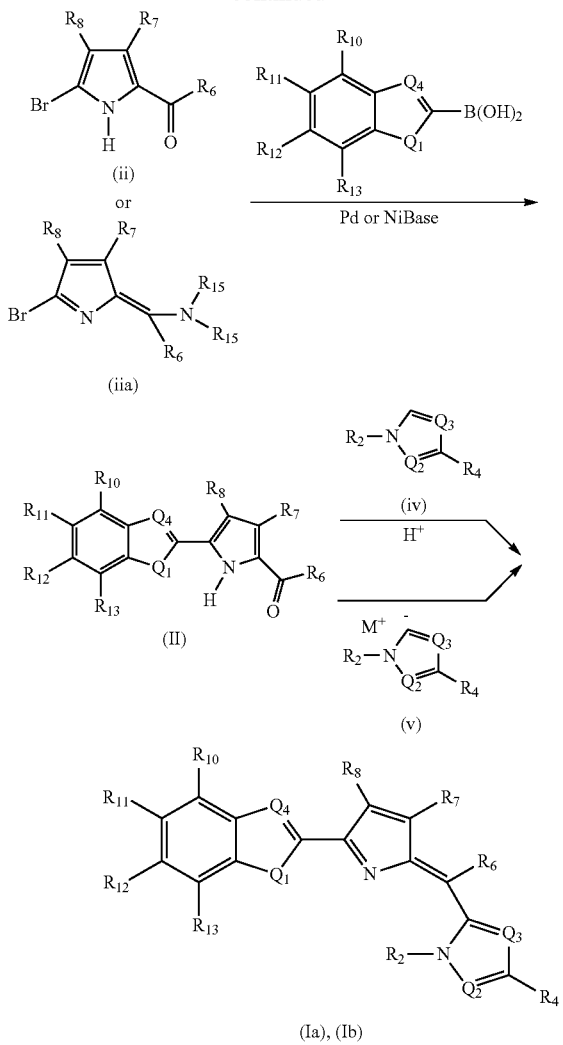

For example, a commercially available or synthetically prepared pyrrolidinone of Formula (i) is subjected to a Vilsmeier formylation in the presence of phosphoryl bromide and alkyl formamide to provide a brominated pyrrolyl aldehyde of Formula (II) or brominated pyrrolyl enamine (iia). The compound of Formula (ii) or (iia) is then subjected to a palladium or nickel-catalyzed cross-coupling reaction with a boronic acid of Formula (iii) to provide a diheterocyclic Compound of Formula (II). The Compound of Formula (II) is then coupled under acidic conditions with a pyrrole of Formula (iv) to provide a Compound of Formula (Ia) or (Ib). In an alternate embodiment, the Compound of Formula (II) is condensed with a Compound of Formula (v) (an anion of a Compound of Formula (iv)) to provide a Compound of Formula (Ia) or (Ib).

5.4.1 Making the Compounds of Formula (Ia) from the Compounds of Formula (II) Via Acid Mediated Coupling In one particular embodiment, the invention provides methods for making Triheterocyclic Compounds of Formula (Ia)

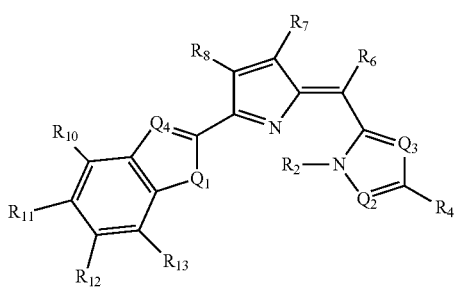
(Ia)

comprising contacting a compound of Formula (II)

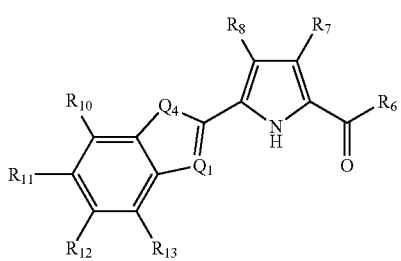
(II)

with a compound of Formula (iv)

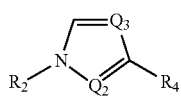
(iv)

in the presence of an organic solvent and a protic acid, for a time and at a temperature sufficient to make the compound of Formula (Ia)

wherein $Q_1$-$Q_4$, $R_2$, $R_4$, $R_6$-$R_8$ and $R_{10}$-$R_{13}$ are defined above for the Triheterocyclic Compounds of Formula (Ia).

The formation of a Triheterocyclic Compound of Formula (Ia) can be monitored using conventional analytical techniques, including, but not limited to, thin-layer chromatography ("TLC"), high-performance liquid chromatography ("HPLC"), gas chromatography ("GC"), and nuclear magnetic resonance spectroscopy ("NMR") such as $^1$H or $^{13}$C NMR.

The concentration of the Triheterocyclic Compound of Formula (II) in the reaction mixture typically ranges from about 0.01 moles to about 3 moles per liter of the reaction mixture. In one embodiment, the concentration of the Triheterocyclic Compound of Formula (II) in the reaction mixture ranges from about 0.05 moles to about 1 mole per liter of the reaction mixture. In another embodiment, the concentration of the Triheterocyclic Compound of Formula (II) in the reaction mixture ranges from about 0.1 mole to about 0.5 moles per liter of the reaction mixture.

The amount of Compound of Formula (iv) in the reaction mixture is typically present in at least about a 1.5-fold molar excess to about a 10-fold molar excess relative to the amount of the Triheterocyclic Compound Formula (II). In one embodiment, the amount of Compound of Formula (iv) in the reaction mixture is at least about a 2-fold molar excess to about a 10-fold molar excess relative to the amount of the Triheterocyclic Compound of Formula (II). In another embodiment, the amount of Compound of Formula (iv) in the reaction mixture is at least about a 3-fold molar excess to about a 10-fold molar excess relative to the amount of the Triheterocyclic Compound of Formula (II).

The amount of protic acid in the reaction mixture typically ranges from about 0.0001 to about 5 molar equivalents per equivalent of the Triheterocyclic Compound of Formula (II). In another embodiment, the amount of protic acid in the reaction mixture ranges from about 0.001 to about 3 molar equivalents per equivalent of the Triheterocyclic Compound of Formula (II). In another embodiment, the amount of protic acid in the reaction mixture ranges from about 0.01 to about 1 molar equivalents per equivalent of the Triheterocyclic Compound of Formula (II).

Suitable protic acids for use in the methods of the invention include, but are not limited to, hydrochloric acid, hydrobromic acid, hydroiodic acid, hydrofluoric acid, sulfuric acid, perchloric acid, nitric acid, methanesulfonic acid, ethanesulfonic acid, trifluoromethanesulfonic acid, benzenesulfonic acid, p-toluenesulfonic acid, p-bromobenzenesulfonic acid, p-nitrobenzenesulfonic acid, p-trifluoromethylbenzenesulfonic acid, mixtures thereof and aqueous mixtures thereof. In one embodiment, the protic acid is aqueous hydrochloric acid or aqueous hydrobromic acid.

The reaction mixture further comprises an organic solvent. Suitable organic solvents include, but are not limited to alcohols, such as methanol, ethanol, isopropanol and tert-butanol; and ethers, such as diethyl ether, diisopropyl ether, THF and dioxane. In one embodiment, the solvent is methanol or ethanol.

In one embodiment, the reaction mixture is substantially anhydrous.

The amount of organic solvent in the reaction mixture is typically present at an amount of at least about 10 molar equivalents per equivalent of the Triheterocyclic Compound of Formula (II). In one embodiment, the organic solvent is present in the reaction mixture in an amount that is at least about 20 molar equivalents per equivalent of the Triheterocyclic Compound of Formula (II). In another embodiment, the organic solvent is present in the reaction mixture in an amount that is at least about 30 molar equivalents per equivalent of the Triheterocyclic Compound of Formula (II). In another embodiment, the organic solvent is present in the reaction mixture in an amount that is at least about 40 molar equivalents per equivalent of the Triheterocyclic Compound of Formula (II). In one embodiment, the organic solvent is present in the reaction mixture in an amount that ranges from about a 10 molar equivalents to about 1,000 molar equivalents per equivalent of the Triheterocyclic Compound of Formula (II). In another embodiment, the organic solvent is present in the reaction mixture in an amount that ranges from about a 20 molar equivalents to about 1,000 molar equivalents per equivalent of the Triheterocyclic Compound of Formula (II). In another embodiment, the organic solvent is present in the reaction mixture in an amount that ranges from about a 30 molar equivalents to about 1,000 molar equivalents per equivalent of the Triheterocyclic Compound of Formula (II). In another embodiment, the organic solvent is present in the reaction mixture in an amount that ranges from about a 40 molar equivalents to about 1,000 molar equivalents per equivalent of the Triheterocyclic Compound of Formula (II).

Typically, the reaction proceeds for a time ranging from about 5 minutes to about 20 hours. In one embodiment, the reaction proceeds for a time ranging from about 10 minutes hour to about 10 hours. In another embodiment, the reaction proceeds for a time ranging from about 30 minutes to about 2 hours.

Typically, the reaction temperature ranges from about 25° C. to about 100° C. In one embodiment, the reaction temperature ranges from about 25° C. to about 40° C. In another embodiment, the reaction temperature is at about room temperature.

Typically, the overall yield of the isolated and purified Triheterocyclic Compound of Formula (Ia) is greater than about 70 percent based on the amount of the Triheterocyclic Compound of Formula (II) or on the amount of the Compound of Formula (iv). In one embodiment, the overall yield of the isolated and purified Triheterocyclic Compound of Formula (Ia) is greater than about 75 percent based on the amount of the Triheterocyclic Compound of Formula (II) or on the amount of the Compound of Formula (iv). In another embodiment, the overall yield of the isolated and purified Triheterocyclic Compound of Formula (Ia) is greater than about 80 percent based on the amount of the Triheterocyclic Compound of Formula (II) or on the amount of the Triheterocyclic Compound of Formula (iv).

5.4.2 Method for Making the Compounds of Formula (Ia) from the Compounds of Formula (II) Via a Condensation Reaction In another embodiment, the invention provides methods for making a Compound of Formula (Ia) comprising the steps:

(a) contacting a compound of Formula (II)

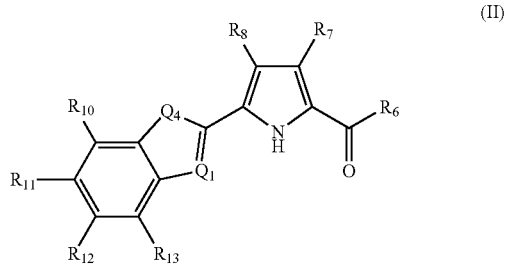

with a compound of Formula (v)

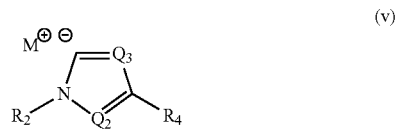

wherein M is Li, Na, K, Rb or Cs, in the presence of a substantially anhydrous, aprotic organic solvent, for a time and at a temperature sufficient to make a compound of Formula (vi),

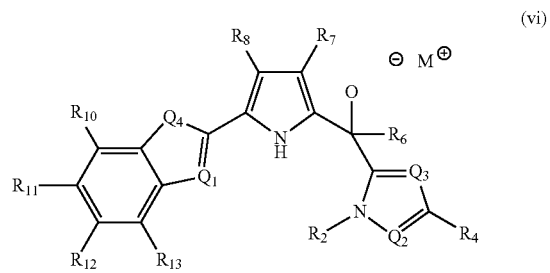

wherein M is defined as above; and (b) protonating the compound of Formula (vi) with an H+ donor for a time and at a temperature sufficient to make the compound of Formula (Ia), wherein $Q_1$-$Q_4$, $R_2$, $R_4$, $R_6$-$R_8$ and $R_{10}$-$R_{13}$ are defined above for the compounds of formula (Ia).

The formation of a Triheterocyclic Compound of Formula (Ia) can be monitored using conventional analytical techniques, including, but are not limited to, TLC, HPLC, GC, and NMR, such as $^1$H or $^{13}$C NMR.

The concentration of the Triheterocyclic Compound of Formula (II) in the reaction mixture typically ranges from about 0.01 moles to about 3 moles per liter of the reaction mixture. In one embodiment, the concentration of the Triheterocyclic Compound of Formula (II) in the reaction mixture ranges from about 0.05 moles to about 1 mole per liter of the reaction mixture. In another embodiment, the concentration of the Triheterocyclic Compound of Formula (II) in the reaction mixture ranges from about 0.1 mole to about 0.5 moles per liter of the reaction mixture.

The amount of Compound of Formula (v) in the reaction mixture is typically between about an equimolar amount and about a 2-fold molar excess relative to an equivalent amount of the Triheterocyclic Compound of Formula (II). In one embodiment, the amount of Compound of Formula (v) in the reaction mixture is about equimolar relative to the amount of the Triheterocyclic Compound of Formula (II).

In one embodiment, the reaction mixture is substantially anhydrous.

A Compound of Formula (v) can be prepared by deprotonating a Compound of Formula (iv) with a base, such as n-butyllithium, using methods that are well-known to those of skill in the art of organic synthesis. For examples of methods useful for preparing a Compound of Formula (v) from a Compound of Formula (iv) using a base, see Martinez et al., *J. Org. Chem.*, 46, 3760 (1981) and Minato et al., *Tetrahedron Lett.*, 22:5319 (1981).

The reaction mixture also comprises a substantially anhydrous, aprotic organic solvent. Suitable aprotic solvents include, but are not limited to THF, DMF, DMSO, N-methylpyrrolidinone and diethyl ether. Such aprotic solvents may be made substantially anhydrous by being stored over a drying agent, being stored over molecular sieves, or by distillation.

In one embodiment, the aprotic solvent is substantially anhydrous THF, which has been distilled from sodium benzophenone ketyl.

The amount of organic solvent in the reaction mixture is typically at least about 10 molar equivalents per equivalent of the Triheterocyclic Compound of Formula (II). In one embodiment, the organic solvent is present in the reaction mixture in an amount that is at least about 20 molar equivalents per equivalent of the Triheterocyclic Compound of Formula (II). In another embodiment, the organic solvent is present in the reaction mixture in an amount that is at least about 30 molar equivalents per equivalent of the Triheterocyclic Compound of Formula (II). In another embodiment, the organic solvent is present in the reaction mixture in an amount that is at least about 40 molar equivalents per equivalent of the Triheterocyclic Compound of Formula (II). In one embodiment, the organic solvent is present in the reaction mixture in an amount that ranges from about a 10 molar equivalents to about 1,000 molar equivalents per equivalent of the Triheterocyclic Compound of Formula (II). In another embodiment, the organic solvent is present in the reaction mixture in an amount that ranges from about a 20 molar equivalents to about 1,000 molar equivalents per equivalent of the Triheterocyclic Compound of Formula (II). In another embodiment, the organic solvent is present in the reaction mixture in an amount that ranges from about a 30 molar equivalents to about 1,000 molar equivalents per equivalent of the Triheterocyclic Compound of Formula (II). In another embodiment, the organic solvent is present in the reaction mixture in an amount that ranges from about a 40 molar equivalents to about 1,000 molar equivalents per equivalent of the Triheterocyclic Compound of Formula (II).

Typically, step (a) is carried out at a temperature of between about −78° C. and about 100° C. In one embodiment, step (a) is carried out at a temperature of between about −25° C. and about 75° C. In another embodiment, step (a) is carried out at a temperature of between about −10° C. and about 30° C. Typically, step (a) is carried out for an amount of time sufficient to provide a reaction mixture having an amount of the Triheterocyclic Compound of Formula (II) that has decreased by at least about 85 percent of its original amount. In one embodiment, the amount of time is sufficient to provide a reaction mixture having an amount of the Triheterocyclic Compound of Formula (II) that has decreased by at least about 90 percent of its original amount. In another embodiment, the amount of time is sufficient to provide a reaction mixture having an amount of the Triheterocyclic Compound of Formula (II) that has decreased by at least about 93 percent of its original amount. The progress of the reaction can be monitored using conventional analytical techniques, including, but are not limited to, any of those described above.

Typically, step (a) is carried out for a time period ranging from about 0.5 hours to about 48 hours. In one embodiment, step (a) is carried out for a time period ranging from about 2 hours to about 24 hours. In another embodiment, step (a) is carried out for a time period ranging from about 4 hours to 12 hours.

The method also comprises the step of protonating the Compound of Formula (vi) with an H$^+$ donor.

Suitable H$^+$ donors include, but are not limited to, water and a protic acid, such as hydrochloric acid, hydrobromic acid, hydroiodic acid, hydrofluoric acid, sulfuric acid, perchloric acid, nitric acid, methanesulfonic acid, ethanesulfonic acid, trifluoromethanesulfonic acid, benzenesulfonic acid, p-toluenesulfonic acid, p-bromobenzenesulfonic acid, p-nitrobenzenesulfonic acid, p-trifluoromethylbenzenesulfonic acid, and mixtures thereof. In one embodiment, the acid is hydrochloric acid or hydrobromic acid. In another embodiment, the acid is aqueous hydrochloric acid or aqueous hydrobromic acid.

Typically, step (b) is carried out for a time period ranging from about 10 seconds to about 1 hour. In one embodiment, step (b) is carried out for a time period ranging from about 30 seconds to about 0.5 hours. In another embodiment, step (b) is carried out for a time period ranging from about 1 minute to about 10 minutes.

The Compound of Formula (Ia) can be isolated and purified as described above.

5.4.3 Making the Compounds of Formula (Ib) from the Compounds of Formula (II) Via Acid Mediated Coupling In one particular embodiment, the invention provides methods for making Triheterocyclic Compounds of Formula (Ib)

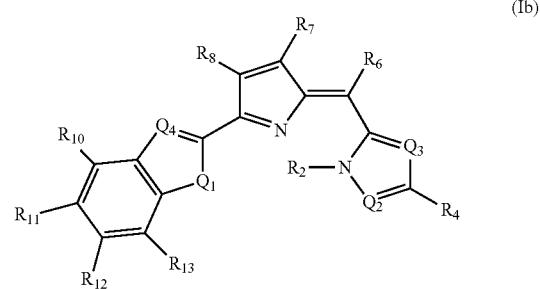

comprising contacting a compound of Formula (II)

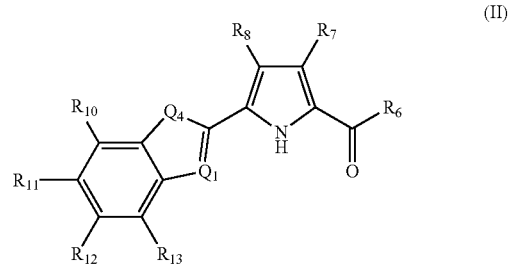

with a compound of Formula (iv)

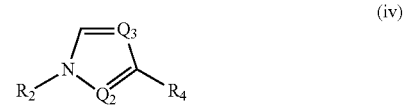

in the presence of an organic solvent and a protic acid, for a time and at a temperature sufficient to make the compound of Formula (Ib)

wherein $Q_1$-$Q_4$, $R_2$, $R_4$, $R_6$-$R_8$ and $R_{10}$-$R_{13}$ are defined above for the Triheterocyclic Compounds of Formula (Ib).

The formation of a Triheterocyclic Compound of Formula (Ib) can be monitored using conventional analytical techniques, including, but not limited to, thin-layer chromatography ("TLC"), high-performance liquid chromatography ("HPLC"), gas chromatography ("GC"), and nuclear magnetic resonance spectroscopy ("NMR") such as $^1$H or $^{13}$C NMR.

The concentration of the Triheterocyclic Compound of Formula (II) in the reaction mixture typically ranges from about 0.01 moles to about 3 moles per liter of the reaction mixture. In one embodiment, the concentration of the Triheterocyclic Compound of Formula (II) in the reaction mixture ranges from about 0.05 moles to about 1 mole per liter of the reaction mixture. In another embodiment, the concentration of the Triheterocyclic Compound of Formula (II) in the reaction mixture ranges from about 0.1 mole to about 0.5 moles per liter of the reaction mixture.

The amount of Compound of Formula (iv) in the reaction mixture is typically present in at least about a 1.5-fold molar excess to about a 10-fold molar excess relative to the amount of the Triheterocyclic Compound Formula (II). In one embodiment, the amount of Compound of Formula (iv) in the reaction mixture is at least about a 2-fold molar excess to about a 10-fold molar excess relative to the amount of the Triheterocyclic Compound of Formula (II). In another embodiment, the amount of Compound of Formula (iv) in the reaction mixture is at least about a 3-fold molar excess to about a 10-fold molar excess relative to the amount of the Triheterocyclic Compound of Formula (II).

The amount of protic acid in the reaction mixture typically ranges from about 0.0001 to about 5 molar equivalents per equivalent of the Triheterocyclic Compound of Formula (II). In another embodiment, the amount of protic acid in the reaction mixture ranges from about 0.001 to about 3 molar equivalents per equivalent of the Triheterocyclic Compound of Formula (II). In another embodiment, the amount of protic acid in the reaction mixture ranges from about 0.01 to about 1 molar equivalents per equivalent of the Triheterocyclic Compound of Formula (II).

Suitable protic acids for use in the methods of the invention include, but are not limited to, hydrochloric acid, hydrobromic acid, hydroiodic acid, hydrofluoric acid, sulfuric acid, perchloric acid, nitric acid, methanesulfonic acid, ethanesulfonic acid, trifluoromethanesulfonic acid, benzenesulfonic acid, p-toluenesulfonic acid, p-bromobenzenesulfonic acid, p-nitrobenzenesulfonic acid, p-trifluoromethylbenzenesulfonic acid, mixtures thereof and aqueous mixtures thereof. In one embodiment, the protic acid is aqueous hydrochloric acid or aqueous hydrobromic acid.

The reaction mixture further comprises an organic solvent. Suitable organic solvents include, but are not limited to alcohols, such as methanol, ethanol, isopropanol and tert-butanol; and ethers, such as diethyl ether, diisopropyl ether, THF and dioxane. In one embodiment, the solvent is methanol or ethanol.

In one embodiment, the reaction mixture is substantially anhydrous.

The amount of organic solvent in the reaction mixture is typically present at an amount of at least about 10 molar equivalents per equivalent of the Triheterocyclic Compound of Formula (II). In one embodiment, the organic solvent is present in the reaction mixture in an amount that is at least about 20 molar equivalents per equivalent of the Triheterocyclic Compound of Formula (II). In another embodiment, the organic solvent is present in the reaction mixture in an amount that is at least about 30 molar equivalents per equivalent of the Triheterocyclic Compound of Formula (II). In another embodiment, the organic solvent is present in the reaction mixture in an amount that is at least about 40 molar equivalents per equivalent of the Triheterocyclic Compound of Formula (II). In one embodiment, the organic solvent is present in the reaction mixture in an amount that ranges from about a 10 molar equivalents to about 1,000 molar equivalents per equivalent of the Triheterocyclic Compound of Formula (II). In another embodiment, the organic solvent is present in the reaction mixture in an amount that ranges from about a 20 molar equivalents to about 1,000 molar equivalents per equivalent of the Triheterocyclic Compound of Formula (II). In another embodiment, the organic solvent is present in the reaction mixture in an amount that ranges from about a 30 molar equivalents to about 1,000 molar equivalents per equivalent of the Triheterocyclic Compound of Formula (II). In another embodiment, the organic solvent is present in the reaction mixture in an amount that ranges from about a 40 molar equivalents to about 1,000 molar equivalents per equivalent of the Triheterocyclic Compound of Formula (II).

Typically, the reaction proceeds for a time ranging from about 5 minutes to about 20 hours. In one embodiment, the reaction proceeds for a time ranging from about 10 minutes hour to about 10 hours. In another embodiment, the reaction proceeds for a time ranging from about 30 minutes to about 2 hours.

Typically, the reaction temperature ranges from about 25° C. to about 100° C. In one embodiment, the reaction temperature ranges from about 25° C. to about 40° C. In another embodiment, the reaction temperature is at about room temperature.

Typically, the overall yield of the isolated and purified Triheterocyclic Compound of Formula (Ib) is greater than about 70 percent based on the amount of the Triheterocyclic Compound of Formula (II) or on the amount of the Compound of Formula (iv). In one embodiment, the overall yield of the isolated and purified Triheterocyclic Compound of Formula (Ib) is greater than about 75 percent based on the amount of the Triheterocyclic Compound of Formula (II) or on the amount of the Compound of Formula (iv). In another embodiment, the overall yield of the isolated and purified Triheterocyclic Compound of Formula (Ib) is greater than about 80 percent based on the amount of the Triheterocyclic Compound of Formula (II) or on the amount of the Triheterocyclic Compound of Formula (iv).

5.4.4 Method for Making the Compounds of Formula (Ib) from the Compounds of Formula (II) Via a Condensation Reaction In another embodiment, the invention provides methods for making a Compound of Formula (Ib) comprising the steps:

(a) contacting a compound of Formula (II)

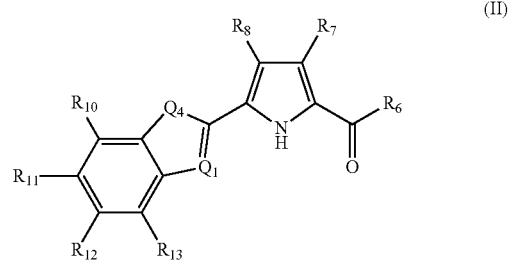

with a compound of Formula (v)

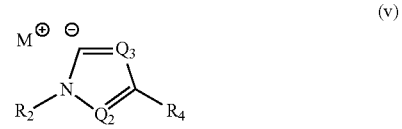

wherein M is Li, Na, K, Rb or Cs,
in the presence of a substantially anhydrous, aprotic organic solvent, for a time and at a temperature sufficient to make a compound of Formula (vi),

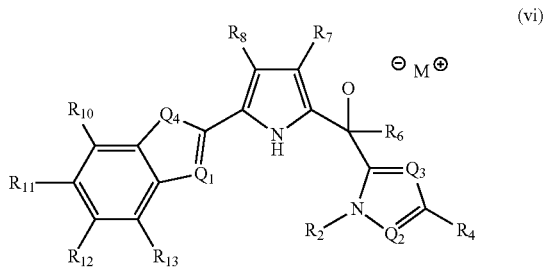

(vi)

wherein M is defined as above; and (b) protonating the compound of Formula (vi) with an $H^+$ donor for a time and at a temperature sufficient to make the compound of Formula (Ib), wherein $Q_1$-$Q_4$, $R_2$, $R_4$, $R_6$-$R_8$ and $R_{10}$-$R_{13}$ are defined above for the compounds of formula (Ib).

The formation of a Triheterocyclic Compound of Formula (Ib) can be monitored using conventional analytical techniques, including, but are not limited to, TLC, HPLC, GC, and NMR, such as $^1H$ or $^{13}C$ NMR.

The concentration of the Triheterocyclic Compound of Formula (II) in the reaction mixture typically ranges from about 0.01 moles to about 3 moles per liter of the reaction mixture. In one embodiment, the concentration of the Triheterocyclic Compound of Formula (II) in the reaction mixture ranges from about 0.05 moles to about 1 mole per liter of the reaction mixture. In another embodiment, the concentration of the Triheterocyclic Compound of Formula (II) in the reaction mixture ranges from about 0.1 mole to about 0.5 moles per liter of the reaction mixture.

The amount of Compound of Formula (v) in the reaction mixture is typically between about an equimolar amount and about a 2-fold molar excess relative to an equivalent amount of the Triheterocyclic Compound of Formula (II). In one embodiment, the amount of Compound of Formula (v) in the reaction mixture is about equimolar relative to the amount of the Triheterocyclic Compound of Formula (II).

In one embodiment, the reaction mixture is substantially anhydrous.

A Compound of Formula (v) can be prepared by deprotonating a Compound of Formula (iv) with a base, such as n-butyllithium, using methods that are well-known to those of skill in the art of organic synthesis. For examples of methods useful for preparing a Compound of Formula (v) from a Compound of Formula (iv) using a base, see Martinez et al., *J. Org. Chem.*, 46, 3760 (1981) and Minato et al., *Tetrahedron Lett.*, 22:5319 (1981).

The reaction mixture also comprises a substantially anhydrous, aprotic organic solvent. Suitable aprotic solvents include, but are not limited to THF, DMF, DMSO, N-methylpyrrolidinone and diethyl ether. Such aprotic solvents may be made substantially anhydrous by being stored over a drying agent, being stored over molecular sieves, or by distillation.

In one embodiment, the aprotic solvent is substantially anhydrous THF, which has been distilled from sodium benzophenone ketyl.

The amount of organic solvent in the reaction mixture is typically at least about 10 molar equivalents per equivalent of the Triheterocyclic Compound of Formula (II). In one embodiment, the organic solvent is present in the reaction mixture in an amount that is at least about 20 molar equivalents per equivalent of the Triheterocyclic Compound of Formula (II). In another embodiment, the organic solvent is present in the reaction mixture in an amount that is at least about 30 molar equivalents per equivalent of the Triheterocyclic Compound of Formula (II). In another embodiment, the organic solvent is present in the reaction mixture in an amount that is at least about 40 molar equivalents per equivalent of the Triheterocyclic Compound of Formula (II). In one embodiment, the organic solvent is present in the reaction mixture in an amount that ranges from about a 10 molar equivalents to about 1,000 molar equivalents per equivalent of the Triheterocyclic Compound of Formula (II). In another embodiment, the organic solvent is present in the reaction mixture in an amount that ranges from about a 20 molar equivalents to about 1,000 molar equivalents per equivalent of the Triheterocyclic Compound of Formula (II). In another embodiment, the organic solvent is present in the reaction mixture in an amount that ranges from about a 30 molar equivalents to about 1,000 molar equivalents per equivalent of the Triheterocyclic Compound of Formula (II). In another embodiment, the organic solvent is present in the reaction mixture in an amount that ranges from about a 40 molar equivalents to about 1,000 molar equivalents per equivalent of the Triheterocyclic Compound of Formula (II).

Typically, step (a) is carried out at a temperature of between about −78° C. and about 100° C. In one embodiment, step (a) is carried out at a temperature of between about −25° C. and about 75° C. In another embodiment, step (a) is carried out at a temperature of between about −10° C. and about 30° C. Typically, step (a) is carried out for an amount of time sufficient to provide a reaction mixture having an amount of the Triheterocyclic Compound of Formula (II) that has decreased by at least about 85 percent of its original amount. In one embodiment, the amount of time is sufficient to provide a reaction mixture having an amount of the Triheterocyclic Compound of Formula (II) that has decreased by at least about 90 percent of its original amount. In another embodiment, the amount of time is sufficient to provide a reaction mixture having an amount of the Triheterocyclic Compound of Formula (II) that has decreased by at least about 93 percent of its original amount. The progress of the reaction can be monitored using conventional analytical techniques, including, but are not limited to, any of those described above.

Typically, step (a) is carried out for a time period ranging from about 0.5 hours to about 48 hours. In one embodiment, step (a) is carried out for a time period ranging from about 2 hours to about 24 hours. In another embodiment, step (a) is carried out for a time period ranging from about 4 hours to 12 hours.

The method also comprises the step of protonating the Compound of Formula (vi) with an $H^+$ donor.

Suitable $H^+$ donors include, but are not limited to, water and a protic acid, such as hydrochloric acid, hydrobromic acid, hydroiodic acid, hydrofluoric acid, sulfuric acid, perchloric acid, nitric acid, methanesulfonic acid, ethanesulfonic acid, trifluoromethanesulfonic acid, benzenesulfonic acid, p-toluenesulfonic acid, p-bromobenzenesulfonic acid, p-nitrobenzenesulfonic acid, p-trifluoromethylbenzenesulfonic acid, and mixtures thereof. In one embodiment, the acid is hydrochloric acid or hydrobromic acid. In another embodiment, the acid is aqueous hydrochloric acid or aqueous hydrobromic acid.

Typically, step (b) is carried out for a time period ranging from about 10 seconds to about 1 hour. In one embodiment, step (b) is carried out for a time period ranging from about 30 seconds to about 0.5 hours. In another embodiment, step (b) is carried out for a time period ranging from about 1 minute to about 10 minutes.

The Compound of Formula (Ib) can be isolated and purified as described above.

5.4.5 Method for Making the Compounds of Formula (II) Using a Boronic Acid

In another embodiment, the invention relates to methods for making a compound of Formula (II)

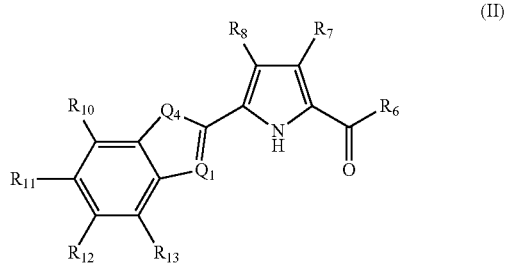

(II)

comprising contacting a compound of Formula (ii) or a compound of Formula (iia)

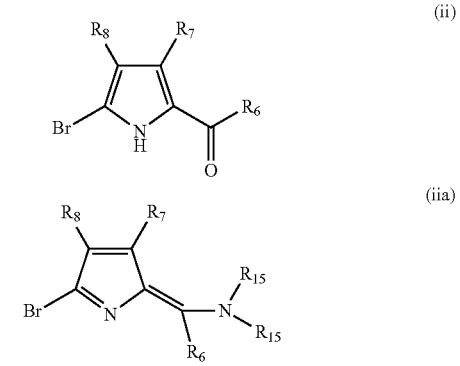

with a compound of Formula (iii)

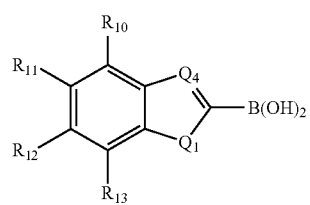

(iii)

in the presence of an organic solvent, a base, and a Ni or Pd catalyst, for a time and at a temperature sufficient to form a compound of Formula (II), wherein $Q_1$, $Q_4$, $R_6$-$R_8$ and $R_{10}$-$R_{13}$ are defined above for the compounds of formula (II) and wherein $R_{15}$ is independently $C_1$ to $C_8$ alkyl, cycloalkyl or phenyl.

The formation of a Triheterocyclic Compound of Formula (II) can be monitored using conventional analytical techniques, including, but are not limited to TLC, HPLC, GC, and NMR such as $^1$H or $^{13}$C NMR.

The concentration of the Compound of Formula (ii) or (iia) typically ranges from about 0.01 moles to about 3 moles per liter of the solvent. In one embodiment, the concentration of the Compound of Formula (ii) or (iia) ranges from about 0.05 moles to about 1 mole per liter of the solvent. In another embodiment, the concentration of the Compound of Formula (ii) or (iia) ranges from about 0.1 mole to about 0.5 moles per liter of the solvent.

The amount of Compound of Formula (iii) typically ranges from about one molar equivalent to about a 3-fold molar excess per equivalent of the Compound of Formula (II) or (iia). In one embodiment, the amount of Compound of Formula (iii) ranges from about one molar equivalent to about a 2-fold molar excess per equivalent of the Compound of Formula (ii) or (iia). In another embodiment, the amount of Compound of Formula (iii) is about a 1.5-fold molar excess per equivalent of the Compound of Formula (ii) or (iia).

Suitable bases for use in the method include, but are not limited to, alkali metal carbonates, such as $Na_2CO_3$ and $K_2CO_3$; alkali earth and alkaline earth metal hydroxides, such as LiOH, NaOH, KOH, RbOH, CsOH, FrOH, $Be(OH)_2$, $Mg(OH)_2$, $Ca(OH)_2$, $Sr(OH)_2$, $Ba(OH)_2$, and $Ra(OH)_2$; and alkali earth and alkaline earth metal alkoxides, such as LiOR, NaOR, KOR, RbOR, CsOR, FrOR, $Be(OR)_2$, $Mg(OR)_2$, $Ca(OR)_2$, $Sr(OR)_2$, $Ba(OR)_2$, and $Ra(OR)_2$, wherein R is an alkyl group such as, but not limited to, methyl, ethyl, n-butyl, t-butyl, or iso-propyl. Additional bases suitable for use in the method include sodium acetate, potassium acetate, $K_3PO_4$, TlOH, and hindered amines such as triethylamine and diisopropylethylamine. In one embodiment, the base is $Ba(OH)_2$.

The amount of base typically ranges from about one molar equivalent to about a 3-fold molar excess per equivalent of the Compound of Formula (ii) or (iia). In one embodiment, the amount of base is from about one molar equivalent to about a 2-fold molar excess per equivalent of the Compound of Formula (ii) or (iia). In another embodiment, the amount of base is about a 1.5-fold molar excess per equivalent of the Compound of Formula (ii) or (iia). In an alternate embodiment, the amount of base and the amount of the Compound of Formula (iii) are equimolar.

Suitable Ni and Pd catalysts for use in the invention include, but are not limited to $Pd(dppf)_2Cl_2$, $Pd(PPh_3)_4$, $Pd(dba)_2(PPh_3)_2$, $Pd(PPh_3)_2Cl_2$, $Pd(dba)_2$, $Pd_2(dba)_3$/P(OMe)$_3$, $Pd_2(dba)_3$/P(t-butyl)$_3$, $NiCl_2[P(OMe)_3]_2$, $Ni(dppf)_2Cl_2$, $Ni(NEt_2)_2Cl_2$ and $Ni(PPh_3)_4$. In one embodiment, the catalyst is $Pd(dppf)_2Cl_2$.

The amount of Ni or Pd catalyst typically ranges from about 0.001 molar equivalents to about an equimolar amount per equivalent of the Compound of Formula (ii) or (iia). In one embodiment, the amount of catalyst typically ranges from about 0.01 molar equivalents to about 0.5 molar equivalents per equivalent of the Compound of Formula (ii) or (iia). In another embodiment, the amount of catalyst in typically ranges from about 0.05 molar equivalents to about an 0.2 molar equivalents per equivalent of the Compound of Formula (ii) or (iia).

The amount of organic solvent is typically at least about 10 molar equivalents per equivalent of the Compound of Formula (ii) or (iia). In one embodiment, the organic solvent is present in an amount that is at least about 20 molar equivalents per equivalent of the Compound of Formula (ii) or (iia). In another embodiment, the organic solvent is present in an amount that is at least about 30 molar equivalents per equivalent of the Compound of Formula (ii) or (iia). In another embodiment, the organic solvent is present in an amount that is at least about 40 molar equivalents per equivalent of the Compound of Formula (ii) or (iia).

In one embodiment, the organic solvent is present in an amount that ranges from about a 10 molar equivalents to about 1,000 molar equivalents per equivalent of the Compound of Formula (ii) or (iia). In another embodiment, the organic solvent is present in an amount that ranges from about a 20 molar equivalents to about 1,000 molar equivalents per equivalent of the Compound of Formula (ii) or (iia). In another embodiment, the organic solvent is present in an amount that ranges from about a 30 molar equivalents to about 1,000 molar equivalents per equivalent of the Compound of Formula (ii) or (iia). In another embodiment, the organic solvent is present in an amount that ranges from about a 40 molar equivalents to about 1,000 molar equivalents per equivalent of the Compound of Formula (ii) or (iia).

Typically, the time period ranges from about 1 hour to about 20 hours. In one embodiment, the time period ranges from about 1 hour to about 10 hours. In another embodiment, the time period ranges from about 2 hours to 6 hours.

Typically, the temperature ranges from about 25° C. to about 150° C. In another embodiment, the temperature ranges from about 40° C. to about 120° C. In another embodiment, the temperature ranges from about 50° C. to about 100° C.

Suitable solvents include, but are not limited to ethers, such as diethyl ether and diisoproplyl ether; THF, dioxane, DMF, DMF/water, DMSO, benzene and toluene.

In one embodiment, the solvent is a DMF/water mixture.

In a specific embodiment, the solvent is a 4:1 DMF/water mixture.

The Compound of Formula (II) can be isolated and purified as described above for the Triheterocyclic Compound of Formula (Ib).

5.5 Therapeutic/Prophylactic Administration and Compositions

Due to their activity, the Triheterocyclic Compounds are advantageously useful in veterinary and human medicine. For example, the Triheterocyclic Compounds are useful for the treatment or prevention of cancer or neoplastic disease or inhibiting the growth of a cancer cell or neoplastic cell. The Triheterocyclic Compounds are also useful for the treatment or prevention of a viral infection or inhibiting the replication or infectivity of a virus.

The invention provides methods of treatment and prophylaxis by administration to a patient of an effective amount of a Triheterocyclic Compound. The patient is an animal, including, but not limited to, a human, mammal, or non-human animal such as a cow, horse, sheep, pig, chicken, turkey, quail, cat, dog, mouse, rat, rabbit, mouse or guinea pig, and is more preferably a mammal, and most preferably a human.

The present compositions, which comprise an effective amount of a Triheterocyclic Compound, can be administered by any convenient route, for example by infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer a Triheterocyclic Compound. In certain embodiments, more than one Triheterocyclic Compound is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer or viral infection).

In specific embodiments, it may be desirable to administer one or more Triheterocyclic Compounds locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a viral infection, tissue or organ transplant, or autoimmune response.

In certain embodiments, it may be desirable to introduce one or more Triheterocyclic Compounds into the central nervous system by any suitable route, including intraventricular and intrathecal injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulating with an aerosolizing agent, or via perfusion in a fluorocarbon or synthetic pulmonary surfactant. In certain embodiments, the Triheterocyclic Compounds can be formulated as a suppository, with traditional binders and carriers such as triglycerides.

In another embodiment, the Triheterocyclic Compounds can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the Triheterocyclic Compounds can be delivered in a controlled-release system. In one embodiment, a pump may be used (see Langer, supra; Sefton, CRC Crit. Ref Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the Triheterocyclic Compounds, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) may be used.

The present compositions comprise an effective amount of a Triheterocyclic Compound and a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a Triheterocyclic Compound is administered. Such pharmaceutical carriers can be liquids, such as water and oils, including those of petroleum, animal, vegetable or synthetic origin, such as peanut oil, soybean oil, mineral oil, sesame oil and the like.

The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a patient, the Triheterocyclic Compounds and pharmaceutically acceptable carriers can be sterile. In one embodiment, water is a carrier when the Triheterocyclic Compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release Formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

The phrase "pharmaceutically acceptable salt(s)," as used herein includes but are not limited to salts of acidic or basic groups that may be present in compounds used in the present compositions. Triheterocyclic Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e. salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, mesylate, hydroxyethyl sulfonate, and pamoate (i.e., 1,1'-methylene-bis-(2-hydroxy-3-naphthoate)) salts. Triheterocyclic Compounds included in the present compositions that include an amino moiety may form pharmaceutically acceptable salts with various amino acids, in addition to the acids mentioned above. Compounds, included in the present compositions, that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

In another embodiment, the Triheterocyclic Compounds are formulated in accordance with routine procedures as a pharmaceutical composition adapted for intravenous administration to human beings. Typically, Triheterocyclic Compounds for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the Triheterocyclic Compound is to be administered by infusion, it can be dispensed, for example, with an infusion bottle containing sterile pharmaceutical grade water or saline. Where the Triheterocyclic Compound is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered Triheterocyclic Compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate may also be used. Oral compositions can include standard carriers such as mannitol, lactose, starch, magnesium stearate, sodium saccharine, cellulose, or magnesium carbonate. Such carriers can be of pharmaceutical grade.

The amount of the Triheterocyclic Compound that will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable effective dosage ranges for intravenous administration are generally about 0.1 to about 5 mg, preferably about 0.5 to about 3 mg of Triheterocyclic Compound per kilogram body weight. In specific embodiments, the i.v. dose is about 0.1 to about 0.5 mg/kg, about 0.3 to about 0.8 mg/kg, about 0.8 to about 1.2 mg/kg, about 1.2 to about 2.0 mg/kg, or about 2.0 to about 3.0 mg/kg (or the equivalent doses expressed per square meter of body surface area). Alternatively, a suitable dose range for i.v. administration may be obtained using doses of about 8 to about 500 mg, without adjustment for a patient's body weight or body surface area. Suitable dosage ranges for intranasal administration are generally about 0.01 pg/kg body weight to 1 mg/kg body weight. Suppositories generally contain 0.5% to 10% by weight of one or more Triheterocyclic Compounds alone or in combination with another therapeutic agent. Oral compositions can contain about 10% to about 95% by weight of one or more Triheterocyclic Compounds alone or in combination with another therapeutic agent. In specific embodiments of the invention, suitable dose ranges for oral administration are generally about 0.1 to about 20 mg, preferably about 0.5 to about 10 mg, and more preferably about 1 to about 5 mg of Triheterocyclic Compound per kilogram body weight or their equivalent doses expressed per square meter of body surface area. In specific embodiments the oral dose is about 1 to about 7.5 mg/kg, about 7.5 to about 10 mg/kg, about 10 to about 12.5 mg/kg, about 12.5 to about 15 mg/kg, or about 15 to about 20 mg/kg (or the equivalent doses expressed per square meter of body surface area). In another embodiment, a suitable dose range for oral administration, from about 20 to about 2000 mg, without adjustment for a patient's body weight or body surface area. Other effective doses may be extrapolated from dose-response curves derived from in vitro or animal model test systems. Such animal models and systems are well known in the art.

The invention also provides pharmaceutical packs or kits comprising one or more containers containing one or more Triheterocyclic Compounds. Optionally associated with such container(s) can be a notice in the form prescribed by a governmental agency regulating the manufacture, use or sale of pharmaceuticals or biological products, which notice reflects approval by the agency of manufacture, use or sale for human administration. In certain embodiments, e.g., when administered for the treatment or prevention of cancer, the kit may also contain one or more chemotherapeutic agents useful for treating cancer or a neoplastic disease to be administered in combination with a Triheterocyclic Compound.

The Triheterocyclic Compounds are preferably assayed in vitro, and then in vivo, for the desired therapeutic or prophylactic activity, prior to use in humans. For example, in vitro assays can be used to determine whether administration of a specific Triheterocyclic Compound or combination of Triheterocyclic Compounds is preferred.

In one embodiment, a patient tissue sample is grown in culture, and contacted or otherwise administered with a Triheterocyclic Compound, and the effect of such Triheterocyclic Compound upon the tissue sample is observed and compared to a non-contacted tissue. In other embodiments, a cell culture model is used in which the cells of the cell culture are contacted or otherwise administered with a Triheterocyclic compound, and the effect of such Triheterocyclic Compound upon the tissue sample is observed and compared to a non-contacted cell culture. Generally, a lower level of proliferation or survival of the contacted cells compared to the non-contracted cells indicates that the Triheterocyclic Compound is effective to treat a the patient. Such Triheterocyclic Compounds may also be demonstrated effective and safe using animal model systems.

Other methods will be known to the skilled artisan and are within the scope of the invention.

5.6 Inhibition of Cancer and Neoplastic Disease

The Triheterocyclic Compounds may be demonstrated to inhibit tumor cell proliferation, cell transformation and tumorigenesis in vitro and in vivo using a variety of assays known in the art, or described herein. Such assays may use cells of a cancer cell line, or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz Inc.).

mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology, etc.

The present invention provides for cell cycle and cell proliferation analysis by a variety of techniques known in the art, including but not limited to the following:

As one example, bromodeoxyuridine (BRDU) incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, Int. J. Cancer 38, 369; Campana et al., 1988, J. Immunol. Meth. 107, 79).

Cell proliferation may also be examined using ($^3$H)-thymidine incorporation (see e.g., Chen, J., 1996, Oncogene 13:1395-403; Jeoung, J., 1995, J. Biol. Chem. 270:18367-73). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g. Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189-199; Vassilev et al., 1995, J. Cell Sci. 108:1205-15).

Cell proliferation may be measured by counting samples of a cell population over time (e.g. daily cell counts). Cells may be counted using a hemacytometer and light microscopy (e.g. HyLite hemacytometer, Hausser Scientific). Cell number may be plotted against time in order to obtain a growth curve for the population of interest. In a specific embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g. cells in S-phase) will exhibit a ploidy value higher than 2N and up to 4N DNA content. Ploidy value and cell-cycle kinetics may be further measured using propidum iodide assay (see e.g. Turner, T., et al., 1998, Prostate 34:175-81). Alternatively, the DNA ploidy may be determined by quantitation of DNA Feulgen staining (which binds to DNA in a stoichiometric manner) on a computerized microdensitometrystaining system (see e.g., Bacus, S., 1989, Am. J. Pathol. 135:783-92). In an another embodiment, DNA content may be analyzed by preparation of a chromosomal spread (Zabalou, S., 1994, Hereditas. 120:127-40; Pardue, 1994, Meth. Cell Biol. 44:333-351).

The expression of cell-cycle proteins (e.g., CycA. CycB, CycE, CycD, cdc2, Cdk4/6, Rb, p21, p27, etc.) provide crucial information relating to the proliferative state of a cell or population of cells. For example, identification in an antiproliferation signaling pathway may be indicated by the induction of p21$^{cip1}$. Increased levels of p21 expression in cells results in delayed entry into G1 of the cell cycle (Harper et al., 1993, Cell 75:805-816; Li et al., 1996, Curr. Biol. 6:189-199). p21 induction may be identified by immunostaining using a specific anti-p21 antibody available commercially (e.g. Santa Cruz). Similarly, cell-cycle proteins may be examined by Western blot analysis using commercially available antibodies. In another embodiment, cell populations are synchronized prior to detection of a cell cycle protein. Cell cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by the Triheterocyclic Compounds of the Invention. In one embodiment the length of the cell cycle is determined by the doubling time of a population of cells (e.g., using cells contacted or not contacted with one or more Triheterocyclic Compounds). In another embodiment, FACS analysis is used to analyze the phase of cell cycle progression, or purify G1, S, and G2/M fractions (see e.g., Delia, D. et al., 1997, Oncogene 14:2137-47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weinert, T., and Hartwell, L., 1993, Genetics, 134:63-80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. The invention provides for assays involved in detecting post-translational modifications (e.g. phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase h.p.l.c. (see e.g., Glover, C., 1988, Biochem. J. 250:485-91; Paige, L., 1988, Biochem J.; 250:485-91).

Activity of signaling and cell cycle proteins and/or protein complexes is often mediated by a kinase activity. The present invention provides for analysis of kinase activity by assays such as the histone H1 assay (see e.g., Delia, D. et al., 1997, Oncogene 14:2137-47).

The Triheterocyclic Compounds can also be demonstrated to alter cell proliferation in cultured cells in vitro using methods which are well known in the art. Specific examples of cell culture models include, but are not limited to, for lung cancer, primary rat lung tumor cells (Swafford et al., 1997, Mol. Cell. Biol., 17:1366-1374) and large-cell undifferentiated cancer cell lines (Mabry et al., 1991, Cancer Cells, 3:53-58); colorectal cell lines for colon cancer (Park and Gazdar, 1996, J. Cell Biochem. Suppl. 24:131-141); multiple established cell lines for breast cancer (Hambly et al., 1997, Breast Cancer Res. Treat. 43:247-258; Gierthy et al., 1997, Chemosphere 34:1495-1505; Prasad and Church, 1997, Biochem. Biophys. Res. Commun. 232:14-19); a number of well-characterized cell models for prostate cancer (Webber et al., 1996, Prostate, Part 1, 29:386-394; Part 2, 30:58-64; and Part 3, 30:136-142; Boulikas, 1997, Anticancer Res. 17:1471-1505); for genitourinary cancers, continuous human bladder cancer cell lines (Ribeiro et al., 1997, Int. J. Radiat. Biol. 72:11-20); organ cultures of transitional cell carcinomas (Booth et al., 1997, Lab Invest. 76:843-857) and rat progression models (Vet et al., 1997, Biochim. Biophys Acta 1360:39-44); and established cell lines for leukemias and lymphomas (Drexler, 1994, Leuk. Res. 18:919-927, Tohyama, 1997, Int. J. Hematol. 65:309-317).

The Triheterocyclic Compounds can also be demonstrated to inhibit cell transformation (or progression to malignant phenotype) in vitro. In this embodiment, cells with a transformed cell phenotype are contacted with one or more Triheterocyclic Compounds, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology*, 3d Ed., John Wiley & Sons, New York, pp. 436-446).

In one embodiment, the Triheterocyclic Compounds are cytotoxic.

In another embodiment, the Triheterocyclic Compounds demonstrate a higher level of cytotoxicity in cancer cells than in non-cancer cells.

Loss of invasiveness or decreased adhesion may also be used to demonstrate the anti-cancer effects of the Triheterocyclic Compounds. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278:1464-66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464-66).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, Biochem. Biophys. Res. Commun. 193: 518-25).

The Triheterocyclic Compounds can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in *Harrison's Principals of Internal Medicine*, 13th Edition, Isselbacher et al., eds., McGraw-Hill, New York, p. 1814, and Lovejoy et al., 1997, J. Pathol. 181:130-135). Specific examples include for lung cancer, transplantation of tumor nodules into rats (Wang et al., 1997, Ann. Thorac. Surg. 64:216-219) or establishment of lung cancer metastases in SCID mice depleted of NK cells (Yono and Sone, 1997, Gan To Kagaku Ryoho 24:489-494); for colon cancer, colon cancer transplantation of human colon cancer cells into nude mice (Gutman and Fidler, 1995, World J. Surg. 19:226-234), the cotton top tamarin model of human ulcerative colitis (Warren, 1996, Aliment. Pharmacol. Ther. 10 Supp 12:45-47) and mouse models with mutations of the adenomatous polyposis tumor suppressor (Polakis, 1997, Biochim. Biophys. Acta 1332:F127-F147); for breast cancer, transgenic models of breast cancer (Dankort and Muller, 1996, Cancer Treat. Res. 83:71-88; Amundadittir et al., 1996, Breast Cancer Res. Treat. 39:119-135) and chemical induction of tumors in rats (Russo and Russo, 1996, Breast Cancer Res. Treat. 39:7-20); for prostate cancer, chemically-induced and transgenic rodent models, and human xenograft models (Royai et al., 1996, Semin. Oncol. 23:35-40); for genitourinary cancers, induced bladder neoplasm in rats and mice (Oyasu, 1995, Food Chem. Toxicol 33:747-755) and xenografts of human transitional cell carcinomas into nude rats (Jarrett et al., 1995, J. Endourol. 9:1-7); and for hematopoietic cancers, transplanted allogeneic marrow in animals (Appelbaum, 1997, Leukemia 11 (Suppl. 4):S15-S17). Further, general animal models applicable to many types of cancer have been described, including, but not restricted to, the p53-deficient mouse model (Donehower, 1996, Semin. Cancer Biol. 7:269-278), the Min mouse (Shoemaker et al., 1997, Biochem. Biophys. Acta, 1332:F25-F48), and immune responses to tumors in rat (Frey, 1997, Methods, 12:173-188).

For example, a Triheterocyclic Compound can be administered to a test animal, preferably a test animal predisposed to develop a type of tumor, and the test animal subsequently examined for a decreased incidence of tumor formation in comparison with controls to which are not administered the Triheterocyclic Compound. Alternatively, a Triheterocyclic Compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to controls to which are not administered the Triheterocyclic compound.

5.7 Treatment or Prevention of Cancer or a Neoplastic Disease Further Comprising Administering Chemotherapy or Radiotherapy Cancer or a neoplastic disease, including, but not limited to, neoplasms, tumors, metastases, or any disease or disorder characterized by uncontrolled cell growth, can be treated or prevented by administration of an effective amount of a Triheterocyclic Compound.

In certain embodiments, the present methods for treating or preventing cancer or neoplastic disease further comprise administering an anti-cancer, chemotherapeutic agent including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In another embodiment, the anti-cancer agents is one or more of those presented below in Table 1.

TABLE 1

| Radiation: | γ-radiation |
|---|---|
| Alkylating agents | |
| Nitrogen mustards: | cyclophosphamide |
|  | Ifosfamide |
|  | Trofosfamide |
|  | Chlorambucil |
| Nitrosoureas: | carmustine (BCNU) |
|  | Lomustine (CCNU) |
| Alkylsulphonates | Busulfan |
|  | Treosulfan |
| Triazenes: | Dacarbazine |
| Platinum containing compounds: | Cisplatin |
|  | carboplatin |
| Plant Alkaloids | |
| Vinca alkaloids: | Vincristine |
|  | Vinblastine |
|  | Vindesine |
|  | Vinorelbine |
| Taxoids: | Paclitaxel |
|  | Docetaxol |
| DNA Topoisomerase Inhibitors | |
| Epipodophyllins: | Etoposide |
|  | Teniposide |
|  | Topotecan |
|  | 9-aminocamptothecin |
|  | campto irinotecan |
|  | crisnatol |
| mitomycins: | |
| mitomycin C | Mitomycin C |
| Anti-metabolites | |
| Anti-folates: | |
| DHFR inhibitors: | methotrexate |
|  | Trimetrexate |
| IMP dehydrogenase Inhibitors: | mycophenolic acid |
|  | Tiazofurin |
|  | Ribavirin |
|  | EICAR |
| Ribonucleotide reductase Inhibitors: | Hydroxyurea |
|  | Deferoxamine |
| Pyrimidine analogs: | |
| Uracil analogs 5-Fluorouracil | Floxuridine |
|  | Doxifluridine |
|  | Ratitrexed |
| Cytosine analogs | cytarabine (ara C) |
|  | Cytosine arabinoside |
|  | Fludarabine |
| Purine analogs: | mercaptopurine |
|  | Thioguanine |
| Hormonal therapies: | |
| Receptor antagonists: | Raloxifene |
| Anti-estrogens Tamoxifen | Megestrol |
| LHRH agonists: | Goserelin |
|  | Leuprolide acetate |
| Anti-androgens: | Flutamide |
|  | Bicalutamide |

TABLE 1-continued

| Retinoids/Deltoids | |
|---|---|
| Vitamin D3 analogs: | EB 1089 |
| | CB 1093 |
| | KH 1060 |
| Photodyamic therapies: | Vertoporfin (BPD-MA) |
| | Phthalocyanine |
| | photosensitizer Pc4 |
| | Demethoxy-hypocrellin A |
| | (2BA-2-DMHA) |
| Cytokines: | Interferon-α |
| | Interferon-γ |
| | Tumor necrosis factor |
| Others: | |
| Isoprenylation inhibitors: | Lovastatin |
| Dopaminergic neurotoxins: | 1-methyl-4-phenylpyridinium ion |
| Kinase inhibitors: | Staurosporine |
| | Imatinib mesylate |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors | verapamil |
| $Ca^{2+}$ ATPase inhibitors: | Thapsigargin |

In other embodiments, the methods for treating or preventing cancer or neoplastic disease further comprise administering radiation therapy and/or one or more chemotherapeutic agents, in one embodiment where the cancer has not been found to be refractory. The Triheterocyclic Compound can be administered to a patient that has also undergone surgery as treatment for the cancer.

In another specific embodiment, the invention provides a method to treat or prevent cancer that has shown to be refractory to treatment with a chemotherapy and/or radiation therapy.

In a specific embodiment, an effective amount of a Triheterocyclic Compound is administered concurrently with chemotherapy or radiation therapy. In another specific embodiment, chemotherapy or radiation therapy is administered prior or subsequent to administration of a Triheterocyclic Compound, such as at least an hour, five hours, 12 hours, a day or a week subsequent to or prior to administration of the Triheterocyclic Compound.

If the Triheterocyclic Compound is administered prior to administering chemotherapy or radiation therapy, the chemotherapy or radiation therapy is administered while the Triheterocyclic Compound is exerting its therapeutic or prophylactic effect. If the chemotherapy or radiation therapy is administered prior to administering a Triheterocyclic Compound, the Triheterocyclic Compound is administered while the chemotherapy or radiation therapy is exerting its therapeutic effect.

The chemotherapeutic agents can be administered in a series of sessions, any one or a combination of the chemotherapeutic agents listed above can be administered. With respect to radiation therapy, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, may also be administered to expose tissues to radiation.

Additionally, the invention provides methods of treatment of cancer or neoplastic disease with a Triheterocyclic Compound as an alternative to chemotherapy or radiation therapy where the chemotherapy or the radiation therapy has proven or may prove too toxic, e.g., results in unacceptable or unbearable side effects, for the patient being treated. The patient being treated with the present compositions may, optionally, be treated with other cancer treatments such as surgery, radiation therapy or chemotherapy, depending on which treatment is found to be acceptable or bearable.

5.8 Cancer and Neoplastic Disease Treatable or Preventable

Cancers or neoplastic diseases and related disorders that can be treated or prevented by administration of a Triheterocyclic Compound include but are not limited to those listed in Table 2 (for a review of such disorders, see Fishman et al., 1985, Medicine, 2d Ed., J.B. Lippincott Co., Philadelphia):

TABLE 2

| CANCERS AND NEOPLASTIC DISORDERS |
|---|
| Leukemia |
|     acute leukemia |
|     acute t-cell leukemia |
|     acute lymphocytic leukemia |
|     acute myelocytic leukemia |
|         myeloblastic |
|         promyelocytic |
|         myelomonocytic |
|         Monocytic |
|     erythroleukemia |
|     chronic leukemia |
|     chronic myelocytic (granulocytic) leukemia |
|     chronic lymphocytic leukemia |
| Polycythemia vera |
| Lymphoma |
|     Hodgkin's disease |
|     non-Hodgkin's disease |
| Multiple myeloma |
| Waldenström's macroglobulinemia |
| Heavy chain disease |
| Solid tumors |
|     sarcomas and carcinomas |
|         fibrosarcoma |
|         myxosarcoma |
|         liposarcoma |
|         chondrosarcoma |
|         osteogenic sarcoma |
|         chordoma |
|         angiosarcoma |
|         endotheliosarcoma |
|         lymphangiosarcoma |
|         lymphangioendotheliosarcoma |
|         synovioma |
|         mesothelioma |
|         Ewing's tumor |
|         leiomyosarcoma |
|         rhabdomyosarcoma |
|         colon carcinoma |
|         pancreatic cancer |
|         breast cancer |
|         ovarian cancer |
|         prostate cancer |
|         squamous cell carcinoma |
|         basal cell carcinoma |
|         adenocarcinoma |
|         sweat gland carcinoma |
|         sebaceous gland carcinoma |
|         papillary carcinoma |

TABLE 2-continued

CANCERS AND NEOPLASTIC DISORDERS

> papillary adenocarcinomas
> cystadenocarcinoma
> medullary carcinoma
> bronchogenic carcinoma
> renal cell carcinoma
> hepatoma
> bile duct carcinoma
> choriocarcinoma
> seminoma
> embryonal carcinoma
> Wilms' tumor
> cervical cancer
> uterine cancer
> testicular tumor
> lung carcinoma
> small cell lung carcinoma
> bladder carcinoma
> epithelial carcinoma
> glioma
> astrocytoma
> medulloblastoma
> craniopharyngioma
> ependymoma
> pinealoma
> hemangioblastoma
> acoustic neuroma
> oligodendroglioma
> meningioma
> melanoma
> neuroblastoma
> retinoblastoma In specific embodiments, cancer, malignancy or dysproliferative changes (such as metaplasias and dysplasias), or hyperproliferative disorders, are treated or prevented in the ovary, breast, colon, lung, skin, pancreas, prostate, bladder, or uterus. In other specific embodiments, sarcoma, melanoma, or leukemia is treated or prevented.

In another embodiment, the Triheterocyclic Compounds are used to treat or prevent cancers including prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), or Testicular (preferably germ cell).

In another embodiment, the Triheterocyclic Compounds are used to inhibit the growth of a cell derived from a cancer or neoplasm such as prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), or Testicular (preferably germ cell).

In specific embodiments of the invention, the Triheterocyclic Compounds are used to inhibit the growth of a cell, said cell being derived from a cancer or neoplasm in Table 2 or herein.

5.10 Demonstration of Inhibition of Viruses and Viral Infections

The Triheterocyclic Compounds may be demonstrated to inhibit the replication or infectivity of a virus or a virus-infected cell in vitro or in vivo using a variety of assays known in the art, or described herein. In certain embodiments, such assays may use cells of a cell line, or cells from a patient. In specific embodiments, the cells may be infected with a virus prior to the assay, or during the assay. The cells may be contacted with a virus. In certain other embodiments, the assays may employ cell-free viral cultures.

In one embodiment, a Triheterocyclic Compound is demonstrated to have activity in treating or preventing viral disease by contacting cultured cells that exhibit an indicator of a viral reaction (e.g., formation of inclusion bodies) in vitro with the Triheterocyclic Compound, and comparing the level of the indicator in the cells contacted with the Triheterocyclic Compound with the level of the indicator in cells not so contacted, wherein a lower level in the contacted cells indicates that the Triheterocyclic Compound has activity in treating or preventing viral disease. Cell models that can be used for such assays include, but are not limited to, viral infection of T lymphocytes (Selin et al., 1996, J. Exp. Med. 183:2489-2499); hepatitis B infection of dedifferentiated hepatoma cells (Raney et al., 1997, J. Virol. 71:1058-1071); viral infection of cultured salivary gland epithelial cells (Clark et al., 1994, Autoimmunity 18:7-14); synchronous HIV-1 infection of $CD4^+$ lymphocytic cell lines (Wainberg et al., 1997, Virology 233:364-373); viral infection of respiratory epithelial cells (Stark et al., 1996, Human Gene Ther. 7:1669-1681); and amphotrophic retroviral infection of NIH-3T3 cells (Morgan et al., 1995, J. Virol. 69:6994-7000).

In another embodiment, a Triheterocyclic Compound can be demonstrated to have activity in treating or preventing viral disease by administering a Triheterocyclic Compound to a test animal having symptoms of a viral infection, such as characteristic respiratory symptoms in animal models, or which test animal does not exhibit a viral reaction and is subsequently challenged with an agent that elicits an viral reaction, and measuring the change in the viral reaction after the administration of the Triheterocyclic Compound, wherein a reduction in the viral reaction or a prevention of the viral reaction indicates that the Triheterocyclic Compound has activity in treating or preventing viral disease. Animal models that can be used for such assays include, but are not limited to, guinea pigs for respiratory viral infections (Kudlacz and Knippenberg, 1995, Inflamm. Res. 44:105-110); mice for influenza virus infection (Dobbs et al., 1996, J. Immunol. 157:1870-1877); lambs for respiratory syncitial virus infection (Masot et al., 1996, Zentralbl. Veterinarmed. 43:233-243); mice for neurotrophic virus infection (Barna et al., 1996, Virology 223:331-343); hamsters for measles infection (Fukuda et al., 1994, Acta Otolaryngol. Suppl (Stockh.) 514: 111-116); mice for encephalomyocarditis infection (Hirasawa et al., 1997, J. Virol. 71:4024-4031); and mice for cytomegalovirus infection (Orange and Biron, 1996, J. Immunol. 156:1138-1142). In certain embodiments of the invention more than one Triheterocyclic Compound is administered to a test animal, virus, or viral-infected cell.

5.11 Viruses and Viral Infections

Viruses and viral infections that can be treated or prevented by administering a Triheterocyclic Compound include but are not limited to those listed in Table 3 including, but not limited to, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

In a one embodiment of the invention, the Triheterocyclic Compounds are used to treat or prevent a viral infection associated with a virus as listed in Table 3. In another embodiment, the Triheterocyclic Compounds are used to inhibit the replication or infectivity of a virus listed in Table 3. In yet another embodiment, the Triheterocyclic Compounds are used to inhibit the growth of a cell infected with a virus listed in Table 3.

TABLE 3

| | |
|---|---|
| Herpesviruses: | EBV |
| | HHV-8 (KSHV) |
| | Herpesvirus saimiri |
| Adenoviruses: | All strains |
| Retroviruses: | HIV-1 and 2 |
| | HTLV-I |
| Human Papillomaviruses: | HPV - all strains |
| Birnaviruses: | Infectious pancreatic necrosis virus |
| Other: | African Swine Fever virus (all strains) |

5.12 Prodrugs

The present invention also encompasses the following prodrugs of the Triheterocyclic Compounds of the invention:

Compound 66

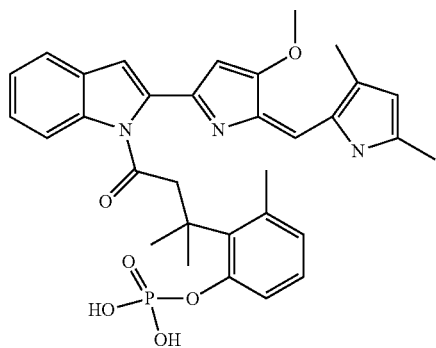

Phosphoric acid mono-[2-(3-{2-[5-(3,5-dimethyl-1H-pyrrol-2-ylmethylene)-4-methoxy-5H-pyrrol-2-yl]-indol-1-yl}-1, 1-dimethyl-3-oxo-propyl)-3-methyl-phenyl] ester Compound 67

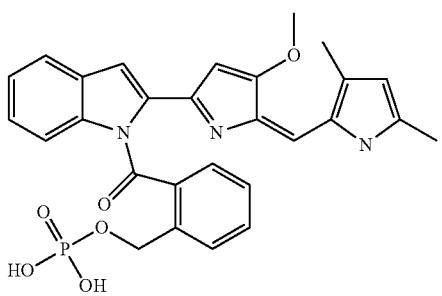

Phosphoric acid mono-(2-{2-[5-(3,5-dimethyl-1H-pyrrol-2-ylmethylene)-4-methoxy-5H-pyrrol-2-yl]-indole-1-carbonyl}-benzyl) ester In certain embodiments, the invention provides methods for treating cancer in a patient, comprising administering to the patient an effective amount of Compound 66 or Compound 67. In certain embodiments, the invention provides methods for treating a viral infection in a patient, comprising administering to the patient an effective amount of Compound 66 or Compound 67. Illustrative methods for synthesizing Compound 66 or Compound 67, respectively, are described in Example 4.

The present invention also provides prodrugs of the Triheterocyclic Compounds of the invention. Prodrugs include derivatives of Triheterocyclic Compounds that can hydrolyze, oxidize, or otherwise react under biological conditions (in vitro or in vivo) to provide an active Triheterocyclic Compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, and biohydrolyzable phosphate analogues. In certain embodiments, prodrugs of Triheterocyclic Compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh). Biohydrolyzable moieties of a Triheterocyclic Compounds 1) do not interfere with the biological activity of the compound but can confer upon that compound advantageous properties in vivo, such as uptake, duration of action, or onset of action; or 2) are biologically inactive but are converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

6. EXAMPLES 6.1 Example 1

Compound 1 hydrochloride was prepared as shown in Scheme 2a below.

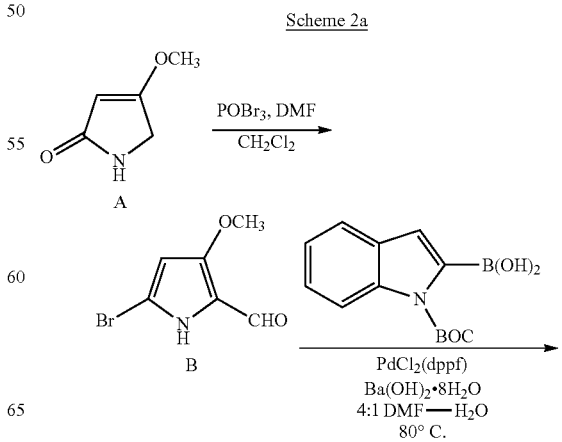

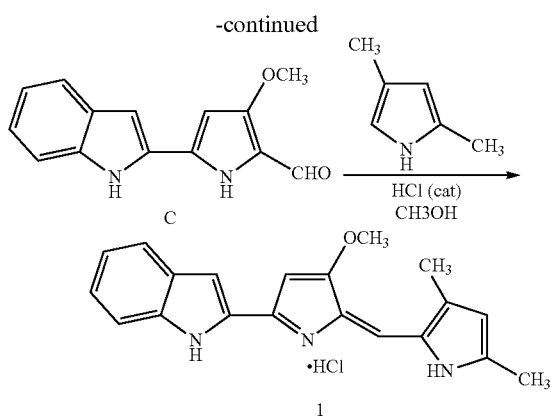

Preparation of 5-bromo-3-methoxypyrrole-2-carboxaldehyde B

To a solution of phosphoryl bromide (220 mol %, 5.58 g) in dry dichloromethane (20 mL) was added DMF (220 mol %, 1.4 mL) dropwise over 2 minutes. The resulting reaction mixture was stirred at room temperature for 30 min and concentrated in vacuo to provide the Vilsmeyer complex as a white solid. After drying in vacuo for 1 h, the white solid was suspended in dry dichloromethane (20 mL) and cooled to 0° C. A solution of 4-methoxy-3-pyrrolin-2-one (A) (1 g, 8.84 mmol) in dichloromethane (10 mL) was added dropwise and the resulting reaction mixture was stirred at 0° C. for 30 min, then at room temperature for 20 h. The mixture was poured onto ice (75 mL), treated with aqueous NaOH 4N (50 mL), diluted with EtOAc (100 mL), and stirred for 15 min. The layers were separated, and the aqueous layer was extracted with EtOAc (3×60 mL). The combined organic layers were washed with brine (3×200 mL), dried over $Na_2SO_4$, filtered and concentrated in vacuo to afford a crude residue that was purified using flash column chromatography over silica gel with a gradient elution of 0-20% EtOAC/Hexanes to provide Compound B as a white solid. NMR $^1$H (300 MHz, $CDCl_3$): δ (ppm) 3.95 (s, 3H); 5.90 (s, 1H); 9.30 (s, 1H), 9.92-10.34 (bs, 1H). m/z: 205.1 [M+1]

Preparation of 5-indolyl-3-methoxypyrrole-2-carboxaldehyde C

To a mixture of Compound B (120 mg, 0.60 mmol), N-Boc-indoleboronic acid (150 mol %, 230 mg), barium hydroxide octahydrate (150 mol %, 278 mg) and dichloro(diphenylphosphinoferrocene)palladium(II) (10 mol %, 48 mg), was added a degassed mixture of 4:1 DMF/water (15 mL, 0.04M). The mixture was stirred for 3 h at 80° C., then diluted with EtOAc (20 mL) and water. The resulting solution was filtered through a pad of Celite and the layers were separated. The organic layer was washed with brine (3×50 mL), dried over $Na_2SO_4$, filtered and concentrated in vacuo to provide a crude residue that was purified using flash column chromatography over silica gel with a gradient elution of 0-75% EtOAC/Hexanes to provide Compound C as a green solid. $^1$H NMR (300 MHz, $CD_3OD$): δ (ppm) 3.95 (s, 3H); 6.40 (s, 1H); 6.95 (s, 1H); 7.00 (t, 1H); 7.15 (t, 1H); 7.35 (d, 1H); 7.54 (d, 1H); 9.33 (s, 1H). m/z: 241.17 [M+1]

Preparation of Compound 1 Hydrochloride

To a solution of Compound C (2 mg, 8 μmol) and 2,4-dimethylpyrrole (100 mol %, 0.8 mg) in methanol (0.4 mL) was added 1 drop of saturated methanolic HCl. The resulting dark red solution was stirred for 1 h at room temperature. The reaction mixture was concentrated in vacuo and the resulting residue was dried in vacuo to provide Compound 1 hydrochloride. NMR $^1$H (300 MHz, $CDCl_3$): δ (ppm) 2.33 (s, 3H); 2.63 (s, 3H); 4.04 (s, 3H); 6.10 (s, 1H); 6.30 (s, 1H); 7.07-7.16 (m, 3H); 7.30 (t, 1H); 7.60 (d, 2H); 12.22-12.38 (bs, 1H); 12.90-13.10 (bs, 1H). m/z: 319.17 [M+1].

Preparation of Compound 1 Tartrate

About one gram of Compound 1 hydrochloride was dissolved in 100 mL of ethylacetate and washed with 5% NaOH solution (2×20 mL) (until the water layer has a pH between 9 and 10). The resulting organic layer was then separated, dried and evaporated to obtain Compound 1 (free base).

About five grams of Compound 1 were transferred to a freeze-dry flask, and 100 ml of acetonitrile was added. The resulting orange suspension was agitated for one minute. Then 50 ml of distilled water and 2.36 g of L-tartaric acid was added. The resulting red-to-purple mixture was agitated for 5 minutes. Another 50 ml of distilled water was added, and the thick brown suspension was agitated for 5 minutes. The freeze-dry flask containing the suspension was immediately cooled to a temperature of between −53 to −78° C. to freeze the suspension. The flask was then installed on a freeze dryer and vacuum was applied. The flask was maintained under a pressure of less than 50 mTorr (0.07 mbar) until the material was dry, providing Compound 1 Tartrate as a red-to-brown amorphous powder.

Compound 1 hydrochloride was also prepared as shown in Scheme 2b below.

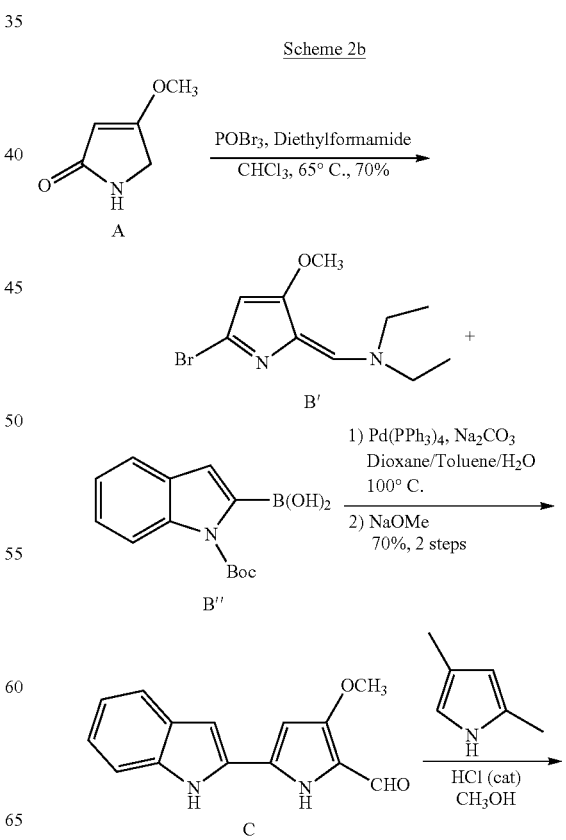

Scheme 2b

-continued

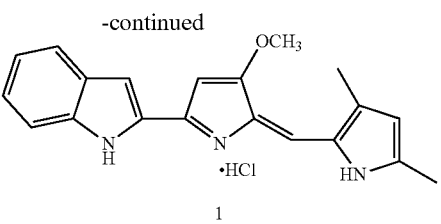

Synthesis of 5-bromo-3-methoxypyrromethene (B')

To a mixture of diethylformamide (3 eq, 5.8 mL) and chloroform (5 mL) at 0° C. was added dropwise a solution of phosphorus oxybromide (2.5 eq, 12.6 g) in chloroform (15 mL). The resulting suspension was stirred at 0° C. for 30 min, and the solvent was removed by rotary evaporation to obtain the Vilsmeier complex as a white solid. After drying in vacuo for 20 min, the solid was treated with chloroform (10 mL) and cooled to 0° C. A solution of 4-methoxy-3-pyrrolin-2-one (A, 2 g, 17.7 mmol) in chloroform (20 mL) was added dropwise and the mixture was warmed to room temperature, then heated at 60° C. for 5 h. The mixture was poured onto ice (75 mL), and the pH of the aqueous solution was adjusted to pH 7-8 by treatment with NaOH 2N. EtOAc (40 mL) was added to the resulting precipitate and the mixture was filtered over Celite® to remove the black solid containing phosphorus salts.

The two layers were separated and the aqueous layer was extracted with EtOAc (3×100 mL). The organic layers were combined, washed with brine (3×200 mL), dried over $Na_2SO_4$, filtered and the solvent was removed by rotary evaporation to furnish the crude enamine intermediate B'.

The residue was filtered over a pad of silica gel (50 mL) using a 10% EtOAC/Hexanes as eluent to obtain the enamine as an oil, which upon drying in vacuo lead to a beige solid.

Yield: 3.20 g, 70%.
M/Z: 260.1 [M+1]
RMN $^1$H (300 MHz, $CDCl_3$): δ (ppm) 1.24-1.37 (m, 6H); 3.31-3.46 (q, 2H); 3.76 (s, 3H), 4.03-4.18 (q, 2H); 5.58 (s, 3H); 6.98 (s, 3H).

Synthesis
5-indolyl-3-methoxypyrrole-2-carboxaldehyde (C)

To a degassed solution of toluene (1.5 mL) were added $Pd(OAc)_2$ (0.1 eq, 86 mg) and $PPh_3$ (0.45 eq, 456 mg). The mixture immediately became bright yellow and was stirred at 70° C. for 20 min under $N_2$.

A solution of 5-bromo-3-methoxypyrromethene (B', 1.17 g, 4.51 mmol) and N-Boc-indoleboronic acid (B", 1.1 eq, 1.29 g) in 10% water/dioxane (15 mL) was degassed and purged with $N_2$. The solution was transferred to the suspension of $Pd(PPh_3)_4$ in toluene followed by the addition of $Na_2CO_3$ (3.0 eq, 1.23 g). The mixture was stirred for 3 h at 100° C., then treated with NaOMe (1.0 eq, 244 mg). The mixture was stirred for 15 min at 100° C., then treated with another portion of NaOMe (1.0 eq, 244 mg) and stirred at 100° C. for 10 min.

The mixture was poured onto water (100 mL), the pH of the solution was lowered to pH 7 with 2N HCl and the mixture was stirred for 10 min. The brown precipitate was recovered by filtration over a fritted disc funnel and washed with water (2×50 mL). The precipitate was dissolved in acetone and the solvent was removed by rotary evaporation. The resulting solid was treated with 5 mL of $CHCl_3$ and $Et_2O$ (10 mL) and the solution was let stand for 5 min until a yellow solid was obtained, which was filtered over a fritted disc funnel. The yellow solid was washed with 10 mL of $CHCl_3$ then 2×10 mL $Et_2O$.

The desired 5-indolyl-3-methoxypyrrole-2-carboxaldehyde (C) is thus obtained as a yellow solid and used without further purification.

Yield: 807 mg, 75%.
M/Z: 241.17 [M+H$^+$1]
RMN $^1$H (300 MHz, $CD_3OD$): δ (ppm) 3.95 (s, 3H); 6.40 (s, 1H); 6.95 (s, 1H); 7.00 (t, 1H); 7.15 (t, 1H); 7.35 (d, 1H); 7.54 (d, 1H); 9.33 (s, 1H).

Condensation of
5-indolyl-3-methoxypyrrole-2-carboxaldehyde (C)
with 2,4-dimethylpyrrole To a suspension of 5-indolyl-3-methoxypyrrole-2-carboxaldehyde (C, 200 mg, 0.83 mmol) and 2,4-dimethylpyrrole (1.1 eq, 94 µL) in methanol (8.3 mL) was added a solution of methanolic HCl (200 µL). The solution immediately turned dark pink and was stirred for 2 h at room temperature. The solvent was removed by rotary evaporation and the solid was dissolved in EtOAc (30 mL). The organic phase was washed with aqueous $NaHCO_3$ (sat., 2×60 mL), brine (2×60 mL), dried over anhydrous $Na_2CO_3$, filtered and evaporated.

The product was purified by column chromatography over silica gel using a gradient of 0-30% EtOAc/Hexanes as eluent.

Yield: 237 mg, 90%.
M/Z: 319.17 [M+1]
RMN $^1$H (300 MHz, Acetone-$d_6$): δ (ppm) 2.13 (s, 3H); 2.21 (s, 3H); 4.00 (s, 3H); 5.81 (s, 1H); 6.44 (s, 1H); 6.88-7.22 (m, 5H); 8.02 (d, 1H).

6.2 Example 2

Effects of Compound 1 Tartrate on Cancer Cell Viability In Vitro

To demonstrate the effect of Compound 1 Tartrate on cell viability, cellular ATP levels were measured before and after treating selected cell lines with Compound 1 Tartrate. Selected cell lines included C33A cervical carcinoma cells, Mrc-5 normal lung fibroblasts, PC-3 human prostatic carcinoma cell line, OVCAR-3 human ovarian carcinoma cell line, H460 non-small cell lung cancer cell line, A549 human lung carcinoma cell line, H1299 human non-small cell lung cancer cells, MCF-7 human breast cancer cell line, SW-480 human adenocarcinoma cell line, B16-F1 mouse melanoma cell line (American Type Culture Collection, Manassas, Va. USA), HMEC normal mammary epithelial cells (Clonetics San Diego, Calif., USA) and ADR-RES human breast cancer cell line (NCI, MD, USA), which were cultured in the media recommended by the American Type Culture Collection. The cells lines were plated in 96-well microtiter plates (PerkinElmer Life Sciences Inc, Boston, Mass., USA) at a confluency that allowed them to reach confluence after 4 days of growth. One day after plating, the cells were treated with various concentrations of Compound 1 Tartrate. Stock solutions of the Compound 1 Tartrate were prepared in dimethyl sulfoxide (Sigma-Aldrich Inc., St. Louis, Mo., USA), diluted in the recommended media and then added to the cells. The total dimethyl sulfoxide on the cells was 1%. After 3 days of incubation the ATP levels in the cells were quantified using a luminescent ViaLight detection system (Bio-Whittaker, Md., USA). The results were plotted relative to untreated control cells, which were set at a value of 100.

Figure 1:
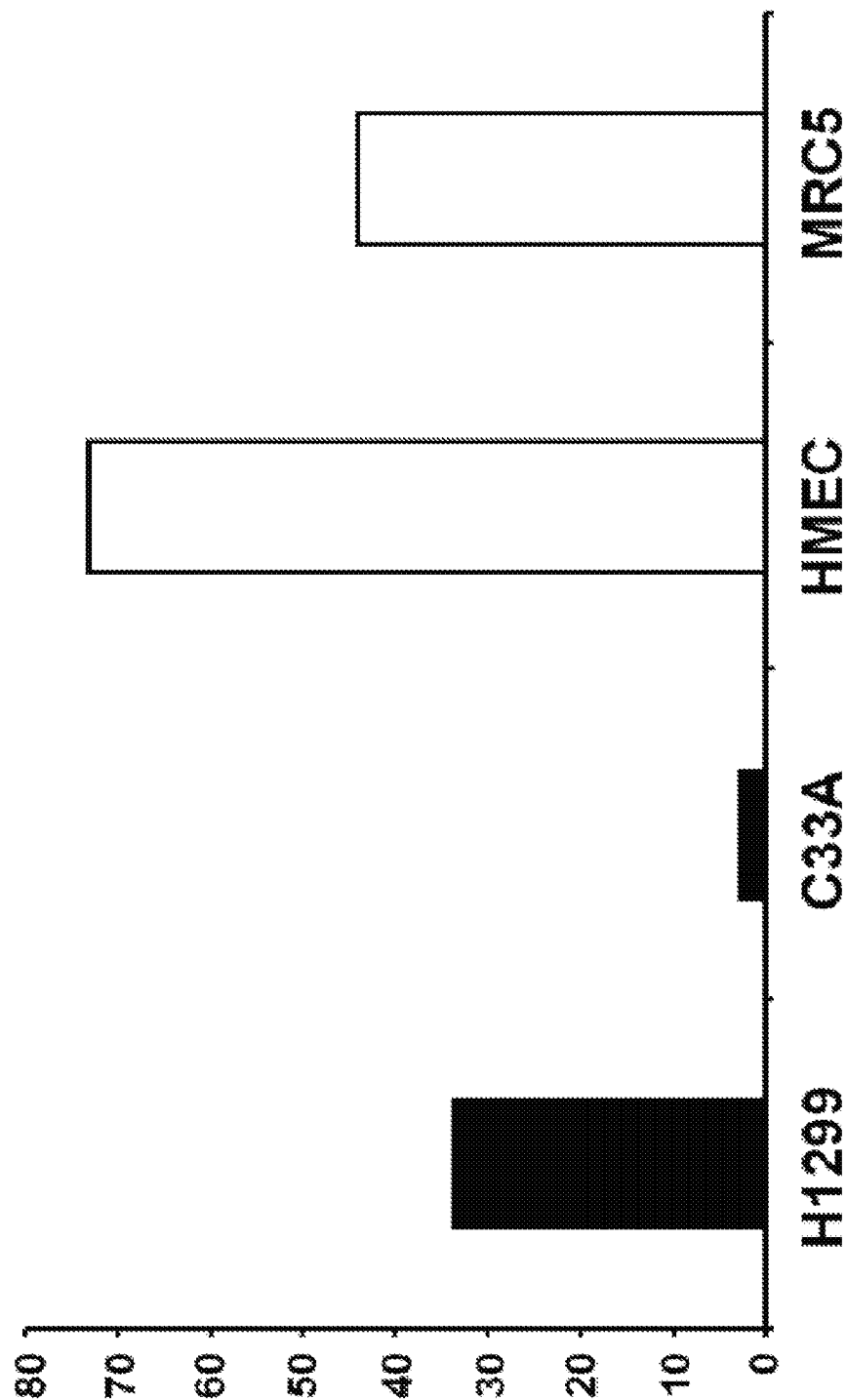

As illustrated in the bar graph of FIG. 1, Compound 1 Tartrate has a significantly greater effect on ATP levels in cancer cells than in normal cells. Measurements of ATP levels 72 hours after treatment with 0.5 µM Compound 1 Tartrate indicate that Compound 1 Tartrate was significantly more effective at lowering ATP levels in the cancer cell lines H1299 and C33A compared with the ATP levels in normal cell lines HMEC and MRC-5. These results demonstrate that Compound 1 Tartrate is selectively cytotoxic to cancer cells and is useful for treating or preventing cancer, particularly lung or cervical cancer.

To further demonstrate the efficacy of Compound 1 Tartrate as an anti-cancer agent, the effect of various concentrations of Compound 1 Tartrate on cellular ATP levels in ten different cancer cell lines was evaluated. As depicted in Table 1, Compound 1 Tartrate showed greater efficacy in decreasing cellular ATP levels in the cancer cell lines than in the HMEC normal mammary epithelial cell line. These results demonstrate that Compound 1 Tartrate is a selective anti-cancer agent.

TABLE 1

Anti-oncogenic effects of Compound 1 tartrate

| Cell line | Tissue | $IC_{50}$ of Compound 1 tartrate (µM) |
| --- | --- | --- |
| C-33A | Cervix | 0.2 |
| PC-3 | Prostate | 0.2 |
| OVCAR-3 | Ovary | 0.2 |
| H460 | NSCLC | 0.3 |
| A549 | NSCLC | 0.4 |
| H1299 | NSCLC | 0.5 |
| NCI/ADR-RES | Breast (Mutli-drug resistant) | 0.4 |
| MCF-7 | Breast | 0.6 |
| SW-480 | Colorectal | 0.2 |
| B16-F1 | Murine Melanoma | 0.06 |
| HMEC | Normal Breast | 4.00 |

*The inhibiting concentration 50 ($IC_{50}$) is based on measurements of ATP levels taken 72 h post-treatment compared to untreated cells.

6.3 Example 3

Effect of Compound 1 Tartrate on Growth of Cervical Tumor Cells In Vivo

To demonstrate the antitumor activity of Compound 1 Tartrate in vivo, experiments were conducted in CB17 SCID/SCID mice (Charles River, Mass., USA) into which were injected C33A human cervical cancer cells. The resultant mice are a model for a human having cervical cancer.

The C33A human cervical cancer cells were maintained in RPMI (Hyclone, Utah, USA) supplemented with 10% inactivated fetal bovine serum (Bio-Whittaker, MD, USA) and 1% penicillin-streptomycin-L-Glutamine (Gibco, N.Y., USA), under 5% $CO_2$ at 37° C., and passaged twice a week. The cells were grown at a confluency lower than 70% and than collected with Trypsin (Bio-Whittaker, MD, USA). The cells were then centrifuged and washed twice using phosphate buffered saline solution (PBS) and resuspended in PBS at $2\times10^6$ cells per 100 µl Viability was examined by staining with trypan blue (Gibco, N.Y., USA) and only flasks with cell viability greater than 95% were used for in vivo studies.

C33A cells were injected subcutaneously into the flank of female CB17 SCID/SCID mice. Each mouse was inoculated with a suspension of $2\times10^6$ tumors cells per 150 µl on day zero. There were three treatment groups of ten mice each: (a) a negative control group, (b) a positive control group and (c) a group treated with Compound 1 Tartrate.

Treatments started on day fourteen after C33A cells transplantation. Compound 1 Tartrate was administered IV once daily for five consecutive days at a dose of 4.5 mg/kg. Compound 1 Tartrate was prepared fresh daily in a vehicle solution of 5% Dextrose (Abbot Laboratories, QC, Canada) and 2% polysorbate 20 (Sigma, St. Louis, Mo., USA). The negative control group was treated with vehicle alone. The injection volume for both Compound 1 Tartrate group and the negative control group was 150 µl. The positive control group was treated once every 3 days for five times with cisplatin (Sigma, St. Louis, Mo., USA) at a dose of 4 mg/kg. Cisplatin was formulated in PBS on each day of the injection and was administered IP in an injection volume of 80 µl.

The mice were weighed and the tumors measured on day 13 and every 2 days after treatment commenced. Observation continued for 40 days after initial tumor implantation. The changes in body weight and in the calculated tumor volume were plotted.

Figure 2:
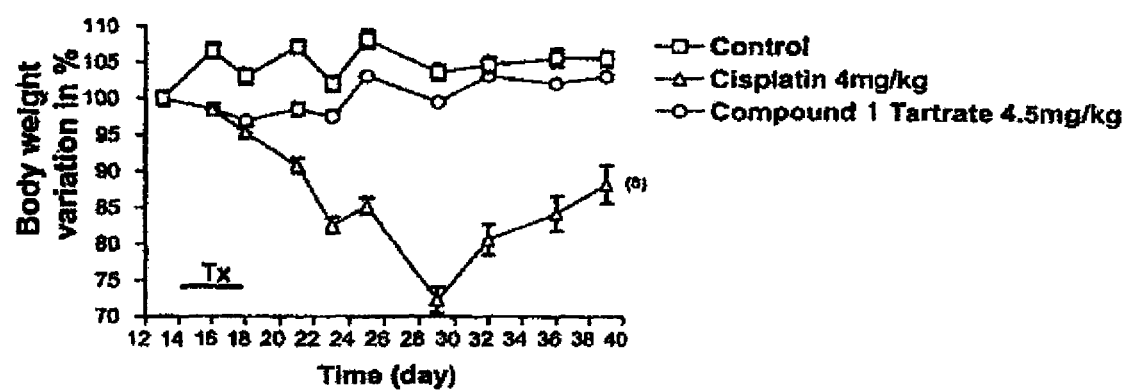
FIG. 2 illustrates the variation in body weight of SCID mice over time following treatment with cisplatin at a dose of 4 mg/kg or Compound 1 tartrate at a dose of 4.5 mg/kg. Line -□- represents the control group, line -Δ- represents the cisplatin treatment group, and line -○- represents the Compound 1 tartrate treatment group.

As shown in FIG. 2, mice treated with Compound 1 Tartrate experienced a non-significant weight loss, whereas the cisplatin treated positive control group had a weight loss of 28% on day 29. Two mice died in the cisplatin group on days 29 and 32 after losing 2.2 g and 7 g of body weight, respectively.

Figure 3:
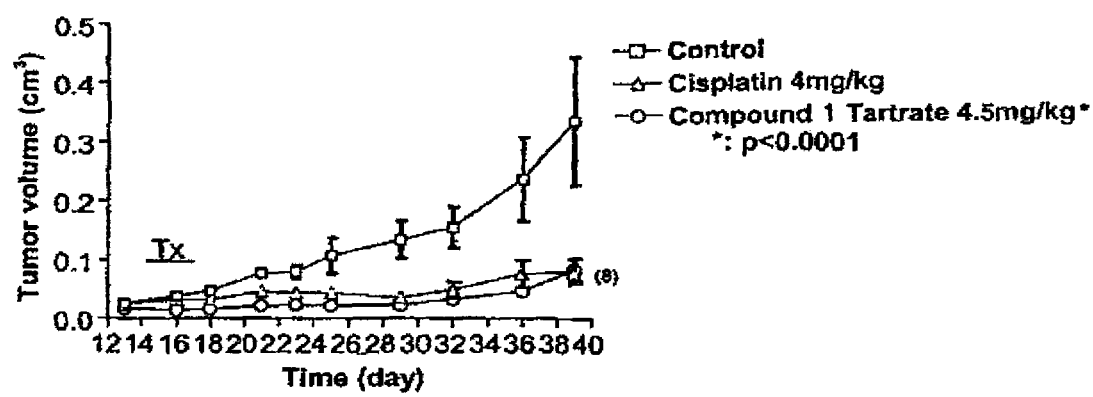
FIG. 3 illustrates the change in tumor volume in SCID mice which were implanted with C33A human cervical cancer cells and treated with cisplatin at a dose of 4 mg/kg or Compound 1 tartrate at a dose of 4.5 mg/kg. Line -□- represents the control group, line -Δ- represents the cisplatin treatment group, and line —O— represents the Compound 1 tartrate treatment group.

As shown in FIG. 3, Compound 1 tartrate treatment at a dose of 4.5 mg/kg once a day for five days resulted in a statistically significant (p<0.0001) reduction in tumor growth compared to mice treated with vehicle only. On days 36 and 39, animals treated with 4.5 mg/kg of Compound 1 tartrate had significantly (p<0.001) smaller tumors on average than animals treated with vehicle only. The T/C values on days 36 and 39 were 14% and 22%, respectively. On average, no significant changes in body weight were noted.

As indicated in FIG. 3, Compound 1 Tartrate significantly reduces the human cervical tumors implanted in SCID mice, an art-accepted model for human cervical cancer. Accordingly, Compound 1 tartrate is useful for inhibiting the growth of cervical cancer and for treating or preventing cervical cancer in a patient, particularly a human patient.

6.4. Example 4

Synthesis of Compound 66 and Compound 67

Scheme 3

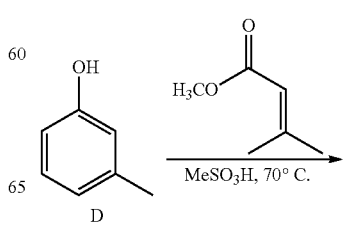

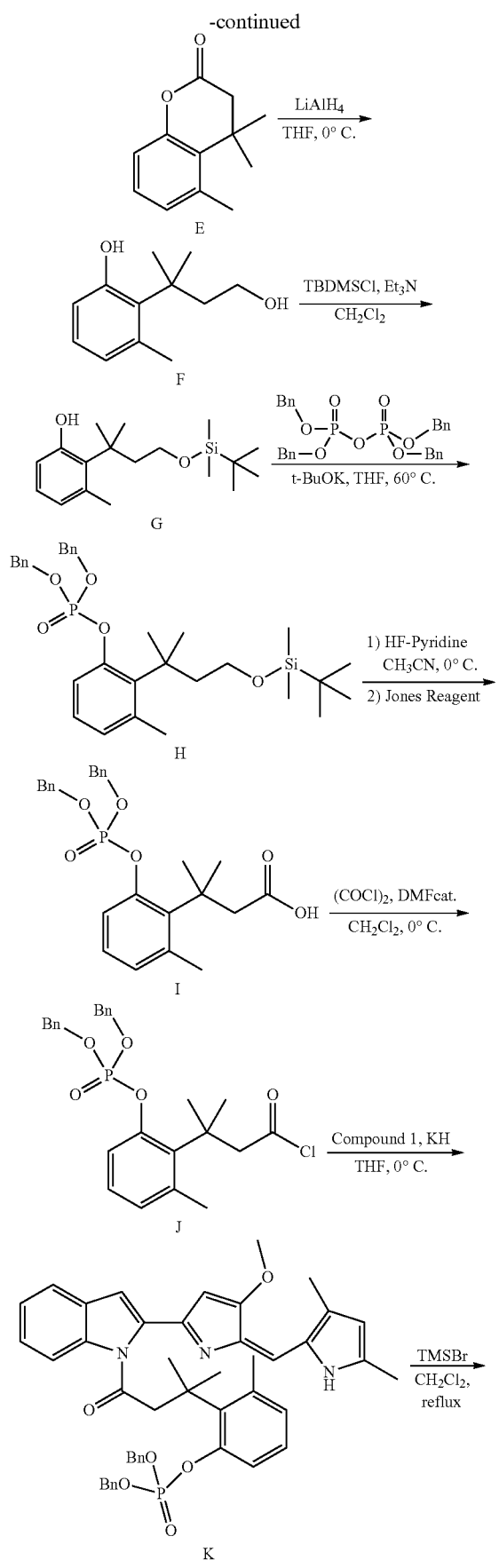

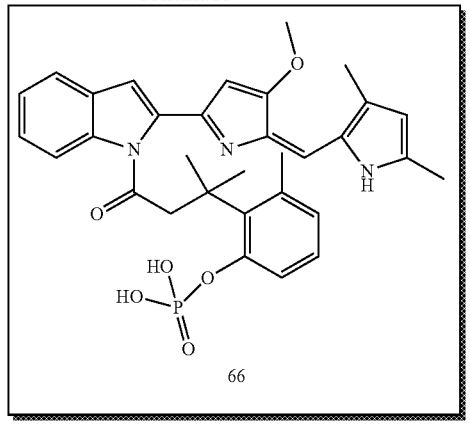

Referring to Scheme 3, Intermediate H was synthesized according to the procedure described by Nicolaou, M. G. et al. *J. Org. Chem.* 1996, 61, 8636-8641.

Referring to Scheme 3, Intermediate H (1 g, 1.76 mmol) was dissolved in acetonitrile (18 mL), cooled to 0° C. and treated with a solution of Hydrogen fluoride-pyridine (1.76 mL) for 5 min to remove the silyl group. The free primary alcohol was oxidized to the carboxylic acid with Jones reagent (6 mL, added over a period of 30 min) and the reaction was kept at 0° C. under vigorous stirring for 1 h. 2-propanol (4 mL) was added to quench the residual Jones reagent and the mixture was stirred for an additional 10 min. Saturated aqueous $NH_4Cl$ solution (40 mL) and EtOAc (30 mL) were added and the layers were separated. The organic phase was washed with saturated aqueous $NH_4Cl$ (2×40 mL), dried over anhydrous $Na_2SO_4$ and filtered over a sintered glass filter funnel. The solvent was removed by rotary evaporation to afford a yellow-green oil that was purified by column chromatography over silica gel using a gradient of 0-50% EtOAc/hexane as eluent. Carboxylic acid I was isolated as a colorless oil.

Yield: 570 mg, 70%. $^1$H NMR (300 MHz, $CDCl_3$): δ (ppm) 1.45 (s, 6H); 2.19 (s, 3H); 2.78 (s, 1H); 5.07-5.16 (m, 4H); 6.87 (m., 1H); 7.09-7.22 (m, 2H); 7.31 (s, 9H).

Carboxylic acid I (570 mg, 1.22 mmol) was dissolved in $CH_2Cl_2$ (12 mL) and cooled to 0° C. The solution was treated with oxalyl chloride (138 μL, 1.58 mmol), DMF (50 μL) and stirred for 1 h at room temperature. The solvent was removed by rotary evaporation and the residual acid chloride J was dried in vacuo for 2 h to afford a white solid.

A solution of Compound 1 (309 mg, 0.98 mmol) in THF (5 mL) was cooled to 0° C. and treated with solid potassium hydride (155 mg, 2.94 mmol, 70% oil dispersion). The reaction was stirred at 0° C. for 30 min. Intermediate J was dissolved in THF (5 mL) and added dropwise to the anion of Compound 1. The mixture was stirred at 0° C. for an additional 30 min, then quenched with saturated aqueous $NaHCO_3$ (30 mL). EtOAc (15 mL) was added and the layers were separated. The organic phase was washed with brine (3×30 mL), dried over anhydrous $Na_2SO_4$, filtered over a sintered glass filter funnel and the solvent was removed by rotary evaporation. The residue was purified by column chromatography over silica gel using a gradient of 0-20% EtOAc/hexane as eluent to afford the dibenzyl phosphate prodrug K as an orange solid.

Yield: 320 mg, 42%. M/Z: 768.35 [M+1]. $^1$H NMR (300 MHz, $CDCl_3$): δ (ppm) 1.38 (s, 6H); 2.09 (s, 3H); 2.17 (s, 3H); 2.39 (s, 3H); 5.84 (s, 2H); 3.80 (s, 3H); 4.87-4.99 (m, 4H); 5.84 (s, 1H); 6.01 (s, 1H); 6.46-6.56 (1, 2H); 6.79 (s, 1H); 6.83-6.94 (m, 3H); 7.05-7.13 (m, 2H); 7.15-7.23 (m, 4H); 7.27-7.35 (m, 5H); 7.36-7.45 (m, 2H); 9.93-10.31 (bs, 1H).

The dibenzyl phosphate prodrug K (130 mg, 0.17 mmol) was dissolved in $CH_2Cl_2$ (4 mL), treated with TMSBr (132 µL, 1 mmol) and stirred at reflux for 45 min. The solvent was removed by rotary evaporation and the residue was dried over night in vacuo. The residue was dissolved in $CH_2Cl_2$ (20 mL) and washed with brine (3×40 mL). The organic layer was dried over anhydrous $Na_2SO_4$, filtered over a sintered glass filter funnel and the solvent was removed by rotary evaporation to afford the deprotected phosphate prodrug 66 as a reddish-orange solid.

Yield: 100 mg, 100%. M/Z: 588.28 [M+1]. $^1$H NMR (300 MHz, DMSO-$d_6$): δ (ppm) 1.43 (s, 6H); 1.84 (s, 3H); 2.38 (s, 3H); 2.71 (s, 3H); 3.55-3.71 (bs, 2H); 4.05 (s, 3H); 6.34-6.55 (m, 3H); 6.92-7.06 (m, 2H); 7.17 (s, 1H); 7.23 (s, 1H); 7.26-7.47 (m, 2H); 7.58-7.73 (d, 1H); 7.75-7.90 (d, 1H).

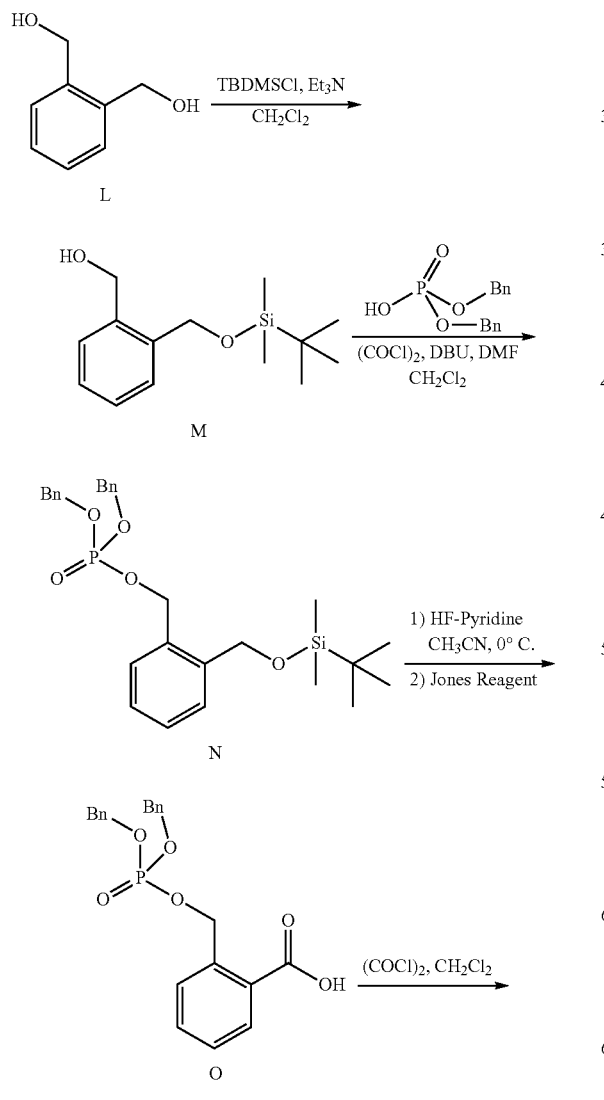

Referring to Scheme 4,1,2-Benzenedimethanol (L, 3 g, 21.7 mmol) and TBDMSCl (2.94 g, 19.5 mmol) were dissolved in $CH_2Cl_2$ (28 mL), cooled to 0° C. then treated with a solution of triethylamine (12.1 mL, 86.8 mmol) in $CH_2Cl_2$ (11 mL). The mixture was stirred at room temperature for 1 h and the solvent was removed by rotary evaporation. The residue was dissolved in EtOAC (30 mL) and washed with brine (3×60 mL). The organic layer was dried over anhydrous $Na_2SO_4$ and filtered over a sintered glass filter funnel. The solvent was removed by rotary evaporation to afford the silylated benzyl alcohol M as a colorless oil. Yield: 4.5 g, 91%. $^1$H NMR (300 MHz, CDCl$_3$): δ (ppm) 0.06 (s, 6H); 0.80 (s, 9H); 2.99-3.19 (bs, 1H); 4.56 (s, 2H); 4.70 (s, 2H); 7.14-7.32 (m, 4H).

A solution of dibenzyl phosphate (3.76 g, 13.5 mmol) in $CH_2Cl_2$ (10 mL) was treated with oxalyl chloride (1.17, 13.5 mmol) and DMF (0.5 mL). The mixture was stirred at room temperature for 1 h, the solvent was removed by rotary evaporation and the residue was dried in vacuo for 2 h to afford dibenzyl chlorophosphate as a yellowish solid. The residue was suspended in $CH_2Cl_2$ (5 mL), cooled to 0° C., treated with a solution of benzylic alcohol M (1.7 g, 6.7 mmol) in $CH_2Cl_2$ (5 mL) then DBU (2.02 mL, 13.5 mmol, added dropwise). The mixture was stirred at room temperature for 1 h30, and the solvent was removed by rotary evaporation. The residue was purified by column chromatography over silica gel using a gradient of 0-10% EtOAc/hexane as eluent.

Yield: 1.3 g, 40%. $^1$H NMR (300 MHz, $CDCl_3$): δ (ppm)-0.01 (s, 6H); 0.83 (s, 9H); 4.65 (s, 2H); 4.87-4.96 (d, 4H); 4.96-5.06 (d, 2H); 7.07-7.41 (m, 14H).

Dibenzyl phosphate N (1.3 g, 2.53 mmol) was dissolved in acetonitrile (25 mL), cooled to 0° C. and treated with a solution of Hydrogen fluoride-pyridine (2.5 mL) for 5 min to remove the silyl group. The free primary alcohol was oxidized to the carboxylic acid with Jones reagent (5 mL, added over a period of 30 min) and the reaction was kept at 0° C. under vigorous stirring for 1 h. 2-propanol (6 mL) was added to quench the residual Jones reagent and the mixture was stirred for an additional 10 min. Saturated aqueous $NH_4Cl$ solution (40 mL) and EtOAc (30 mL) were added and the layers were separated. The organic phase was washed with saturated aqueous $NH_4Cl$ (2×40 mL), dried over anhydrous $Na_2SO_4$ and filtered over a sintered glass filter funnel. The solvent was removed by rotary evaporation to afford a yellow oil that was used in the next step without any purification.

Yield: 1.0 g, 98%. $^1$H NMR (300 MHz, $CDCl_3$): δ (ppm) 5.04-5.17 (d, 4H); 5.56-5.5.67 (d, 2H); 7.27-7.41 (m, 11H); 7.48-7.58 (m, 2H); 7.80-8.12 (m, 1H).

Benzoic acid O (1.0 g, 2.42 mmol) was dissolved in $CH_2Cl_2$ (24 mL) and cooled to 0° C. The solution was treated with oxalyl chloride (420 µL, 4.84 mmol), DMF (50 µL) and stirred for 1 h at room temperature. The solvent was removed by rotary evaporation and the residual benzoyl chloride P was dried in vacuo for 2 h to afford a white solid.

A solution of Compound 1 (384 mg, 1.21 mmol) in THF (12 mL) was cooled to 0° C. and treated with solid potassium hydride (192 mg, 3.64 mmol, 70% oil dispersion). The reaction was stirred at 0° C. for 30 min. Intermediate P was dissolved in THF (5 mL) and added dropwise to the anion of Compound 1. The mixture was stirred at 0° C. for an additional 30 min, then quenched with saturated aqueous $NaHCO_3$ (30 mL). EtOAc (15 mL) was added and the layers were separated. The organic phase was washed with brine (3×30 mL), dried over anhydrous $Na_2SO_4$, filtered over a sintered glass filter funnel and the solvent was removed by rotary evaporation. The residue was purified by column chromatography over silica gel using a gradient of 0-20% EtOAc/hexane as eluent to afford the dibenzyl phosphate prodrug Q as an orange solid.

Yield: 422 mg, 50%. M/Z: 712.24 [M+1]. $^1$H NMR (300 MHz, $CDCl_3$): δ (ppm) 1.91 (s, 3H); 2.12 (s, 3H); 3.77 (s, 3H); 4.85-4.96 (d, 4H); 5.33-5.44 (d, 2H); 5.71 (s, 1H); 5.79 (s, 1H); 6.79 (s, 1H); 7.06 (s, 1H); 7.11-7.35 (m, 15H); 7.41-7.68 (m, 4H).

Dibenzyl phosphate prodrug Q (100 mg, 0.14 mmol) was dissolved in wet $CH_2Cl_2$ (2 mL) and treated with TFA (2 mL) The mixture was stirred at reflux for 3 h, and the solvent was removed by rotary evaporation. Phosphate prodrug 67 was purified by RP-HPLC on a $C_{18}$ column using a gradient of $H_2O/CH_3CN$ as mobile phase (pH 9).

M/Z: 532.17 [M+1]. $^1$H NMR (300 MHz, DMSO-$d_6$): δ (ppm) 2.30 (s, 3H); 2.40 (s, 3H); 3.98 (s, 3H); 4.65-4.81 (d, 2H); 6.24 (s, 1H); 6.43 (s, 1H); 6.48-6.60 (d, 2H); 7.05-7.18 (m, 2H); 7.19-7.3 (m, 1H); 7.33 (s, 1H); 7.39-7.46 (d, 2H); 7.46-7.54 (m, 1H); 7.54-7.64 (m, 1H); 7.64-7.75 (m, 1H).

6.5 Example 5

Solubility of Compound 1 Tartrate, Compound 1 Mesylate Salt and Compound 66

To determine whether a compound is soluble in a solution, the solution was filtered on 0.2 µM polytetrafluoroethylene filters (Whatman Inc. Clifton, N.J., USA) and the compound concentration in the filtrate was measured by LC/MS and compared to the expected concentration. If the concentration of the compound in the filtrate was equal +/−15% to the expected concentration, the compound was judged to be soluble in the solution.

The detection of Compound 1 Tartrate, Compound 1 Mesylate Salt or Compound 66 by LC/MS was carried out using the HPLC system that consisted of a Waters Alliance quaternary gradient HPLC pump (Waters, Milford, Mass., USA) and a $ZQ_{2000}$ single quadrupole mass spectrometer (Waters, Milford, Mass., USA). The column used was XTerra MS C18: 50×2.1 mm, 3.5 mm column at 20° C. Samples were injected and separated under the following conditions: The mobile phase "A" consisted of 5 mM ammonium formate, 0.1% formic acid in water and mobile phase "B" consisted of 5 mM ammonium formate, 0.1% formic acid in methanol. A linear gradient was applied as follows: 0 to 1 min, 94% "A" and 6% "B"; 1 to 4 mM, 6% to 100% "B"; 4 to 8 mM 100% "B"; 8 to 9 min, 100% "B" to 6% "B"; 9 to 12 mM, 94% "A" and 6% "B". The Mass Spectrometer system consisted of a Waters $ZQ_{2000}$ single quadrupole mass spectrometer (Waters, Milford, Mass., USA) equipped with an Electrospray Ionization Source (ES). The mass detector was operated in positive ion mode (ES+) and Selected Ion Recording mode (SIR). Compounds were detected at m/z equal to their respective molecular weight plus 1.

Compound 1 is poorly soluble in water. Compound 1 Tartrate salt solubility is equal to 0.1 mg/mL. Compound 1 Mesylate salt is the preferred salt as its solubility is four fold greater (0.4 mg/mL). This increase in solubility has a positive impact on the shelf stability of formulated Compound 1. A formulation containing 0.6 mg/mL of Compound 1 Tartrate Salt, 9.6% polyethylene glycol 300, 0.4% polysorbate 20 and 5% dextrose tends to precipitate one hour after its preparation as 40% to 50% of the Compound 1 Tartrate is retained by a 0.2 µM filter. Conversely, a formulation containing 0.6 mg/mL of Compound 1 Mesylate Salt, 9.6% polyethylene glycol 300, 0.4% polysorbate 20 and 5% dextrose shows no evidence of precipitation 72 hours after its preparation. Hence, Compound 1 Mesylate Salt represents a significant improvement because it sufficiently increases the stability of the formulation so it can be used in the clinic.

The addition of a phosphate increases solubility of a poorly soluble compound. The phosphate prevents the compound from entering cells but it can be gradually removed by alkaline phosphatase in the plasma. Hence, the compound to which a phosphate is added is a pro-drug. For example, Compound 66 is the phosphate pro-drug of Compound 1 and the solubility of Compound 66 in water is equal to 10 mg/mL: 100 fold greater than Compound 1 Tartrate. In vivo, because the phosphate is not removed instantly by alkaline phosphatase, the pro-drug has the time to disperse itself in the total blood volume. As the phosphate group is removed, the liberated drug has time to distribute itself in the tissue. Hence, the less soluble drug doesn't precipitate in the blood. The advantage of a pro-drug is that it can be injected in a smaller volume because it can be formulated at high concentration in aqueous solution.

6.6 Example 6

The Conversion of Phosphate Pro-Drug Compound 66 into its Biologically Active Counterpart by Alkaline Phosphatases In Vitro The conversion into biologically active drug of phosphate pro-drugs by calf intestinal alkaline phosphatase and human placental alkaline phosphatase was measured in vitro using purified enzymes. Purified calf intestinal alkaline phosphatase (Roche Diagnostic Inc. Laval, Quebec, Canada) or human placental alkaline phosphatase (Sigma-Aldrich Canada Ltd. Oakville, Ontario, Canada) was added at a concentration of 0.02 U/100 µL to a solution containing 15 µM of Compound 66, 20 mM Tris-HCl, pH 7.4 and 0.9% NaCl. The solutions were incubated for 30, 60 or 120 minutes. A solution containing 15 µM of Compound 66, 20 mM Tris-HCl, pH 7.4 and 0.9% NaCl was used as a reference (time=0 minutes). To each solution, an equal volume (100 µL) of ice-cold acetonitrile was added, and then the mixture was vortexed and transferred to glass vials. A standard concentration curve of the pro-drug and the drug was prepared in 10 mM Tris-HCl, pH 7.4, 0.45% NaCl and 50% acetonitrile. All samples were immediately analyzed by LC/MS.

As shown on FIGS. 4 and 5, both the calf intestinal alkaline phosphatase and human placental alkaline phosphatase, can convert a fraction of the pro-drug Compound 66 present in solution into the drug Compound 1 within two hours.

6.7 Example 7

Effect of Compound 1 Mesylate Salt and Compound 66, Respectively, on Growth of Prostate Tumor Cells In Vivo The human prostatic adenocarcinoma cancer PC3 cells were purchased from the American Type Culture Collection (ATCC). These cells were confirmed to be free of mycoplasma infection. Cells were maintained in the Roswell Park Memorial Institute (RPMI), supplemented with 10% inactivated fetal bovine serum and 1% penicillin-streptomycin-L-Glutamine, under 5% carbon dioxide ($CO_2$) at 37° C. For prostatic-tumor induction, cells were grown lower than 70% confluence in complete medium and then collected with trypsin (Bio Whittaker, Rockland, Me., USA). Cells were then centrifuged and washed 2 times in phosphate buffer solution (PBS) and resuspended in PBS at $1.5 \times 10^6$ cells/0.1 mL. PC3 cells were then transplanted subcutaneously into the flank of SCID mice (Charles River Laboratories, Wilmington, Mass., USA), as a suspension of tumor cells ($1.5 \times 10^6$ cells in 100 µL PBS), under a laminar airflow hood. Eleven (11) days later, the size of each tumor was measured. Ten days after transplantation, mice were randomized into groups of 10 mice each based on tumor size so that the average tumor size in each group was comparable. Relative tumor size and volume was calculated as follows: length (cm)×[width (cm)]$^2$/2. Mice then received 5 consecutive intravenous (tail vein) injections of either 200 µL of 9.6% polyethylene glycol 300, 0.4% polysorbate 20 and 5% dextrose (Vehicle only), 4.84 µMoles/Kg of Compound 1 Mesylate Salt formulated in 9.6% polyethylene glycol 300, 0.4% polysorbate 20 and 5% dextrose, 4.84 µMoles/Kg of Compound 66 (pro-drug) formulated in 5% dextrose, or 14.51 µMoles/Kg of Compound 66 (pro-drug) formulated in 5% dextrose. As shown in FIG. 6, both Compound 1 Mesylate Salt and Compound 66 (pro-drug) significantly reduce the growth of prostatic tumors in mice.

6.8 Example 8

Effects of Compounds on Cancer Cell Viability In Vitro

To further demonstrate the anti-oncogenic effect of the Triheterocyclic Compounds of the invention, several compounds were synthesized and their effect on cancer cell viability was demonstrated by measuring the cellular ATP levels in H1299 and C33A cancer cell lines as described in Example 2 of this application. As depicted in Table 4, these compounds were efficient in decreasing cellular ATP levels in H1299 and C33A cancer cell lines. Nevertheless, these compounds are believed to have utility in the in vivo methods of the invention, i.e., treatment and prevention of cancer and viral infections, respectively. It should be noted that, although this cell-based assay is believed to be indicative of anti-oncogenic activity in vivo, it is not the only useful assay for evaluating the anti-oncogenic activity of Triheterocyclic Compounds of the invention. In addition, the anti-viral and other biological activity of compounds of the invention can be determined and evaluated in other assay systems known to the skilled artisan.

It should also be noted that for in vivo medicinal uses, potency is not the only factor to be considered to estimate the suitability of a compound as a pharmaceutical agent. Other factors such as toxicity and bioavailability also determine the suitability of a compound as a pharmaceutical agent. Toxicity and bioavailability can also be tested in any assay system known to the skilled artisan.

TABLE 4

IC50s of Compounds in µM for their Effect on Cancer Cells Viability

| Compound | R1 | R3 | R4 | R5 | R6 | R7 | R8 | R9 | R10 | R11 | R12 | IC50 (µM) H1299 | IC50 (µM) C33A |
|---|---|---|---|---|---|---|---|---|---|---|---|---|---|
| 2 | H | CH₃ | I | CH₃ | H | OCH₃ | H | H | H | H | H | 0.530 | 0.650 |
| 3 | H | CH₃ | H | OCH₃ | H | OCH₃ | H | H | H | OCH₃ | H | 0.300 | 0.520 |
| 4 | H | CH₃ | H | CH₃ | H | OCH₃ | H | H | H | OCH₃ | OCH₃ | 0.215 | 0.250 |
| 5 | C(O)OC(CH₃)₃ | CH₃ | H | CH₃ | H | OCH₃ | H | H | H | OCH₃ | OCH₃ | 2.260 | 2.240 |
| 6 | H | CH₃ | H | CH₃ | H | OCH₃ | H | H | H | H | H | 0.267 | 0.190 |
| 7 | H | CH₃ | H | CH₃ | H | OCH₃ | H | Morpholin-4-ylmethyl | H | Br | H | 1.730 | 2.230 |
| 8 | H | CH₃ | H | CH₃ | H | OCH₃ | H | 4-phenyl-piperazin-1ylmethyl | H | H | H | 1.880 | 1.760 |
| 9 | H | CH₃ | H | CH₃ | H | OCH₃ | CH₂OH | CH₂NHCH₂CH₂OH | H | H | H | 4.427 | 2.210 |
| 10 | H | CH₃ | H | CH₃ | H | OCH₃ | CH₂OH | CH₂NHCH₃ | H | H | H | 0.493 | 0.250 |
| 11 | H | CH₃ | H | CH₃ | H | OCH₃ | CH₂OH | CH₂NHC(CH₃)₂ | H | H | H | 0.983 | 0.307 |

TABLE 4-continued
IC50s of Compounds in µM for their Effect on Cancer Cells Viability
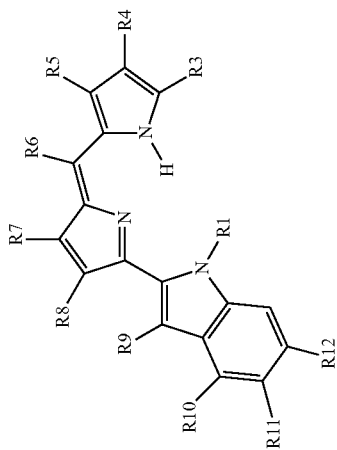
| Com-pound | R1 | R3 | R4 | R5 | R6 | R7 | R8 | R9 | R10 | R11 | R12 | IC50 (µM) H1299 | C33A |
|---|---|---|---|---|---|---|---|---|---|---|---|---|---|
| 12 | H | CH₃ | H | CH₃ | H | OCH₃ | H | | H | H | H | 2.95 | 3.600 |
| 13 | H | CH₃ | H | CH₃ | H | OCH₃ | | CH₂OH CH₂NHCH₂CHCH₂ | H | H | H | 0.717 | 0.440 |
| 15 | H | CH₃ | H | CH₃ | H | OCH₃ | | H | H | OCH₃ | H | 0.935 | 1.440 |
| 17 | H | CH₃ | I | CH₃ | H | OCH₃ | | H I | H | H | H | 5.370 | 5.690 |
| 20 | H | CH₃ | C(O)C(O)OCH₂CH₃ | CH₃ | H | OCH₃ | | C(O)C(O)OCH₂CH₃ | H | H | H | 7.983 | 7.227 |
| 22 | H | CH₃ | H | CH₃ | H | OCH₃ | H | 5-pyridin-2yl-thiophen-2yl-methanone | H | H | H | 7.193 | 6.457 |

TABLE 4-continued

IC50s of Compounds in μM for their Effect on Cancer Cells Viability

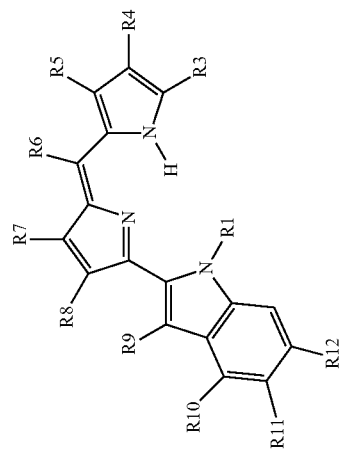

| Compound | R1 | R3 | R4 | R5 | R6 | R7 | R8 | R9 | R10 | R11 | R12 | IC50 (μM) H1299 | IC50 (μM) C33A |
|---|---|---|---|---|---|---|---|---|---|---|---|---|---|
| 27 | H | CH₃ | H | CH₃ | H | OCH₃ | H | 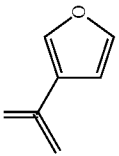 furan-3yl-methanone | H | H | H | 15.34 | 10.00 |
| 30 | C(O)OC(CH₃)₃ | CH₃ | H | CH₃ | H | OCH₃ | H | H | H | OCH₃ | H | 50.00 | 50.00 |
| 35 | C(O)CH(CH₃)₂ | CH3 | H | CH₃ | H | OCH₃ | H | H | H | H | H | 0.197 | 0.167 |
| 36 | H | CH3 | H | CH₃ | H | OCH₃ | H | H | OC(O)OC(CH₃)₃ | H | H | 0.494 | 0.583 |
| 37 | H | CH3 | H | CH₃ | H | OCH(CH₃)₂ | H | H | H | H | H | 1.355 | 1.288 |
| 38 | C(O)N(CH₃)₂ | CH3 | H | CH₃ | H | OCH(CH₃)₂ | H | H | OC(O)OC(CH₃)₃ | H | H | 0.342 | 0.226 |
| 39 | CH₂CH₂OH | CH3 | H | CH₃ | H | OCH₃ | H | H | H | H | H | 5.667 | 2.950 |
| 40 | H | CH3 | CH₂CH₂CH₂OH | CH₃ | H | OCH₃ | H | H | H | H | H | 8.462 | 7.168 |
| 41 | H | CH3 | H | CH₃ | H | OCH(CH₃)₂ | H | H | H | H | H | 3.347 | 1.788 |
| 42 | C(O)Ph | CH3 | H | CH₃ | H | OCH₃ | H | H | H | F | H | 0.458 | 0.358 |
| 43 | C(O)OCH₂CH(OH)CH₂OH | CH3 | H | CH₃ | H | OCH₃ | H | H | H | F | H | 0.298 | 0.196 |
| 44 | H | CH3 | H | CH₃ | H | OCH(CH₃)₂ | H | H | H | H | H | 1.277 | 1.257 |
| 45 | H | CH3 | H | CH₃ | H | OCH(CH₃)₂ | H | H | H | H | F | 0.887 | 0.716 |
| 46 | H | CH3 | H | CH₃ | CH3 | OCH₃ | H | H | H | H | Cl | 0.245 | 0.261 |
| 47 | H | CH3 | H | CH₃ | H | OCH₃ | H | H | H | H | H | 9.650 | 8.278 |
| 48 | C(O)OC(CH₃)₃ | CH3 | H | CH₃ | H | OCH₃ | H | C(O)NHCH₂CH₂CH₂OH | H | H | H | 50 | 11.08 |
| 49 | H | CH3 | H | CH₃ | H | OCH₃ | H | H | H | H | H | 3.000 | 2.000 |
| 50 | H | CH3 | H | CH₃ | H | OCH₃ | H | H | OCH₂C(O)OCH₂CH₃ | H | H | 1.206 | 0.509 |

TABLE 4-continued
IC50s of Compounds in µM for their Effect on Cancer Cells Viability
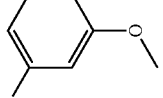
| Compound | R1 | R3 | R4 | R5 | R6 | R7 | R8 | R9 | R10 | R11 | R12 | IC50 (µM) H1299 | IC50 (µM) C33A |
|---|---|---|---|---|---|---|---|---|---|---|---|---|---|
| 51 | H | CH₃ | H | CH₃ | H | 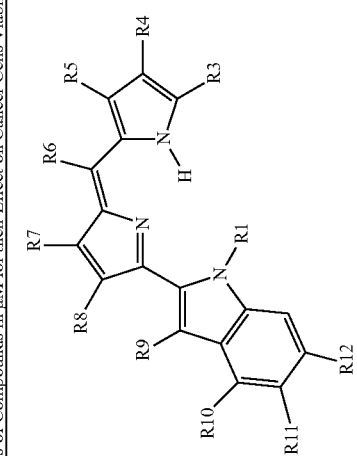 3-methoxy-phenyloxy | H | H | H | H | H | 0.202 | 0.165 |
| 52 | 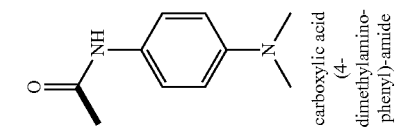 carboxylic acid (4-dimethylamino-phenyl)-amide | CH₃ | H | CH₃ | H | OCH₃ | H | H | H | H | H | 1.044 | 1.106 |

TABLE 4-continued
IC50s of Compounds in μM for their Effect on Cancer Cells Viability
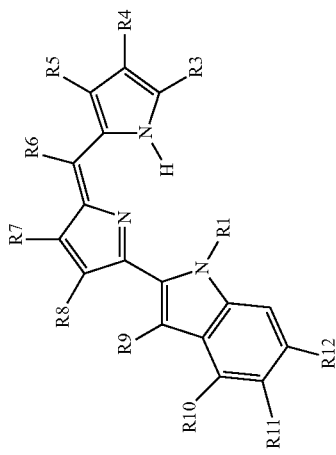
| Compound | R1 | R3 | R4 | R5 | R6 | R7 | R8 | R9 | R10 | R11 | R12 | IC50 (μM) H1299 | IC50 (μM) C33A |
|---|---|---|---|---|---|---|---|---|---|---|---|---|---|
| 53 | H | CH₃ | H | CH₃ | H | OCH₂C(O)OCH₂CH₃ | H | H | H | H | H | 10.62 | 10.15 |
| 54 | carboxylic acid 94-benzyloxy-phenyl)-amide | CH₃ | H | CH₃ | H | OCH₃ | H | H | H | H | H | 0.187 | 0.145 |
| 55 | 4-bromo-phenyl-methanone | CH₃ | H | CH₃ | H | OCH₃ | H | H | H | H | H | 0.173 | 0.173 |

TABLE 4-continued

IC50s of Compounds in μM for their Effect on Cancer Cells Viability

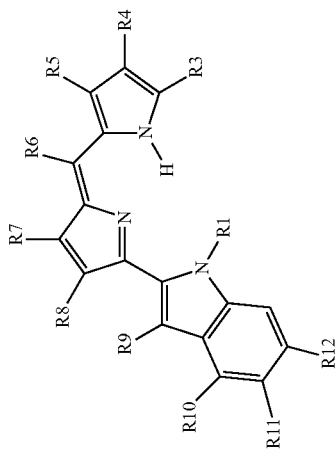

| Compound | R1 | R3 | R4 | R5 | R6 | R7 | R8 | R9 | R10 | R11 | R12 | IC50 (μM) H1299 | C33A |
|---|---|---|---|---|---|---|---|---|---|---|---|---|---|
| 56 | H | CH₃ | H | CH₃ | H | OC(CH₃)₂ | H | H | H | H | OH | 5.956 | 2.535 |
| 57 | H | CH₃ | H | CH₃ | H | OC(CH₃)₂ | H | H | OH | H | H | 5.898 | 3.753 |
| 58 | H | CH₃ | H | CH₃ | H | OCH₃ | H | H | H | | | 1.970 | 1.318 |
| 59 | H | CH₃ | H | CH₃ | H | OCH₃ | H | H | OH | H | H | 5.837 | 5.598 |
| 61 | H | CH₃ | H | CH₃ | H | HN—(4-methoxyl-phenyl-amine) | H | H | H | | | 1.113 | 0.930 |
| 63 | H | CH₃ | CH₂CH₂C(O)OCH₃ | CH₃ | H | OCH₃ | H | H | H | H | H | 0.753 | 0.548 |
| 64 | CH₂OC(O)C(CH₃)₃ | CH₃ | H | CH₃ | H | OCH₃ | H | H | H | H | H | 13.29 | 14.25 |
| 65 | CH₂CH₂OS(O)₂O⁻Na⁺ | CH₃ | H | CH₃ | H | OCH₃ | H | H | H | H | H | 7.891 | 5.973 |

R1 = p-methyl-phenol (compound 58)

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A composition comprising a pharmaceutically acceptable carrier or vehicle and the compound

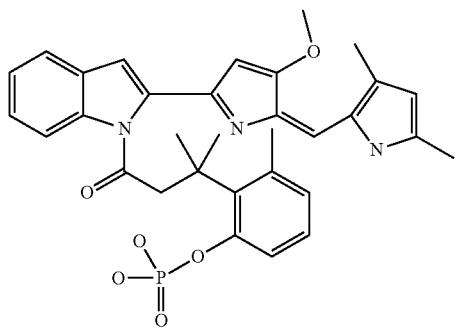 [SMILES: COC1=CC(c2cc3ccccc3n2C(=O)CC(C)(C)c2c(C)cccc2OP(=O)(O)O)=N/C1=C/c1[nH]c(C)cc1C]

or a pharmaceutically acceptable salt thereof.

2. A composition comprising a pharmaceutically acceptable carrier or vehicle and the compound

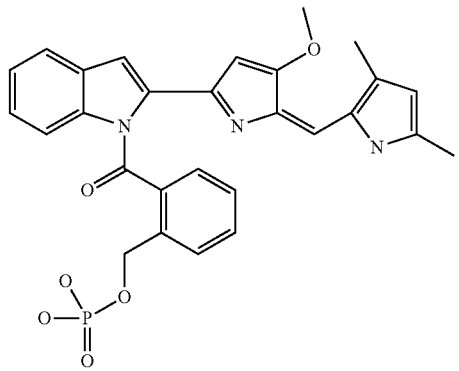 [SMILES: COC1=CC(c2cc3ccccc3n2C(=O)c2ccccc2COP(=O)(O)O)=N/C1=C/c1[nH]c(C)cc1C]

or a pharmaceutically acceptable salt thereof.

3. A compound selected from

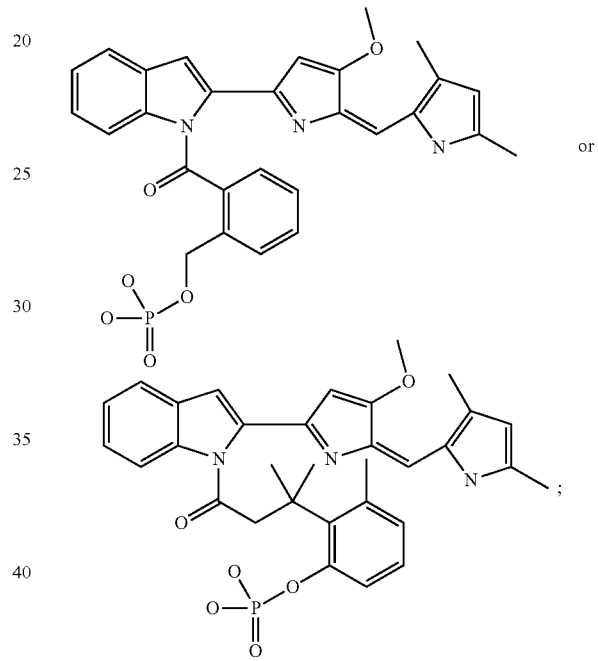

or a pharmaceutically acceptable salt thereof.

* * * * *